(12) United States Patent
Naessens et al.

(10) Patent No.: US 8,064,063 B2
(45) Date of Patent: Nov. 22, 2011

(54) OPTICAL CHARACTERISATION METHODS AND SYSTEMS

(75) Inventors: Kris Naessens, Melle (BE); Ronny Bockstaele, Merelbeke (BE); Bert Luyssaert, Ghent (BE); Roeland Baets, Deinze (BE)

(73) Assignee: Trinean NV, Gentbrugge (BE)

( * ) Notice: Subject to any disclaimer, the term of this patent is extended or adjusted under 35 U.S.C. 154(b) by 248 days.

(21) Appl. No.: 12/374,255

(22) PCT Filed: Jul. 20, 2007

(86) PCT No.: PCT/BE2007/000085
§ 371 (c)(1),
(2), (4) Date: Jan. 16, 2009

(87) PCT Pub. No.: WO2008/009075
PCT Pub. Date: Jan. 24, 2008

(65) Prior Publication Data
US 2009/0323069 A1    Dec. 31, 2009

(30) Foreign Application Priority Data

Jul. 20, 2006 (EP) .................................. 06015121
Jul. 20, 2006 (GB) .................................. 0614424.0

(51) Int. Cl.
*G01N 21/00*    (2006.01)

(52) U.S. Cl. ........................... 356/441; 356/436

(58) Field of Classification Search .................. None
See application file for complete search history.

(56) References Cited

U.S. PATENT DOCUMENTS

| | | | |
|---|---|---|---|
| 4,088,448 A | 5/1978 | Lilja et al. | |
| 4,330,206 A | 5/1982 | Gausmann et al. | |
| 5,427,959 A | 6/1995 | Nishimura et al. | |
| 5,635,358 A * | 6/1997 | Wilding et al. | 436/165 |
| 5,699,157 A * | 12/1997 | Parce | 356/344 |
| 5,757,482 A * | 5/1998 | Fuchs et al. | 356/246 |
| 6,839,140 B1 * | 1/2005 | O'Keefe et al. | 356/436 |
| 6,867,857 B2 * | 3/2005 | Hobbs | 356/246 |
| 7,756,559 B2 * | 7/2010 | Abreu | 600/318 |
| 2001/0020588 A1 * | 9/2001 | Adourian et al. | 436/180 |
| 2002/0180963 A1 | 12/2002 | Chien et al. | |
| 2003/0017079 A1 | 1/2003 | Hahn et al. | |
| 2003/0049865 A1 * | 3/2003 | Santini et al. | 436/518 |
| 2006/0166243 A1 * | 7/2006 | Su et al. | 435/6 |
| 2006/0257893 A1 * | 11/2006 | Takahashi et al. | 435/6 |

FOREIGN PATENT DOCUMENTS

| | | |
|---|---|---|
| EP | 0 479 231 A1 | 4/1992 |
| FR | 2 325 920 | 4/1977 |
| WO | WO 01/14855 A1 | 3/2001 |

* cited by examiner

*Primary Examiner* — Gregory J Toatley
*Assistant Examiner* — Juan D Valentin
(74) *Attorney, Agent, or Firm* — Bacon & Thomas, PLLC

(57) ABSTRACT

A device (100) for assisting in optical characterisation of a sample fluid. The device can comprise a substrate (102) with at least one measurement reservoir (104) adapted for filling with the fluid (106) in a filling direction. The device (100) thereby is adapted for receiving an illumination beam (108) for illuminating the fluid (106) in the at least one measurement reservoir (104). The at least one measurement reservoir is adapted for varying the rate of change of an optical path length of the illumination beam in the fluid. The measurement reservoir properties are adapted for providing information of an optical path length of the illumination beam in the fluid at a plurality of moments during the filling with the fluid. Furthermore a corresponding optical characterisation device is described. The invention also relates to a corresponding method.

13 Claims, 30 Drawing Sheets

OPTICAL CHARACTERISATION METHODS AND SYSTEMS

TECHNICAL FIELD OF THE INVENTION

The present invention relates to the field of optical characterisation of fluids. More particularly, the present invention relates to components suitable for optical characterisation systems and optical characterisation systems and methods, such as e.g. for optical detection of biological, bio-chemical and/or chemical analytes in fluids.

BACKGROUND OF THE INVENTION

Optical characterisation techniques are frequently used for characterising materials, such as e.g. in material characterisation, medical applications, molecular diagnostics, chemical characterisation, etc. The latter typically may be used for characterising molecules, cells or small particles in small liquid samples, based on the measurement of light absorption and/or fluorescence in the sample. Besides the physical characteristics of the sample, the obtained optical signal typically also depends on the optical path length of the illumination beam in the liquid sample. The latter information typically is required for performing accurate measurements of e.g. the concentration of a particle in a liquid sample. In a large number of today's applications, the amount of fluid material typically available for performing characterisation is limited.

One approach for optically characterising small amounts of fluids is described in International patent application WO 01/14855. A liquid sample is held between two moveable parts comprising optical fibres by surface tension and optical characteristics can be measured by illuminating the sample fluid and collecting a luminescence response thereof. The technique typically requires direct contact between the sample and the read-out unit, implying that the measurement may be disturbed by contaminations originating from previous measurements. Furthermore, due to the lack of a suitable containing structure around the sample fluid, the free air-liquid surface is large and therefore evaporation of the liquid sample can occur on a short time scale.

It is known that small reservoirs, e.g. with a diameter in the order of 1 millimetre or smaller can be used to contain small liquid samples. However, filling of small reservoirs with liquids and control thereof is difficult due to the need for pressure to introduce the fluid in the small reservoir.

SUMMARY OF THE INVENTION

It is an object of the present invention to provide good devices for assisting in optical characterization of fluids and good apparatus and methods for optically characterizing fluids. It is an advantage of particular embodiments of the present invention that small amounts of fluids can be studied, e.g. drops or droplets such as fluids with a volume down to 1 µl, even down to 1 nanoliter. It is also an advantage of particular embodiments of the present invention that the dynamic range in which optical characterization can be performed is large, i.e. that fluids within a wide range of absorption coefficients can be measured. It is an advantage of particular embodiments of the present invention that optical characterization can be performed without contaminating the illumination or detection unit. It is furthermore an advantage of particular embodiments of the present invention that dynamic measurements are performed, i.e. during the filling of the measurement reservoir, as this results in an automated way of coping with different absorption coefficients of the fluids to be characterized. It is also an advantage of particular embodiments of the present invention that the devices, apparatus and methods can be used for different types of optical characterization, such as e.g. photometry, spectrophotometry, fluorometry or spectrofluorometry. It is also an advantage that the gates to the measurement volume or to a predetermined part thereof may be small, e.g. minimised, such that only a small area of the fluid surface is exposed to air and thus the evaporation is limited.

The above objective is accomplished by a method and device according to the present invention.

The present invention relates to a device for assisting in optical characterisation of a fluid, the device comprising a substrate with at least one measurement reservoir adapted for filling with the fluid in a filling direction with a filling rate, the device being adapted for receiving an illumination beam for illuminating the fluid in the at least one measurement reservoir along an optical axis substantially oriented along said filling direction, the at least one measurement reservoir being adapted for varying the rate of change of an optical path length of the illumination beam in the fluid as function of the filling rate, the measurement reservoir being adapted for providing information of the optical path length of the illumination beam in the fluid at a plurality of moments during the filling with the fluid. Adapted for varying the rate of change of an optical path length of the illumination beam in the fluid as function of the filling may comprise adapted for varying the rate of change of an optical path length of the illumination beam in the fluid as function of the amount of sample fluid added to the measurement reservoir. The at least one measurement reservoir may be adapted for, at a constant filling pressure or at a constant filling volumetric flow, varying the rate of change of an optical path length of the illumination beam in the fluid. The filling rate may be predetermined, e.g. variable but predetermined. The filling rate may be fixed. The device may be adapted for use in an optical characterisation system wherein optical characterisation is performed during filling of the measurement reservoir with the fluid. The device therefore may be adapted for performing dynamic optical characterisation, wherein the detected optical signal changes during the measurement, i.e. during different sampling points in the measurement.

The measurement reservoir may comprise sub-reservoirs, whereby the measurement reservoir may be adapted for being illuminated along an illumination path and whereby the sub-reservoirs may be positioned subsequently, e.g. subsequently with respect to their spatial position, along said illumination path in said measurement reservoir. The measurement reservoir may be adapted for having a filling direction with a filling sense from bottom to top and for being illuminated from top to bottom. Alternatively or in addition thereto, the measurement reservoir may be adapted for having a filling direction with a filling sense from bottom to top and for being illuminated from bottom to top.

The device may be adapted for receiving an illumination beam for illuminating the fluid in the at least one measurement reservoir along an optical axis, said optical axis being substantially oriented along said filling direction. The optical axis being substantially oriented along said filling direction typically may mean that the optical axis crosses different cross-sections of the measurement reservoir, the different cross-sections being cross-sections perpendicular to the filling direction of the measurement reservoir. The optical axis may be parallel with the filling direction of the measurement reservoir. The optical axis being substantially oriented along said filling direction can mean that the optical axis is substantially parallel with walls of the measurement reservoir having different hydrophilic properties. It is an advantage of particular embodiments of the present invention that the amount of fluid needed for optical characterisation may be limited. An optical detection system comprising such a device may still be operable even if the measurement reservoir is only partially filled.

The measurement reservoir may be adapted for inducing at least one variation in a behaviour of an optical detection signal generated by interaction between the illumination beam and the fluid in the at least one measurement reservoir as function of the filling, e.g. filling rate.

The measurement reservoir being adapted for inducing at least one variation in a behaviour of an optical detection signal as function of the filling, e.g. filling rate, may comprise the measurement reservoir being adapted for inducing at least one variation in a rate of change of the optical detection signal as function of the filling, e.g. filling rate.

The measurement reservoir shape may comprise a variation in cross-section perpendicular to a filling direction. The device thus may be adapted for use in an optical characterisation system wherein optical characterisation is performed during filling of the measurement reservoir with the fluid. The device therefore may be adapted for performing dynamic optical characterisation, wherein the detected optical signal changes during the measurement, i.e. during different sampling points in the measurement. It is an advantage of embodiments of the present invention that optical characterisation may be performed during the filling of the measurement reservoir with the fluid, allowing to perform optical measurements of fluids having absorbance properties in a large dynamic range.

The measurement reservoir shape may have at least one discontinuity in cross-section perpendicular to a filling direction. It is an advantage of particular embodiments according to the present invention that a good accuracy may be obtained.

The average diameter of cross-sections along a filling direction may be monotonically varying in the filling direction. Monotonically varying in the filling direction may mean that the average diameter of a sequence of cross-sections within the filling direction is always increasing or is always decreasing, whereby no oscillation in size is possible.

The average diameter of cross-sections along a filling direction may be largest at a bottom side of a measurement reservoir first filled with fluid. The bottom side of the measurement reservoir may be connected to the input channel. It is an advantage of particular embodiments of the present invention that sample fluids with a large absorption coefficient or a high excitation rate can be optically characterised.

The measurement reservoir may comprise a number of cross-sections perpendicular to the filling direction crossing an optical path of the illumination beam through said measurement reservoir and at least one intermediate cross-section perpendicular to the filling direction not crossing the optical path of the illumination beam. With an intermediate cross-section there is meant a cross-section lying between a first and a second cross-section with respect to the filling direction, wherein the first and the second cross-section cross the optical path of the illumination beam.

The measurement reservoir may comprise measurement reservoir walls, the measurement reservoir walls having different hydrophilic properties in different parts of the measurement reservoir. The measurement reservoir walls may have different properties at different parts of the measurement reservoir located at different positions with respect to the optical axis of the illumination beam.

The measurement reservoir may comprise at least one dissolvable material adapted for, when being dissolved by contacting with the fluid, providing information of the optical path length of the illumination beam in the fluid.

The measurement reservoir may comprise measurement reservoir side walls, and the measurement reservoir may comprises at least one dissolvable material positioned on a measurement reservoir side wall between a top and bottom of the measurement reservoir with respect to the filling direction.

The measurement reservoir may comprise sub-reservoirs, whereby the measurement reservoir may be adapted for being illuminated along an illumination path and whereby the sub-reservoirs may be positioned subsequently, e.g. subsequently with respect to their spatial position, along said illumination path in said measurement reservoir, at least one of the at least one dissolvable material being positioned on a top or bottom of one of said sub-reservoirs with respect to the filling direction.

The dissolvable material may be adapted for, when being dissolved by contacting with the fluid, changing the absorption coefficient of the fluid.

The measurement reservoir may comprise at least one dissolvable material at the top or bottom of the measurement chamber with respect to the filling direction.

The dissolvable material may provide a reaction with the sample that is measurable optically. The dissolvable material may comprise a colorant.

The dissolvable material may be provided as a dissolvable coating.

The at least one dissolvable material may cover at least part of a measurement reservoir side wall along the filling direction of the measurement reservoir. The latter may provide an increasing absorption coefficient of the fluid.

The at least one dissolvable material may be a plurality of dissolvable materials, each indicative of different information of the optical path length of the illumination beam in the fluid. The plurality of dissolvable materials may be positioned at different positions on the measurement reservoir wall along the filling direction of the measurement reservoir.

The present invention also relates to an optical characterisation device for characterising a fluid, the optical characterisation device comprising an illumination unit, a detection unit, a device for assisting in optical characterisation having a substrate with at least one measurement reservoir and a fluid providing means for filling the at least one measurement reservoir with the fluid in a filling direction, said optical characterisation device being adapted for illuminating the fluid in the at least one measurement reservoir along an optical axis substantially oriented along said filling direction and, said detection unit being controlled for detecting optical detection signals from the fluid at a plurality of moments during the filling of said at least one measurement reservoir. The optical detection signal may be for example any of a transmitted illumination beam, a reflected illumination beam, a fluorescence signal in response to the illumination beam.

The device for assisting in optical characterisation may be a device for assisting as described above.

The measurement reservoir may have predetermined measurement reservoir properties, wherein the optical characterisation device furthermore comprises an evaluation means for determining information of an optical path length of the illumination beam in said sample fluid from said optical detection signals taking into account the measurement reservoir properties. The measurement reservoir properties may be a measurement reservoir shape or properties of the measurement reservoir walls, such as e.g. hydrophilic properties.

The evaluation means may be adapted for determining at least one variation of the optical detection signal behaviour as function of the filling, e.g. filling rate.

The evaluation means may be adapted for determining at least one discontinuity in a rate of change of the optical detection signal as function of the filling, e.g. filling rate.

The optical characterisation device may comprise an optical control means for monitoring illumination properties of said illuminating of the sample in the measurement reservoir. The optical control means may comprise a means for splitting of part of said optical detection signal from the sample and a detector for detecting said splitted part of said optical detection signal. The detector may be adapted for monitoring a shape of an illumination beam at said sample in said measurement reservoir. The detector may be a two-dimensional detector comprising a matrix of detector elements.

The optical control means may be adapted for controlling a position of any of said measurement reservoir, said detection unit or said illumination unit for at least partly correcting for a lateral misalignment.

The optical control means may be adapted for controlling a position of a focussing means to correct a focusing of said optical detection signal from the sample on said detection unit.

It is an advantage of particular embodiments of the present invention that at least partial correction for lateral misalignments may be performed. The controlling a position of a focussing means is adapted for correcting a shift in focus of said optical detection signal due to a shift of a surface of a sample fluid to be measured. It is an advantage of particular embodiments of the present invention that at least partial correction for a lensing effect of a sample fluid may be provided. The correction may be adapted for different shapes of the sample fluid surface generating the lensing effect.

The optical control means may provide a feed-back signal to the optical characterisation device. The feedback signal may allow for control of a position or operation of any of the illumination source, the detection unit, a substrate comprising the measurement reservoir or a focussing system.

The detection unit may be adapted for detecting at least two optical response signals, a first optical response signal corresponding with a known illumination beam path length in the material to be characterised and a second optical response signal corresponding with an unknown illumination beam path length in the material to be characterised, the known illumination beam path length being substantially larger than the unknown illumination beam path length, the optical characterisation device furthermore comprising a processing means for deriving the unknown illumination beam path length based on said at least two optical response signals and said known illumination beam path length.

The present invention also relates to a method for optical characterising a sample fluid, the method comprising illuminating a measurement reservoir adapted to be filled with sample fluid and filling said measurement reservoir with sample fluid in a filling direction, and during said illuminating and filling, detecting at a plurality of moments an optical detection signal from said sample fluid by illuminating the fluid in the at least one measurement reservoir along an optical axis substantially oriented along said filling direction.

The method furthermore may comprise deriving a characteristic of said sample fluid taking into account a shape of said measurement reservoir. At a plurality of moments during filling may mean for different fluid levels in the measurement reservoir.

Deriving a characteristic of said sample fluid taking into account a shape of said measurement reservoir may comprise deriving a variation in the behaviour of the optical detection signal as function of the filling, e.g. filling rate, of the measurement reservoir.

Deriving a variation in the behaviour of the optical detection signal as function of the filling may comprise deriving a variation in the rate of change of the optical detection signal as function of the filling, e.g. filling rate, of the measurement reservoir.

The method further may comprise subsequently filling sub-reservoirs of said measurement reservoir positioned subsequently along an illumination path in said measurement reservoir.

The method may comprise detecting an optical detection signal from the sample each time a sub-reservoir is filled.

The method furthermore may comprise detecting at least two optical detection signals comprising a first optical detection signal corresponding with a known illumination beam path length in the sample fluid and a second optical detection signal corresponding with an unknown illumination beam path length in the sample fluid, and deriving an unknown illumination beam path length based on the two optical detection signals and the known illumination beam path length in the sample fluid.

The method furthermore may comprise during said illuminating and filling, dissolving dissolvable material thus influencing the optical path length of the illumination beam in the fluid.

The present invention also relates to a controller for use in an optical characterisation device, the optical characterisation device comprising an illumination unit, a detection unit, a device for assisting in optical characterisation having a substrate with at least one measurement reservoir and a fluid providing means for filling the at least one measurement reservoir with the fluid in a filling direction, said detection unit being controlled for detecting optical detection signals from the fluid at a plurality of moments during the filling of said at least one measurement reservoir by illuminating the fluid in the at least one measurement reservoir along an optical axis substantially oriented along said filling direction, the controller being adapted for synchronising a filling of the least one measurement reservoir and a detecting by the detection unit.

The present invention also relates to a computer program product adapted for, when executed on a computing device, performing a method for optically characterising, the method comprising illuminating a measurement reservoir adapted to be filled with sample fluid and filling said measurement reservoir with sample fluid in a filling direction, and during said illuminating and filling, detecting at a plurality of moments an optical detection signal from said sample fluid by illuminating the fluid in the at least one measurement reservoir along an optical axis substantially oriented along said filling direction.

The present invention furthermore relates to a machine readable data storage device storing such a computer program product and/or the transmission of such a computer program product over a local or wide area telecommunications network.

It is an advantage of embodiments of the present invention that these are compatible with automated testing systems, such as high throughput systems.

The present invention also relates to a device for assisting in optical characterisation of a fluid, the device comprising a substrate with at least one measurement reservoir adapted for being filled with the fluid, wherein the device comprises at least one dissolvable material, the dissolvable material being adapted for providing information regarding the filling of the measurement reservoir. The at least one dissolvable material may be provided in the measurement reservoir. Alternatively, the at least one dissolvable material may for example be provided in another part of the device, e.g. an input channel or an intermediate channel between two sub-reservoirs of the measurement reservoir. The at least one dissolvable material may be adapted, e.g. in position, so as to provide information of the optical path length of the illumination beam in the fluid. The latter may be e.g. performed when the dissolvable material is contacted with the fluid. The measurement reservoir may be adapted for filling with the fluid in a filling direction and the device may be adapted for receiving an illumination beam for illuminating the fluid in the at least one measurement reservoir along an optical axis substantially oriented along said filling direction. The at least one dissolvable material may be adapted for varying the rate of change of an optical path length of the illumination beam in the fluid as function of the filling rate. The optical path length of the illumination beam in the fluid thereby may be defined as the product of the geometric distance and the refractive index, or in a medium of varying refractive index, the integral of the local refractive index along the optical path, represented by $$\int_{opticalpath} n\,ds$$

with ds an element of length along the path.

The measurement reservoir may comprise at least one dissolvable material at the top or bottom of the measurement chamber with respect to the filling direction.

The measurement reservoir may comprise measurement reservoir side walls, and the measurement reservoir may comprises at least one dissolvable material positioned on a measurement reservoir side wall between a top and bottom of the measurement reservoir with respect to the filling direction.

The dissolvable material may be adapted for, when being dissolved by contacting with the fluid, changing the absorption coefficient of the fluid.

The dissolvable material may provide a reaction with the sample that is measurable optically. The dissolvable material may comprise a colorant.

The dissolvable material may be provided as a dissolvable coating.

The at least one dissolvable material may cover at least part of a measurement reservoir side wall along the filling direction of the measurement reservoir. The latter may provide an increasing absorption coefficient of the fluid.

The at least one dissolvable material may be a plurality of dissolvable materials, each indicative of different information of the optical path length of the illumination beam in the fluid. The plurality of dissolvable materials may be positioned at different positions on the measurement reservoir wall along the filling direction of the measurement reservoir.

The present invention also relates to a corresponding method for optical characterising a sample fluid, the method comprising illuminating a measurement reservoir adapted to be filled with sample fluid and filling said measurement reservoir with sample fluid, the method comprising dissolving, in the device, dissolvable material for providing information regarding the filling of the measurement reservoir. The dissolving may be performed during filling of the measurement reservoir. Dissolving dissolvable material may be for influencing the optical path length of the illumination beam in the fluid.

It is an object of further aspects of the present invention to provide good devices for assisting in optical characterization of fluids and good apparatus and methods for optically characterizing fluids. It is an advantage of embodiments of the present invention that systems and methods are provided for performing accurate optical characterization of fluids. It is also an advantage of embodiments of the present invention that systems and methods are provided whereby accurate optical characterization may be performed, even during filling of a measurement reservoir with sample fluid.

These further objects and advantages are achieved by a device for assisting in optical characterisation of a liquid sample, the device comprising a substrate with at least one measurement reservoir adapted for being filled with said liquid sample and at least one gas collecting cavity adapted to collect gas, said measurement reservoir being adapted for irradiating said liquid sample in said measurement reservoir along an optical path for said optical characterisation of said liquid sample, and the at least one gas collecting cavity being positioned outside said optical path. It is an advantage that a substantial reduction of gas bubbles in the liquid sample to be measured may be obtained in particular embodiments of the present invention.

The at least one gas collecting cavity may be in direct contact with the at least one measurement reservoir. The gas collecting cavity in direct contact with the at least one measurement reservoir typically may mean that there is no interconnection channel between the gas collecting cavity and the measurement reservoir or in other words wherein the volume of the gas collecting cavity is in abutment with the volume of the measurement reservoir.

The measurement reservoir may be a liquid flow-through reservoir. A liquid flow-though reservoir typically may be a closed reservoir having an input channel for providing liquid and an output channel for removing liquid.

The at least one gas collecting cavity may be a ring shaped cavity. The ring shaped cavity may be any type of cavity around a central portion of substrate material, such as e.g. a torus-shaped cavity.

One of the at least one gas collecting cavity may be positioned at a side of the measurement reservoir which is positioned above the sample liquid when the measurement reservoir is filled with sample liquid.

One of the at least one cavity may be positioned at a side of the measurement reservoir which is positioned substantially below the sample liquid when the measurement reservoir is filled with sample liquid. The latter may be advantageous when e.g. the measurement reservoir is filled from the top and the measurement reservoir is filled fast.

The at least one cavity may have a cross-section perpendicular to a filling direction, with a cross-section area being substantially different from cross-section areas of cross-sections perpendicular to a filling direction in a remaining part of the measurement reservoir.

The substrate furthermore may comprise an input channel for providing liquid sample to the at least one measurement reservoir, the device comprising an overpressure releasing means connected to the input channel. The overpressure releasing means may be connected directly to the input channel. It may be an overpressure releasing channel.

The connection between the input channel and the overpressure releasing means may have a diameter adapted for avoiding air to be driven into the measurement reservoir, once the measurement reservoir is filled with sample fluid.

The device may comprise an output reservoir connected to the at least one measurement reservoir, wherein the overpressure releasing means has a flow resistance adapted to substantially prevent sample fluid to flow from the measurement reservoir to the output reservoir when filling the measurement reservoir. The filling of the measurement reservoir may be performed by providing an over pressure.

The invention also relates to an optical characterisation system, comprising an irradiation unit, a detection unit and a device for assisting optical characterisation of a liquid sample, the device for assisting comprising a substrate with at least one measurement reservoir adapted for being filled with said liquid sample and at least one gas collecting cavity adapted to collect gas, said measurement reservoir being adapted for irradiating said liquid sample in said measurement reservoir along an optical path for said optical characterisation of said liquid sample, and the at least one gas collecting cavity being positioned outside said optical path.

The invention also relates to a device for assisting in optical characterisation of sample fluid, the device comprising a substrate with at least one measurement reservoir, said measurement reservoir being adapted for irradiating said liquid sample in said measurement reservoir along an optical path for said optical characterisation of said liquid sample, the device furthermore comprising an input channel for providing liquid sample to the at least one measurement reservoir and an overpressure releasing means connected to the input channel. The overpressure releasing means may be connected directly to the input channel. It may be an overpressure releasing channel. The overpressure releasing means may be adapted to avoid air being driven into the measurement reservoir, after the input reservoir is emptied. The overpressure releasing means may be adapted such that sample liquid is rather driven to the measurement reservoir than through the overpressure releasing means, but that gasses escape more easily through the overpressure releasing means than through the measurement reservoir.

The connection between the input channel and the overpressure releasing means may have a diameter, shape or wall property adapted for preventing gas, from an emptied input reservoir, to flow spontaneously in the measurement reservoir.

The substrate may comprise an output reservoir connected to the at least one measurement reservoir, wherein the overpressure releasing means may have a flow resistance adapted to substantially prevent sample fluid to flow from the measurement reservoir to the output reservoir when filling the measurement reservoir. The filling of the measurement reservoir may be performed by providing an over pressure.

The present invention also relates to an optical characterisation system for characterising a sample fluid, the system comprising an irradiation unit, a detection unit and a device for assisting optical characterisation of a liquid sample as described above.

In another aspect, the present invention relates to an optical characterisation device for characterising samples, the device comprising an illumination unit for illuminating a sample in a measurement reservoir, a detection unit for detecting an optical detection signal from the sample and an optical control means for monitoring illumination properties of the illumination of the sample in the measurement reservoir.

It is an advantage of embodiments of the present aspect that methods and systems are provided allowing accurate optical characterisation of a sample.

The optical control means may comprise a means for splitting of part of said optical detection signal from the sample and a detector for detecting said split part of said optical detection signal.

The detector may be adapted for monitoring a shape of an illumination beam at said sample in said measurement reservoir. The detector may be a two-dimensional detector comprising a matrix of detector elements or a position sensitive detector surface.

The optical control means may be adapted for controlling a position of any of said measurement reservoir, said detection unit or said illumination unit for at least partly correcting for a lateral misalignment.

The optical control means may be adapted for controlling a position of a focussing means to correct a focusing of said optical detection signal from the sample on said detection unit. It is an advantage of particular embodiments of the present invention that at least partial correction for lateral misalignments may be performed.

The optical control means may be adapted for providing information about a focussing and/or alignment error, the information being adapted to allow good interpretation of a read-out signal of the optical characterisation system.

The optical control means may be adapted for providing information about a focussing and/or alignment error to an evaluation means of the optical characterisation system for correcting a read-out signal of the optical characterisation system.

The controlling a position of a focussing means may be adapted for correcting a shift in focus of said optical detection signal due to a shift of a surface of a sample fluid to be measured. It is an advantage of particular embodiments of the present invention that at least partial correction for a lensing effect of the free surface of the sample fluid, e.g. due to surface tension, may be provided. The correction may be adapted for different shapes of the sample fluid surface generating the lensing effect or adapted for different values of the contact angle of the fluid sample with the substrate material.

The optical control means may provide a feed-back signal for controlling a position or operation of any of the illumination source, the detection unit, a substrate comprising the measurement reservoir or a focussing system.

In another aspect, the present invention also relates to a method for optical characterising material, the method comprising detecting at least two optical detection signals comprising a first optical detection signal corresponding with a known illumination beam path length in the sample fluid and a second optical detection signal corresponding with an unknown illumination beam path length in the sample fluid, and deriving an unknown illumination beam path length based on the two optical detection signals and the known illumination beam path length in the sample fluid.

In another aspect, the present invention also relates to an optical characterisation device for optical characterising material, the device comprising an illumination unit for generating an illumination beam for illuminating the material to be characterised and a detection unit for detecting an optical response signal from the illuminated material to be characterised, wherein the detection unit is adapted for detecting at least two optical response signals, a first optical response signal corresponding with a known illumination beam path length in the material to be characterised and a second optical response signal corresponding with an unknown illumination beam path length in the material to be characterised, the known illumination beam path length being substantially larger than the unknown illumination beam path length, the optical characterisation device furthermore comprising a processing means for deriving the unknown illumination beam path length based on said at least two optical response signals and said known illumination beam path length.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The teachings of the present invention permit the design of improved methods and apparatus for optically characterising fluids. The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIG. 3a to FIG. 3c and FIG. 4a to FIG. 4e show top views of different configurations of a number of exemplary devices for assisting in optical characterisation according to embodiments of the first aspect of the present invention.

FIG. 5b shows an optical detection signal as function of time when using a continuous flow and using a device as described in FIG. 5a.

FIG. 6b shows an optical detection signal as function of time when using a continuous flow and using a device as described in FIG. 6a.

Figure 1:
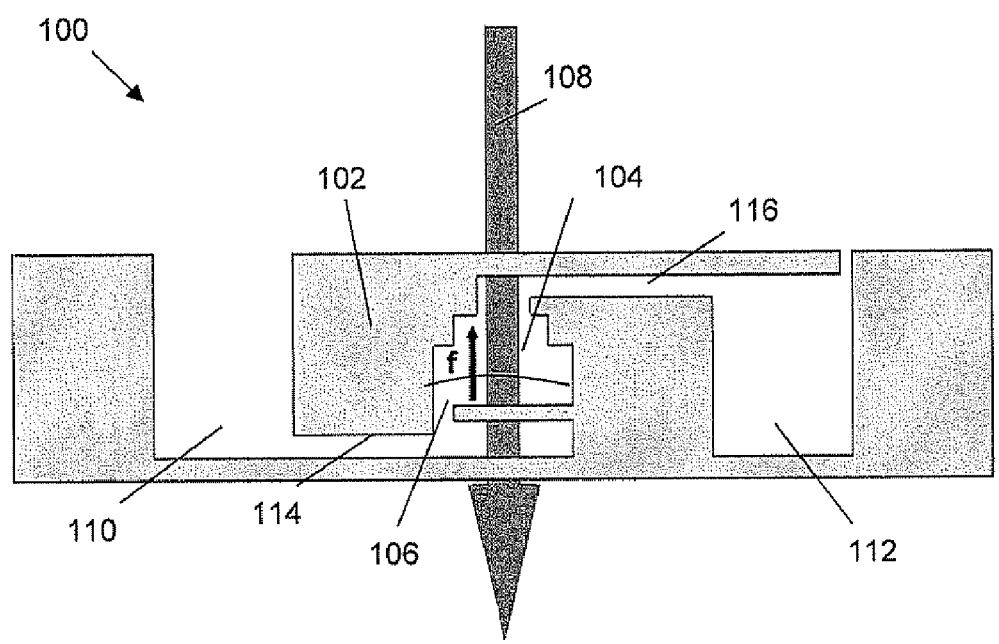
FIG. 1 is a schematic overview of a device for assisting in optical characterisation according to embodiments of a first aspect of the present invention.

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first and second and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

The following terms are provided solely to aid in the understanding of the invention. These definitions should not be construed to have a scope less than understood by a person of ordinary skill in the art.

With the terms "illumination" and "optical", at least UV, visible or infrared radiation are meant although the invention is not limited thereto and other types of electromagnetic illumination could also be used. With the term "transparent" there is meant that the illumination or optical detection signal substantially is transmitted through the object.

With the terms "hydrophilic" and "hydrophobic" there is meant the degree in which material attract respectively repel water-based fluids. Nevertheless, the invention is not limited thereto and where "hydrophilic" and "hydrophobic" is used, also "lyophilic" respectively "lyophobic" may be used, indicating the degree in which material attract respectively repel fluids more in general.

An "optical response" or "optical detection signal" from a sample fluid thereby may be either the transmitted or reflected portion of an illumination beam after interaction with the sample fluid, which for example allows to see a change in intensity and or spectral behaviour due to absorption by the sample fluid or particular analytes therein. Alternatively or in addition thereto, the term "optical response" or "optical detection signal" from a sample fluid also may be a luminescence response, such as e.g. a fluorescence response, of a sample fluid or particular, optionally labelled, analytes therein as response to illumination of the sample fluid with the illumination beam. Labelling of analytes may be performed to detect presence of predetermined analytes by providing labels to these analytes, e.g. radiative labels or fluorescent labels although the invention is not limited thereto. Such labels may be attached to the analytes directly or indirectly.

Optical characterisation of the sample fluid may comprise optical characterisation of sample fluids as such or characterisation of specific analytes present in the sample fluid, such as e.g. proteins, antibodies, nucleic acids (e.g. DNA, RNA), peptides, oligo- or polysaccharides or sugars, small molecules, hormones, drugs, metabolites, cells or cell fractions, tissue fractions, specific chemical components, etc. The latter may be detected in an original sample fluid, or the sample fluid may already have been processed, such as filtered, dissolved into a buffer, chemically or biochemically modified, diluted, etc. The sample fluids may be e.g. biological fluids, environmental fluids, research fluids, fluids comprising solid sample material, etc.

Where reference is made to a bottom side of a measurement reservoir, reference is made to that side of the measurement reservoir that sample fluid is drawn to by gravity, when the device is positioned to be in use.

Typically the sample fluid may be a sample liquid.

In a first aspect, the present invention relates to a device for assisting in optical characterisation of a fluid. Such a device may comprise a substrate and a measurement reservoir adapted to be filled with the fluid to be characterised. Such a device may thus comprise structures for holding sample fluids, e.g. liquid samples, and therefor may comprise a combination of channels and measurement reservoirs for providing and holding sample fluids. The device according to the embodiments of the first aspect of the present invention can allow for performing optical measurements on the sample fluid, whereby the optical path length of an illumination beam through the sample can be adjusted or varied. The varying may be a continuously varying, e.g. by illuminating the sample fluid and detecting a response thereof during a continuous filling of the measurement reservoir. The device therefore may be used in optical characterisation systems whereby optical measurements will be performed during filling of the at least one measurement reservoir with fluid. According to embodiments of the first aspect of the present invention, the device is adapted for receiving an illumination beam for illuminating the fluid in the at least one measurement reservoir. The illuminating may be illuminating substantially in the same sense as the filling of the measurement reservoir or in opposite sense. The at least one measurement reservoir furthermore is adapted for varying the rate of change of the optical path length of the illumination beam in the fluid, the measurement reservoir being adapted for providing information of an optical path length of the illumination beam in the fluid at a plurality of moments during the filling with the fluid. A measurement reservoir adapted for varying the rate of change of the optical path length of the illumination beam in the fluid, typically can be obtained in a number of ways. The measurement reservoir shape may for example comprise a variation in cross-section perpendicular to the filling direction of the measurement reservoir. Alternatively or in addition thereto, different parts of the walls of the measurement reservoirs may have different hydrophobic/hydrophilic properties such that in different parts of the measurement reservoir, a different resistance occurs to the filling, resulting in a different filling rate. These examples, the invention not being limited thereto will be discussed in more detail in the different embodiments. The fluid samples, e.g. liquid samples, to be measured can be small samples, with a volume down to 1 µl, down to 1 nanoliter or even less, depending on the sensitivity that needs to be obtained, the absorption/excitation characteristics of the fluid, and the dimensions of the measurement reservoir. For example, if a measurement reservoir with a footprint of only 0.007 mm$^2$ is used and a measurement can be performed with a maximum column height of 0.1 mm, less than 1 nanoliter is needed. The measurement reservoir height typically may be between 0.1 mm and 2 mm, although the invention is not limited thereto. Optionally, the at least one measurement reservoir may have a diameter down to in the order of 1 mm, or down to in the order of 0.1 mm or even smaller, thus allowing to measure the characteristics of sample volumes of a nanoliter or smaller, thus imposing less stringent requirements of the amount of fluid that needs to be present than e.g. when using standard cuvettes.

By way of illustration, a device for assisting in optical characterisation of a fluid according to the first aspect of the present invention is shown in FIG. 1 by way of example, the invention not being limited thereto. The different standard and optional components of the exemplary device 100 will be discussed in more detail below.

The device 100 may comprise a substrate 102 and at least one measurement reservoir 104 in the substrate. The device 100 thereby may comprise a specific arrangement of microfluid measurement reservoirs 104 that can be filled. The substrate 102 and the at least one measurement reservoir 104 may for example be realised by bonding two or more microstructured plates, where at least the part where the optical path passes is optically transparent. The latter means that the material is transparent for the wavelength(s) of the illumination beam used for the optical characterisation. The substrate 102 correspondingly can be made from any suitable material such as for example a polymer, metallic material or glass material, optionally from combined transparent and non-transparent materials. The device may be made from different plates which may be positioned with respect to each other and which may be sealed, e.g. by bonding the materials for example by using adhesive or e.g. by using flexible rings, thus avoiding leakage. If external pressure is to be applied to an input reservoir, typically materials also may be sealed using e.g. a tube, e.g. rubber ring, terminated in a connector put onto such an input reservoir. Providing structuring of the device 100 in order to e.g. generate at least one measurement reservoir 104 may be performed by e.g. moulding, embossing, etching, ablation, milling or drilling. In some embodiments, the surfaces of the at least one measurement reservoir 104 and/or microfluid channels leading thereto and/or therefrom may be adjusted to have a predetermined hydrophobic or hydrophilic behavior, different from the bare material properties. This can be achieved by any suitable means, such as for example by selection of materials used for the substrate, by chemical treatment or plasma exposure of measurement reservoir walls, e.g. by $O_2$ plasma treatment.

The at least one measurement reservoir 104 in the substrate 102 can be adapted for filling with the sample fluid 106. Filling can occur in a filling direction, as indicated by way of example by arrow f in FIG. 1. The filling direction thereby is the direction that is substantially perpendicular to the top surface or average plane through the top surface of the sample fluid in the measurement reservoir. Preferably at least part of the at least one measurement reservoir 104 is adapted for receiving an illumination beam 108, such that at least part of the sample fluid 106 in the at least one measurement reservoir 104 is illuminated. In embodiments according to the present invention, the measurement reservoir is adapted for varying the rate of change of the optical path length of the illumination beam in the fluid. The measurement reservoir may be adapted for varying the rate of change of an optical path length of the illumination beam in the fluid, for a constant input pressure or for a constant input volumetric flow of the fluid, although the invention is not limited thereto. Variations in the input pressure or input volumetric flow in the measurement reservoir not caused by the measurement reservoir may be taken into account for obtaining measurement results. The measurement reservoir can be adapted in a number of ways.

Figure 2A:
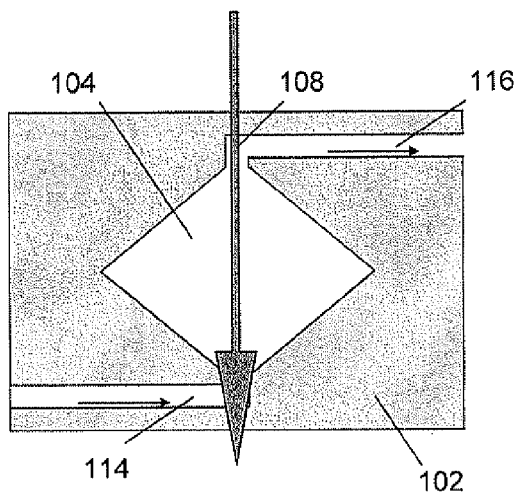
FIG. 2a to FIG. 2e show vertical cross-sections of a number of exemplary devices for assisting in optical characterisation according to embodiments of the first aspect of the present invention.
Figure 2B:
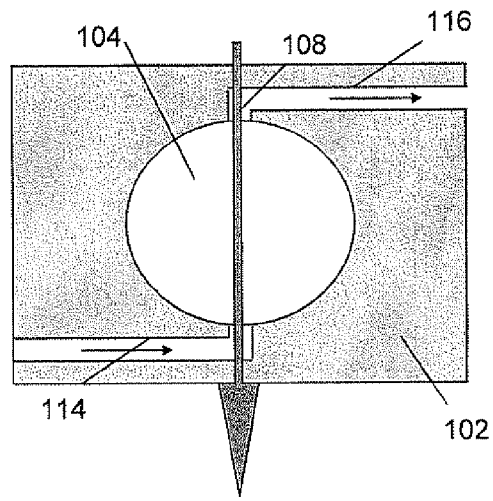
Figure 2C:
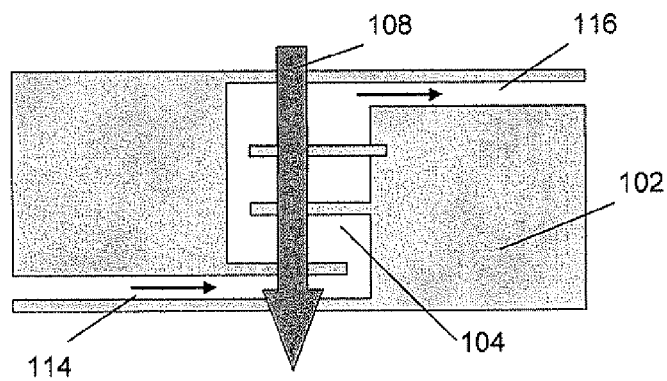
Figure 2D:
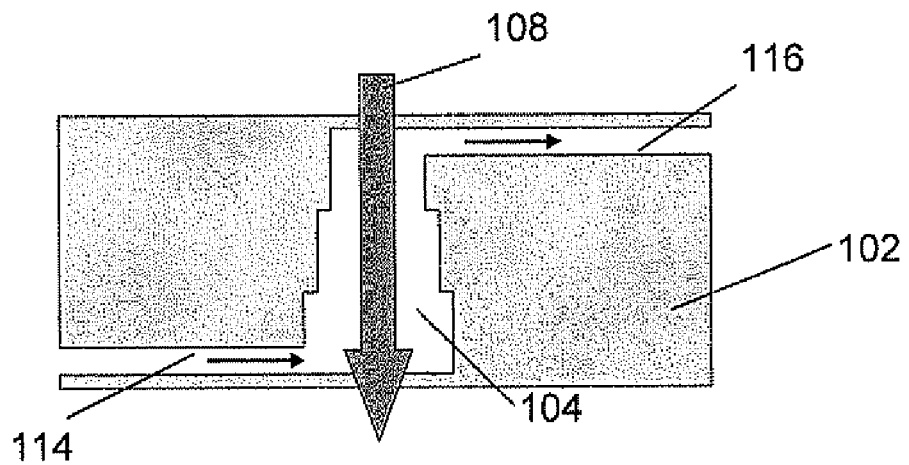

In a first exemplary way, the measurement reservoir shape may be adapted for providing information of an optical path length of the illumination beam in the sample fluid 106 at a plurality of moments during the filling with the sample fluid 106. The measurement reservoir 104 has a measurement reservoir shape comprising a variation in cross-section perpendicular to a filling direction. In preferred embodiments, this variation of cross-section may comprise at least one discontinuity in cross-section perpendicular to a filling direction. The latter allows to increase the accuracy of the measurements. The measurement reservoir shape thereby may be adapted such that it influences the behaviour of an optical detection signal as function of the filling, during the filling of the measurement reservoir with sample fluid 106. Influencing the behaviour may comprise influencing the rate of change of the optical detection signal as function of the filling. Preferably, the device may be adapted for receiving the illumination beam 108 for illuminating at least part of the sample fluid 106 along an optical axis that is substantially oriented along the filling direction. With substantially oriented along the filling direction there may be meant that the optical axis crosses the different cross-sections of the measurement reservoir 104, the different cross-sections being perpendicular to the filling direction in the measurement reservoir 104. The at least one measurement reservoir may e.g. have stair-case shaped walls, may have a serpentine shape, etc. A number of different measurement reservoir shapes are indicated in cross-section by way of illustration in FIG. 2a, 2b, 2c and 2d, the invention not being limited thereto. In FIG. 2a and FIG. 2b two embodiments are shown wherein no discontinuity occurs for cross-sections along the filling direction, whereas in FIG. 2c an FIG. 2d two embodiments are shown wherein a discontinuity occurs for cross-sections along the filling direction. It is beneficial to give the bottom part of the measurement reservoir 104 the largest diameter. This implies that the sample fluid level, and correspondingly the optical path length, raises slowest at the beginning of the filling. For liquid samples with a large absorption or high excitation power, a slower increase of the sample height allows for more appropriate measurement results. Typically, the amount of absorption that can be measured is determined by the detection limit of the detection system used and the height of the sample liquid the illumination beam needs to pass through. At slower filling rates, the time that a fluid level remains more or less constant is substantially longer, resulting in a reduction of the relative error made on the fluid height by measuring during filling of the measurement reservoir. Furthermore the larger the diameter of the measurement reservoir, the less meniscus effects occur, which also results in reduction of the relative error made on the fluid height.

Figure 2E:
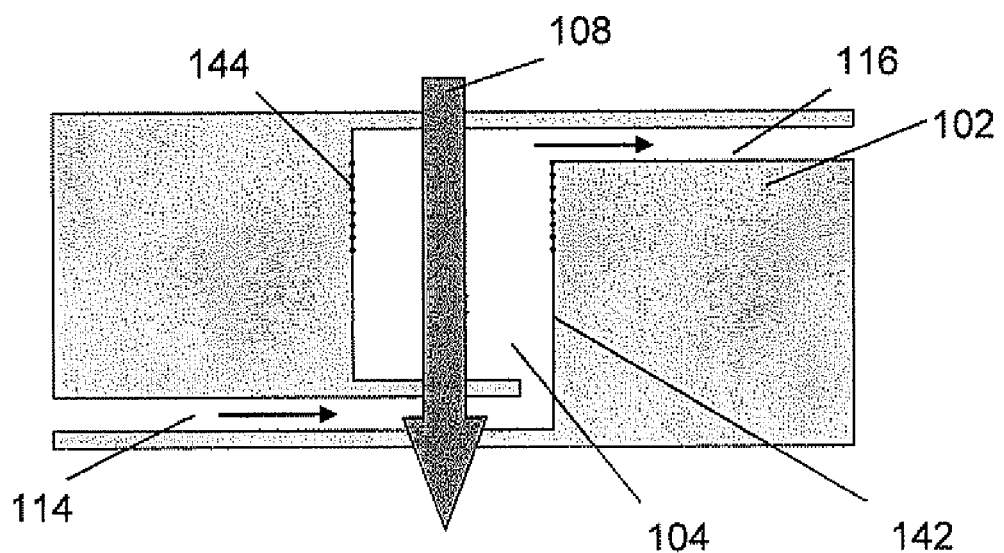

In a second exemplary way, the properties of the measurement reservoir walls may be adapted such that different parts of the measurement reservoir provide a different interaction with the sample fluid, thus resulting in a different filling rate or an influence of a predetermined flow rate. The latter typically may be obtained by selecting different hydrophilic/hydrophobic properties to different parts of the measurement reservoir surfaces. By way of illustration, an exemplary measurement reservoir comprising measurement reservoir walls with different properties is schematically illustrated in FIG. 2e. Surfaces 142, 144 with different hydrophilic behaviour, and thus different hydrophobic behaviour, are provided. Under e.g. capillary filling conditions or when an input pressure is applied for filling the fluid in the measurement reservoir, fluid typically will rise at different speeds through the part of the measurement reservoir 104 having surface 142 and the part of the measurement reservoir 104 having surface 144. Inducing such different surface properties may e.g. be performed by selecting different materials for constituting the measurement reservoir walls in the different parts or by treating the surface of the measurement reservoir walls differently in different parts, e.g. by exposing one part to an oxygen plasma treatment while not exposing another part. Typically, surfaces exposed to an oxygen plasma treatment may be more hydrophilic. The latter typically may result in the presence of a different contact angle between the measurement wall surface and the sample fluid.

In general, the measurement reservoir thus is adapted, e.g. by shape or hydrophilic properties or a combination thereof, for making the filling rate of the fluid variable during filling.

Figure 3C:
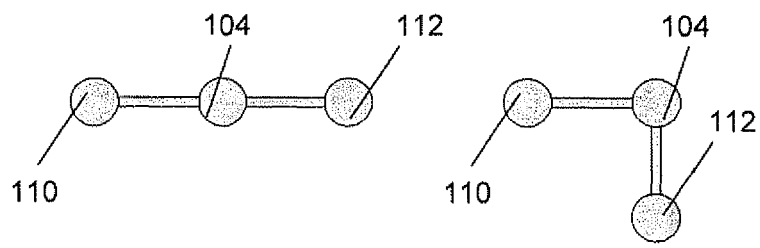
Figure 3C:
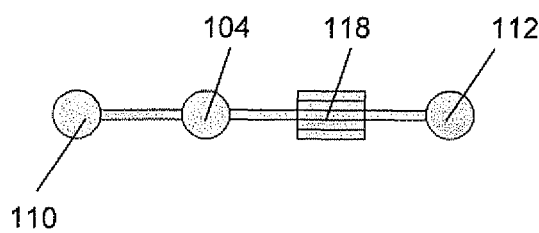

Preferably, in order to be able to fill the measurement reservoir 104, an input reservoir 110 and an output reservoir 112 may be provided, as well as channels 114, 116 for bringing the sample fluid to and from the at least one measurement reservoir 104. Alternatively the input reservoir 110 and the output reservoir 112 may be avoided and the fluid injection may take place directly in the measurement reservoir. Preferably, the at least one measurement reservoir 104 is filled from the bottom side through the input microfluidic channel 114. The position of the input reservoir 110, the at least one measurement reservoir 104 and the output reservoir 112 can be chosen depending on the external conditions. The latter is illustrated in FIG. 3a and FIG. 3b in top view. Furthermore, one or more optional test structures may be provided for checking for the presence of sample fluid or for measuring the flow rate. Preferably a number of test structures are used, whereby the position and distance between test structures may allow to obtain appropriate information about the sample fluid. A device incorporating a test structure 118 on the fluid path is shown in FIG. 3c in top view.

Figure 4C:
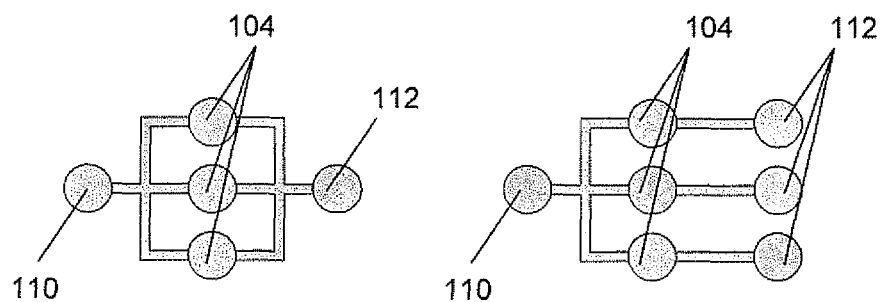
Figure 4C:
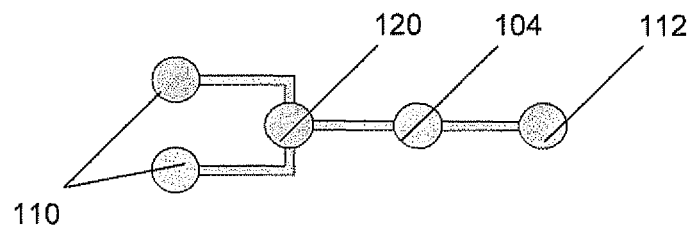
Figure 4D:
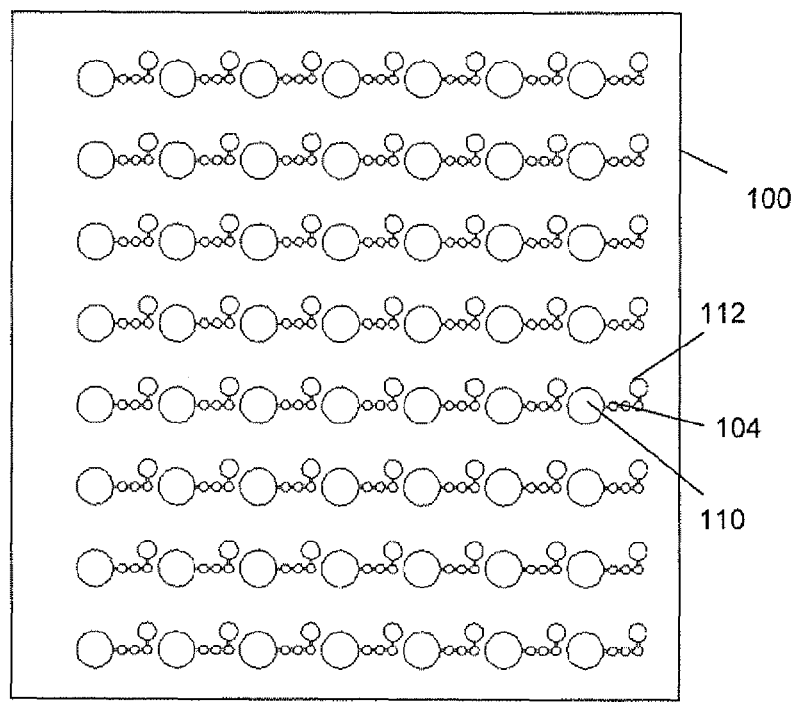
Figure 4E:
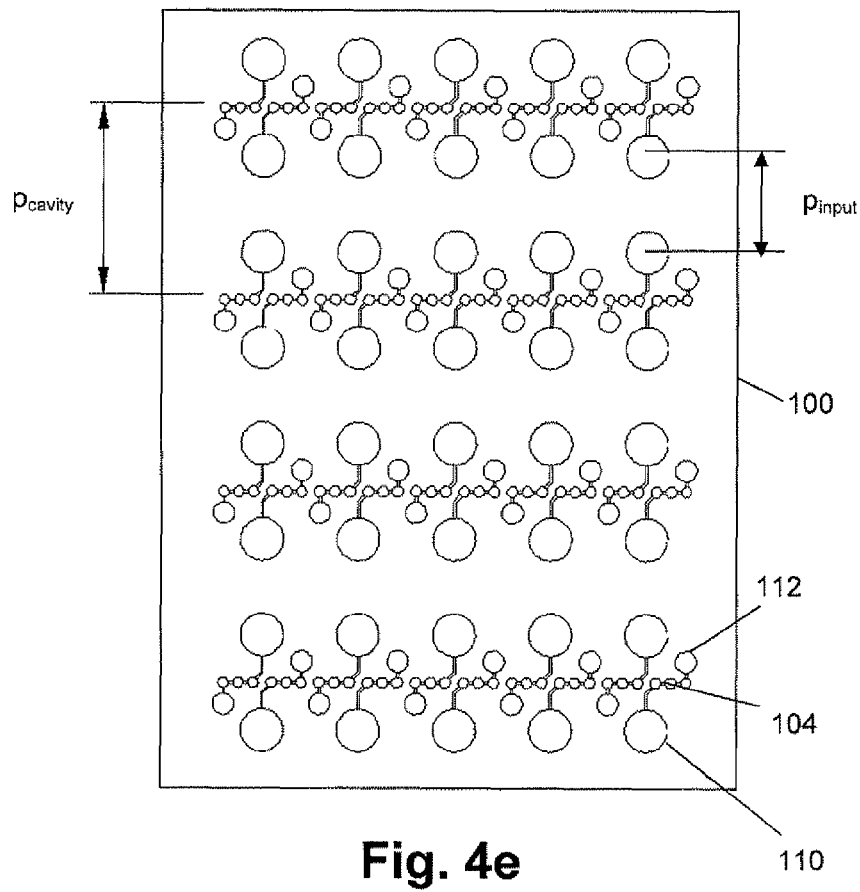

In particular embodiments according to the first aspect, the present invention comprises a device 100 for assisting in optical detection as described above, wherein a plurality of structures, comprising a measurement reservoir and an input and output for the sample fluid to the measurement reservoir, are incorporated in the device. The plurality of structures may be for example a mixture of differently shaped structures, a number of structures having a fixed shape and fixed size, or a number of structures having a fixed shape but different size. The structures can be organised in one or two-dimensional arrays. It might be beneficial to put, if present, input containers on a pitch according to predetermined standards, such as e.g. the Society for Biomolecular Screening standards. Furthermore, one input reservoir 110 may be connected to a multitude of measurement reservoirs 104. In FIG. 4a, FIG. 4b, FIG. 4c top views of different structures are shown and in FIG. 4d and FIG. 4e top views of devices incorporating a number of exemplary-structures are shown. FIG. 4a illustrates a structure with a common input reservoir 110, two measurement reservoirs 104 in parallel and a common output reservoir 112. FIG. 4b illustrates a similar structure but with two output reservoirs 112. FIG. 4c illustrates a structure with a multitude of input reservoirs 110 connected to a mixing reservoir 120, which can be guided to one or more measurement reservoirs 104 and output reservoirs 112. FIG. 4d and FIG. 4e provide different designs of a plurality of structures in a device 100. FIG. 4d the pitch $p_{measurement\ reservoir}$ of measurement reservoirs 104 is the same as the pitch $p_{input}$ of the input reservoirs 110. The pitch $p_{measurement\ reservoir}$ thereby is defined as the distance between measurement reservoirs connected to neighbouring input reservoirs, i.e. not measurements reservoirs connected to the same input reservoir. In FIG. 4e the pitch of the measurement reservoirs 104 is half of the pitch of the input reservoirs 110.

A device 100 with a structure or structures as described above or a mixture thereof may be disposable or not. Such devices may be also integrated on a carrier that is disposable or not. The sample fluid may enter into the device via flexible connections, the device being adapted for receiving such flexible connections. Disposable as well as non-disposable devices or carriers may be adapted to be read out by a re-usable reader device and/or adapted to be illuminated by a re-usable illumination source. The device for assisting in optical characterisation of sample fluids or the carrier may be provided with alignment features, e.g. a reference to define the location of the measurement containers. Optionally, also a unique identification reference may be provided, such as e.g. a bar code.

The device may furthermore comprise a stop-filling structure and the measurement reservoir may be adapted with a bubble-reduction means, such as a ring structure, in order to achieve reduction of bubbles during the filling of the measurement reservoir 104 as will be described further in this application.

By way of illustration, the invention not being limited thereto, the first aspect will be further illustrated by way of a detailed description of several embodiments of the invention. It is clear that other embodiments of the invention can be configured according to the knowledge of persons skilled in the art without departing from the true spirit or technical teaching of the invention, the invention being limited only by the terms of the appended claims.

Figure 5A:
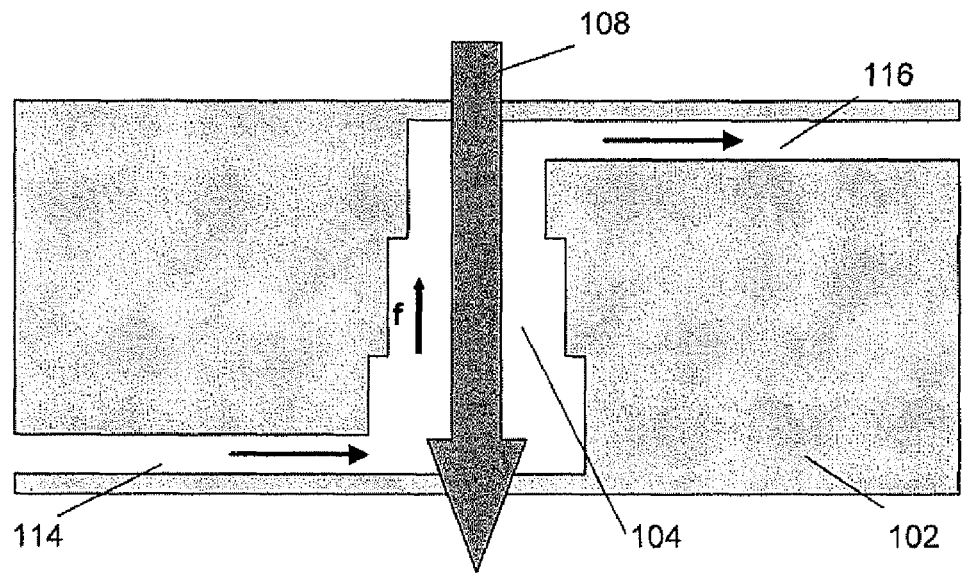
FIG. 5a shows a vertical cross-section of an exemplary device for assisting in optical characterisation having a staircase shaped measurement reservoir wall according to a first embodiment of the first aspect of the present invention.
Figure 5B:
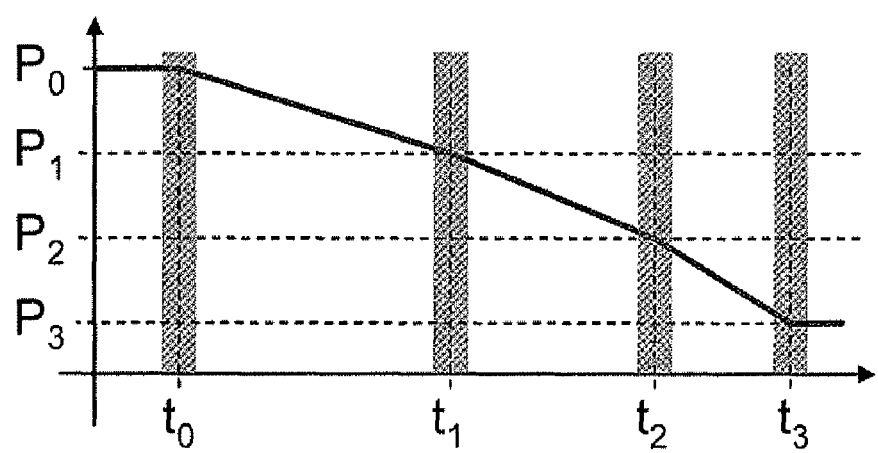

In a first embodiment according to the first aspect, the present invention relates to a device for assisting in optical characterisation of a fluid as described above, comprising the same advantages as described above, wherein the measurement reservoir comprises a measurement reservoir shape such that different cross-sections in a direction perpendicular to the filling direction are present and wherein a large interaction path of the probing beam with the fluid sample is present. The latter is obtained by a measurement reservoir shape wherein each of the cross-sections is adapted for crossing the optical path of an illumination beam used for characterising a fluid. The high overlap with the illumination beam may, for example, be suitable for sample fluids with a small amount of analytes to be detected, as the higher possibility to interact with the sample fluid may lead to an increased detection level. An example of such a structure is illustrated in FIG. 5a, whereas the resulting optical detection signal for a constant filling rate is shown in FIG. 5b. It is to be noted that, for continuous filling or for stepwise filling during filling periods, variations in the filling rate are not preferred, although small variations can be filtered out during signal processing and will not substantially influence the obtained results. Nevertheless, the system also may be used in optical characterisation systems with varying filling rate. The varying filling rate may be a predetermined filling rate, i.e. the filling rate may vary but whereby the variation of the filling rate is known or can be measured at each moment. By considering the rate of change of the optical detected signal as function of the filling, and looking at variations therein, the effect of the actual filling rate is filtered out. Typical small variations of the filling rate may be present due to small, e.g. unwanted, irregularities at the walls. For the ease, the following example is explained for a fixed filling rate. The exemplary device 100 shown in FIG. 5a comprises a measurement reservoir 104, an input channel 114, optionally at the bottom side, and output channel 116 at the top side. The input channel also may be positioned at a different position in the measurement reservoir. The device 100 can be adapted for aligning with the illumination source such that the illumination path is parallel to the central axis of a vertically-oriented reservoir. In other words, in view of gravity and forces exerted on the fluid by the walls, the filling direction can be perpendicular to the average fluid surface in the measurement reservoir during filling. The filling direction is indicated in FIG. 5a by arrow f. The illumination beam may be parallel to the filling direction f. In the present embodiment, the reservoir has a cross-section that varies along the filling direction and thus along the direction of the illumination beam, as the filling direction and the direction of the illumination beam are not perpendicular in the measurement reservoir. The variation of the cross-section may be either a continuous variation or a discrete variation, also referred to as discontinuous variation. Such a discrete variation may for example be a staircase variation as shown in FIG. 5a.

When the measurement reservoir is filled with a constant flow, the filling speed of the fluid in the measurement reservoir, i.e. the speed at which the top level of the sample fluid raises and consequently the speed at which the optical path length of an illumination beam in the sample fluid increases, varies with variation of the cross-section of the measurement reservoir 104 perpendicular to the filling direction f. Measurement of the change in optical response of the sample fluid to an illumination beam 108 during filling thus provides information on the fluid column height $h_{OPL}$ and in other words of the optical path length $h_{OPL}$ of an illumination beam in the sample fluid 106, as the path length can be derived from the variations in the behaviour of the optical detection signal as function of the filling. The latter is illustrated in FIG. 5b, wherein the measured optical detection signal as function of time is shown, corresponding with the measured optical detection signal as function of volume of sample fluid 106 in the measurement reservoir 104 in the present example as a constant flow is supposed. The shown results are transmission results of the illumination beam, indicating absorbance by analytes in the sample fluid 106. At $t_0$ the transmission starts to reduce as the measurement reservoir 104 starts to get filled and the optical path length of an illumination beam 108 in the sample fluid 106 increases. The speed at which this optical detection signal changes with time changes at $t_1$ and $t_2$ as the cross-section varies at these moments. From these results, the optical path length for the optical detection signal at moments $t_1$ and $t_2$ are known from the shape of the measurement reservoir, and the corresponding information is provided via measurement of the optical detection signal during filling. This information may e.g. be used in the signal processing, allowing for example interpolation of the optical path length for intermediate measurements, etc. Measuring during the filling of the measurement reservoir 104 allows to obtain a variable path length during the filling. The discontinuity in the optical detection signal, induced by the measurement reservoir shape, is an indication for the height of the liquid in the measurement reservoir 104 and allows to calculate the optical path length. The filling of the measurement reservoir 104 by the sample fluid may be done continuously or in steps. When the filling of the measurement reservoir 104 is done in steps, the height of the liquid may be constant during the optical measurements, which may lead to a better accuracy. It is at least preferred that the variation of the height of the liquid is substantially smaller than the variation of the cross-section of the structure during the optical measurements. The measurement speed may depend, for instance, on the type of read-out equipment used for the optical measurement.

Figure 5C:
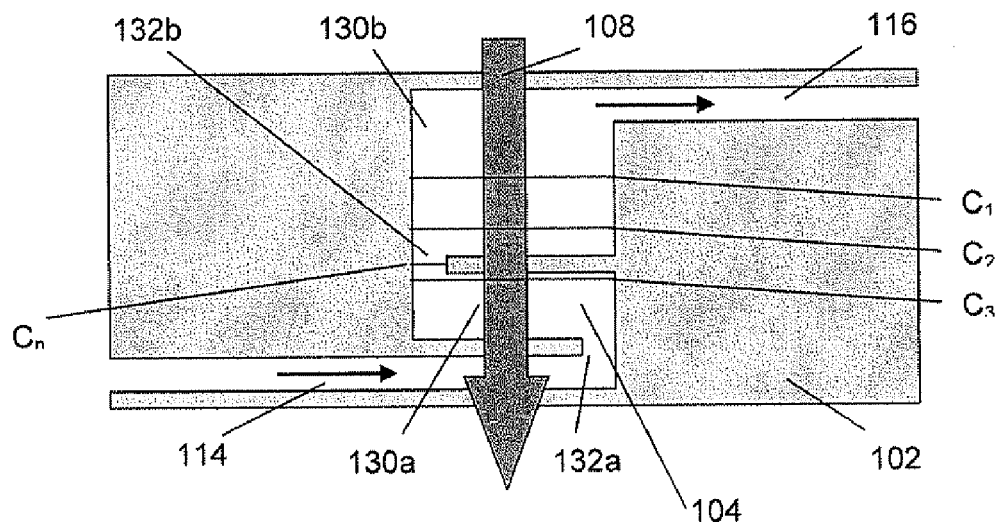
FIG. 5c and FIG. 5e show vertical cross-sections of exemplary devices for assisting in optical characterisation having a serpentine shaped measurement reservoir according to a second embodiment of the first aspect of the present invention.
Figure 5D:
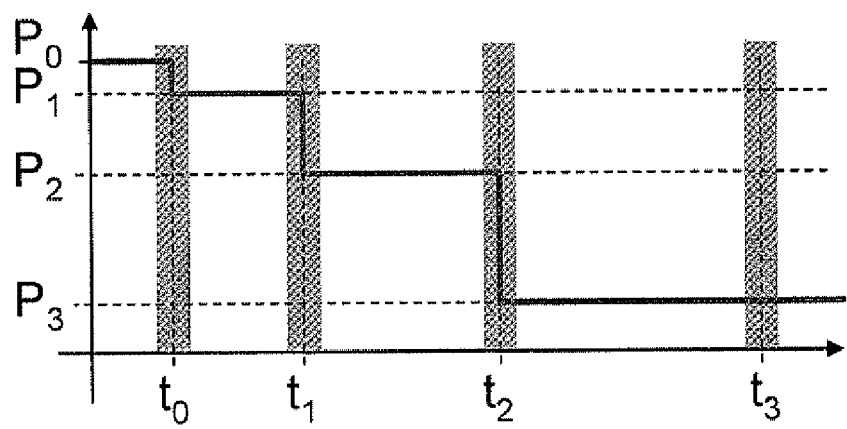
FIG. 5d shows an optical detection signal as function of time when using a stepwise flow rate and using a device as described in FIG. 5c.
Figure 5E:
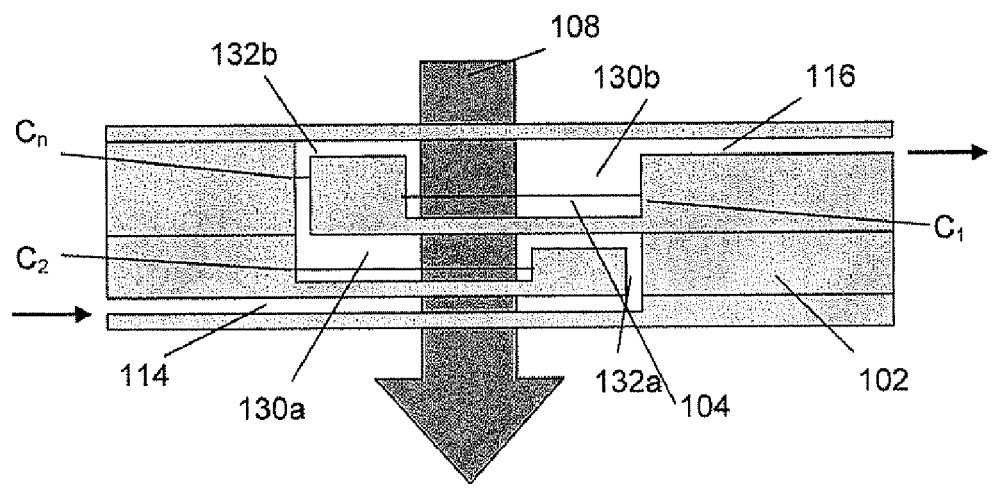

In a second embodiment according to the first aspect, the present invention relates to a device for assisting in optical characterisation of a fluid as described above, wherein the measurement reservoir comprises a measurement reservoir shape such that at least one cross-section of the measurement reservoir in the direction perpendicular to the filling direction does not cross the illumination path. In other words, there may be an intermediate cross-section of the measurement reservoir in the direction perpendicular to the filling direction, that is not in the optical path of the illumination beam. An example of such a structure is illustrated in FIG. 5c and FIG. 5e, whereas the resulting optical detection signal for a stepwise filled measurement reservoir 104 for a measurement reservoir shape as described in FIG. 5c is shown in FIG. 5d. For the ease, the following example is explained for a fixed filling rate. The device 100 comprises at least one measurement reservoir 104 comprising a number of sub-reservoirs 130a, 130b and a number of interconnection channels 132a, 132b, .... The sub-reservoirs 130a, 130b are positioned in the measurement reservoir 104 on top of each other so that an optical path of an illumination beam passes through these sub-reservoirs 130a, 130b when the measurement reservoir 104 is illuminated. The sub-reservoirs 130a, 130b may have a different height. Due to the presence of the sub-reservoirs 130a, 130b and the presence of interconnection channels 132a, 132b in between them not being in the optical path of an illumination beam when the measurement reservoir 104 is illuminated, the measurement reservoir is shaped such that there exist intermediate cross-sections perpendicular to the filling direction which are not in the optical path of an illumination beam illuminating the measurement reservoir 104. The input channel 114 also may be outside the optical path of an illuminating beam illuminating the measurement reservoir 104, such that no interconnection channel 132a is needed and only interconnection channel 132b remains. Optical detection can be performed during filling of the measurement reservoir 104, e.g. during continuous filling or after each sub-reservoir 130a, 130b is filled. Stepwise filling can e.g. be accomplished by selecting a predetermined size of the interconnection channels 132a, 132b, . . . between the measurement sub-reservoirs 130a, 130b, . . . and controlling the pressure on the inlet. At a given pressure at the inlet side, the diameter of the interconnection channel connecting the first and second sub-reservoir can be designed small enough to stop the fluid from entering the second sub-reservoir. Filling control then is realised by stepwise controlling the pressure at the inlet size. As smaller holes typically require a higher fluid pressure, e.g. the first interconnection channel may be selected larger than the second interconnection channel. In such a case, filling control may be realised by stepwise increasing the inlet pressure. Besides size of the interconnection channels 132a, 132b, also other properties, such as e.g. hydrophobic/hydrophylic properties of the walls of the interconnection channels can be controlled to control the filling of the sub-reservoirs. More generally, the fluid resistance properties of the interconnection channels with respect to an incoming flow may be selected such that filling control of the sub-reservoirs can be actively controlled by controlling the pressure at the inlet size.

A schematic representation of a typical optical detection result as obtained for a stepwise filled measurement reservoir 104 and using a measurement reservoir 104 shape as shown in FIG. 5c is illustrated in FIG. 5d. Time indications $t_0$, $t_1$, $t_2$ and $t_3$ indicate moments during which filling of the measurement reservoir 104 is performed, whereas in between these moments, the optical detection signal is constant as there is no variation in sample fluid level and thus no variation in optical path length. By way of example, the results for an absorption experiment are shown, the invention not being limited thereto. Prior to $t_0$ no fluid is present in the input channel 114 and the full intensity of the illumination beam is detected. It is to be noted that the absorption losses due to the substrate 102 and other losses outside the device 100 are neglected as well as the change in Fresnel reflections after filling, whereas in practice these can be taken into account, e.g. by performing a reference measurement for an empty device 100. At $t_0$ the input channel 114 is filled and between $t_0$ and $t_1$ the sample fluid surface is located in the interconnection channel 132a. The latter results in a constant optical detection signal between $t_0$ and $t_1$, whereby the optical path length for the corresponding optical detection signal is provided, i.e. can be determined, from the shape of the measurement reservoir 104, i.e. by the input channel 114. At $t_1$ the sub-reservoir 130a is filled and between $t_1$ and $t_2$ the sample fluid surface is located in the interconnection channel 132b, resulting in a constant optical detection signal between $t_1$ and $t_2$, the optical path length for the corresponding optical detection signal again being provided by the shape of the measurement reservoir 104, i.e. by the input channel 114 and the sub-reservoir 130a. At $t_2$, the sub-reservoir 130b is filled and after $t_2$ the sample fluid surface is fixed as the measurement reservoir 104 is completely filled. The optical detection signal then is based on absorption in the different sub-reservoirs 130a, 130b and the input channel 114, whereas the optical path length for the corresponding optical detection signal again is provided by the shape of the measurement reservoir 104, i.e. by the input channel 114 and the sub-reservoir 130a. In order to allow optical characterisation with a large absorption coefficient or with a high excitation efficiency, the reservoir with the smallest height may be filled first. The material between the sub-reservoirs 130a, 130b may be chosen to minimise the Fresnel reflections between the sample fluid/device interface. In a number of typical applications, the invention not being limited thereto, the sample fluid 106 may be water with additives, and its refractive index is close to 1.33. Good candidates for the interface materials may then be e.g. Teflon.

During the filling of the interconnection channels 132a, 132b, the optical measurement can be done. The shape and length of the interconnection channels 132a, 132b, and the applied pressure at the input container 110 (not shown in FIG. 5c), is optimised to control the filling time, allowing for sufficient time for doing the optical measurement. The flow resistance of the interconnection channels 132a, 132b connecting the several reservoirs may be large, so that there is a delay between the filling of the sub-reservoirs 130a, 130b. Alternatively, the interconnection channels 132a, 132b may be made relatively long, as indicated in FIG. 5e.

Figure 6A:
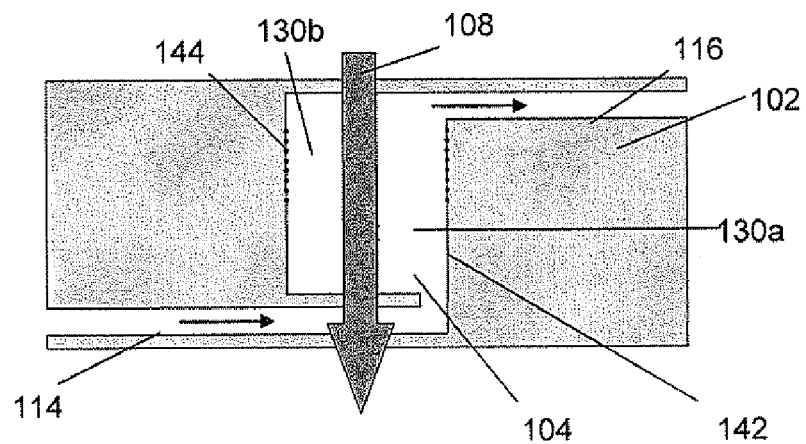
FIG. 6a shows a vertical cross-section of an exemplary device for assisting in optical characterisation having adapted measurement reservoir surface properties according to a third embodiment of the first aspect of the present invention.
Figure 6B:
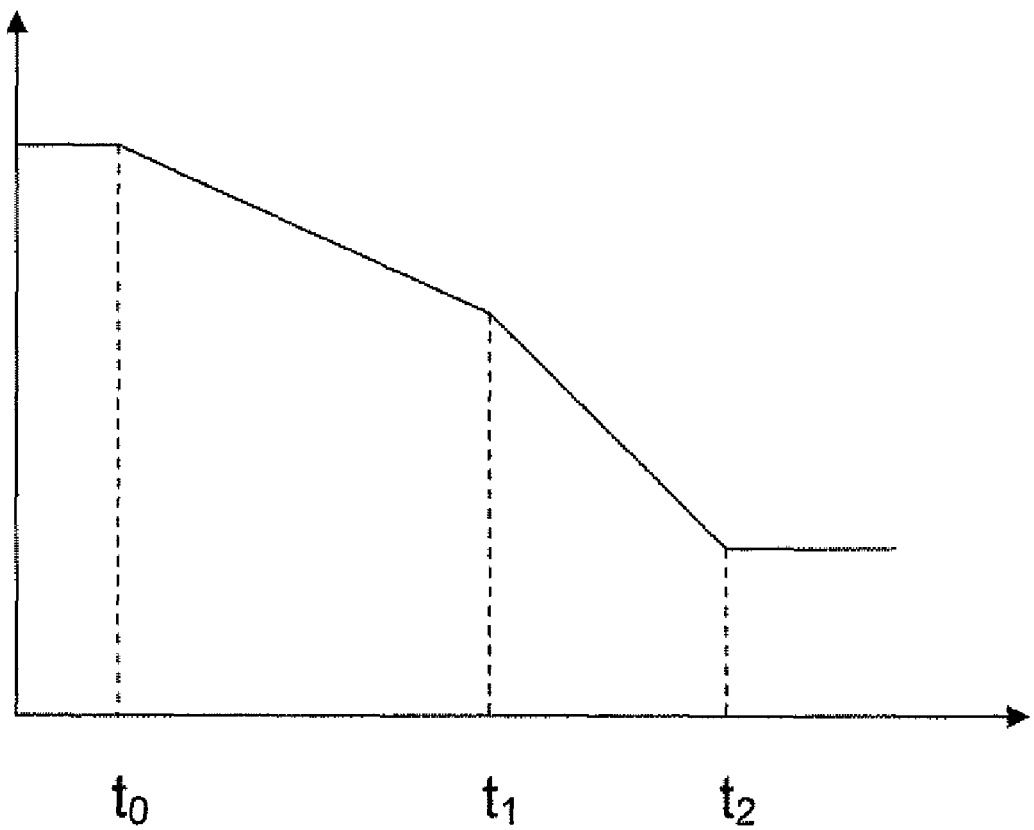

In a third embodiment according to the first aspect, the present invention relates to a device for assisting in optical characterisation of a fluid as described above, comprising the same advantages as described above, wherein different parts of the measurement reservoir surfaces have different properties for interacting with sample fluid. Typically these properties are the hydrophilic/hydrophobic properties of the surfaces. An example is shown in FIG. 6a. Variations of the filling pressure or input volumetric flow not caused by the measurement reservoir may be applied when using a device according to the present embodiment, as long as they are known such that they can be taken in to account for interpreting the obtained results. For the ease of explanation, the example is explained for a fixed filling pressure, although the invention is not limited thereto. The device 100 comprises at least one measurement reservoir 104 having in one part of the measurement reservoir, referred to as sub-reservoir 130a, first surfaces 142 with first properties and having in another part of the measurement reservoir, referred to as sub-reservoir 130b, second surfaces 144 with second properties. The sub-reservoirs 130a, 130b thus can be seen as being positioned on top of each other so that an optical path of an illumination beam passes through these sub-reservoirs 130a, 130b where the measurement reservoir 104 is illuminated. The sub-reservoirs 130a, 130b may have a different height. The first and second wall properties typically comprises a different hydrophilic/hydrophobic behaviour. Due to the different wall properties in the sub-reservoirs 130a, 130b, a variation in rate of change of the optical path length may occur, as illustrated in FIG. 6b, indicating a transmission spectrum for the illumination beam when passing through the measurement reservoir 104 during filling. At $t_0$ the transmission starts to reduce as the measurement reservoir 104 starts to get filled and the optical path length of an illumination beam 108 in the sample fluid 106 increases. The speed at which this optical detection signal changes with time changes at $t_1$ as the filling rate changes due to the different wall properties and thus due to a change in resistance of the walls against the filling pressure. At $t_2$ the transmission result does not change anymore, as this corresponds with a completely filled reservoir 104. From these transmission results, the optical path length for the optical detection signal at moment $t_1$ is known from the position of the surfaces with the different properties of the measurement reservoir, and the corresponding information is provided via measurement of the optical detection signal during filling. This information may e.g. be used in the signal processing, allowing for example interpolation of the optical path length for intermediate measurements, etc. Measuring during the filling of the measurement reservoir 104 allows to obtain a variable path length during the filling. The discontinuity in the optical detection signal, induced by the measurement reservoir surface properties, is an indication for the height of the liquid in the measurement reservoir 104 and allows to calculate the optical path length.

Figure 23A:
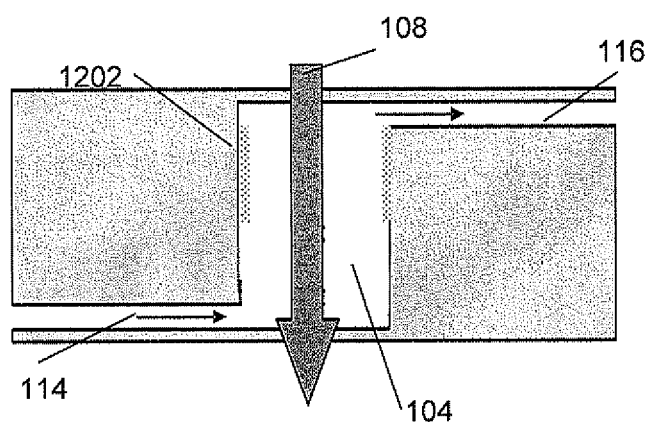
FIG. 23a to FIG. 23d show exemplary microfluidic structures according to a fourth embodiment of the present invention.
Figure 23B:
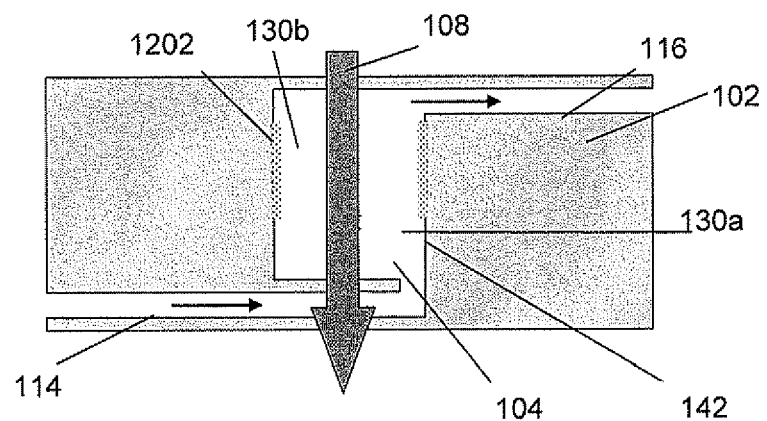
Figure 23C:
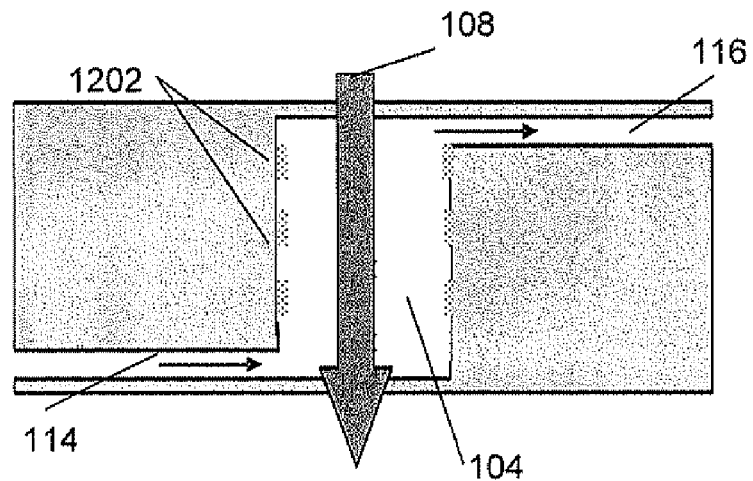
Figure 23D:
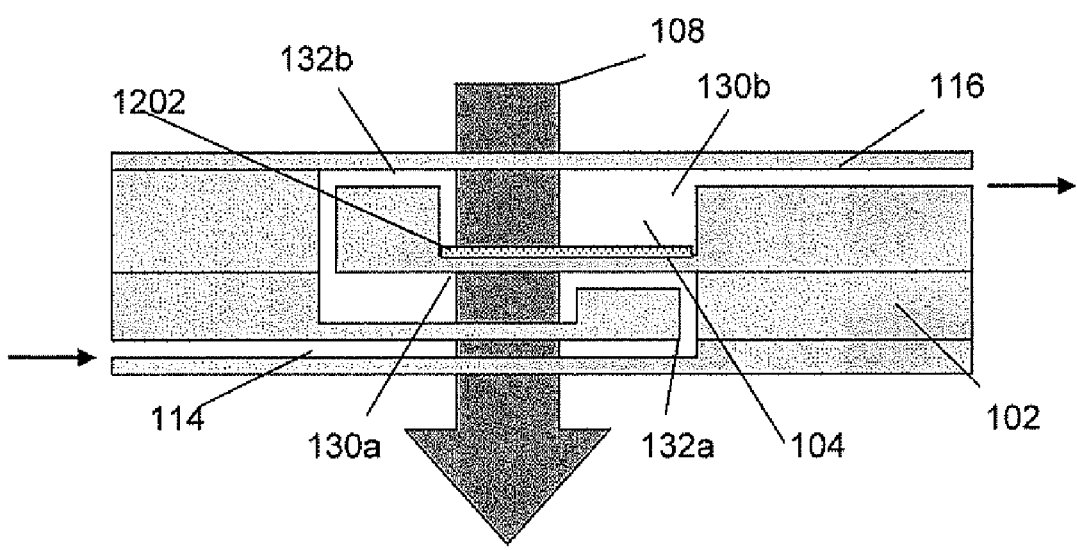

In a fourth embodiment of the present invention, the present invention relates to a device for assisting in optical characterisation of a fluid as described above, comprising the same advantages as described above, but wherein providing information of the optical path length of the illumination beam in the fluid is performed by using dissolvable material influencing the optical path length. According to the present embodiment, at least one dissolvable material is provided in the measurement reservoir that is adapted for providing information of the optical path length of the illumination beam, when being dissolved by contacting with the fluid 106. The dissolvable material may be provided at top and bottom of the measurement reservoir, with respect to the filling direction, or on a measurement reservoir side wall between a top and bottom of the measurement reservoir with respect to the filling direction. The dissolvable material may be adapted for, when being dissolved by contacting with the fluid, changing the absorption coefficient of the fluid. The dissolvable material may provide a reaction with the sample that is measurable optically. The dissolvable material may comprise a colorant. The dissolvable material may be provided as a dissolvable coating. The dissolvable material may be applied to a local restricted area of the measurement reservoir or may cover at least a significant part of a measurement reservoir side wall along the filling direction of the measurement reservoir. The latter may provide an increasing absorption coefficient of the fluid. In some embodiments, the at least one dissolvable material also may be a plurality of dissolvable materials, each indicative of different information of the optical path length of the illumination beam in the fluid. The plurality of dissolvable materials may be positioned at different positions on the measurement reservoir wall along the filling direction of the measurement reservoir. By way of example, different examples of the present embodiment are illustrated in FIG. 23a to FIG. 23d. FIG. 23a and FIG. 23b show exemplary embodiments wherein the upper part of the measurement reservoir 104 is coated with a dissolvable material 1202, in the present example being a colorant like red pigment. As soon as, during the filling, the fluid level reaches the dissolvable material, the colour of the fluid will change resulting in a variation in the optical path length of the illumination beam 108 in the fluid 106. The latter can be optically detected. The dissolvable material preferably dissolves easily such that the optical effect is rapidly obtained. Based on information regarding the position of the material, information on the optical path length can be obtained. If the amount of dissolvable material is well known, information will be obtained not only for fluid levels where the fluid reaches the edge of the region where the dissolvable material 1202 is applied but also for other fluid levels, based on the correlation between absorption change and amount of material dissolved. In FIG. 23b, one part of the measurement reservoir with first surfaces 142 without the dissolvable material is referred to as sub-reservoir 130a and another part of the measurement reservoir with second surfaces 144 with dissolvable material 1202 is referred to as sub-reservoir 130b. The sub-reservoirs 130a, 130b thus can be seen as being positioned on top of each other so that an optical path of an illumination beam passes through these sub-reservoirs 130a, 130b where the measurement reservoir 104 is illuminated. The sub-reservoirs 130a, 130b may have a different height. By way of example, the invention not limited thereto, the input channel of the device shown in FIG. 23b is positioned different than that of the device shown in FIG. 23a. In FIG. 23c, an exemplary embodiment is shown wherein at different positions along the filling direction, dissolvable material 1202 is applied to the measurement reservoir walls. The dissolvable material 1202 used may be the same material, resulting in an absorption difference in the same wavelength region, or may be different material, resulting in absorption differences in different wavelength regions. In FIG. 23d, an example is shown wherein different sub-reservoirs 130a, 130b are present, and wherein the filling of the next sub-reservoir 130b is indicated by a change in absorption due to the dissolving of a colorant. The dissolvable material 1202 in this example is applied to the bottom of the highest sub-reservoir 130b such that, as soon as this is filled, the absorption effect takes place. It is to be noticed that the present embodiment is not limited to these examples, but that the dissolvable material providing a optical measurable effect can be provided at different positions, in different patterns, etc.

Whereas in the different embodiments either the shape or the surface properties of the measurement reservoir are adapted, the present aspect also relates to embodiments wherein both the measurement reservoir shape and the measurement reservoir surface properties are adapted for varying the rate of change of the optical path length in the sample fluid. The latter may, for example, be evaluated for a constant filling pressure, a constant volumetric flow although the invention is not limited thereto. Variations of the filling pressure or volumetric flow may be applied using a device according to the present embodiment, as long as they are known such that they can be taken in to account for interpreting the obtained results.

Figure 7:
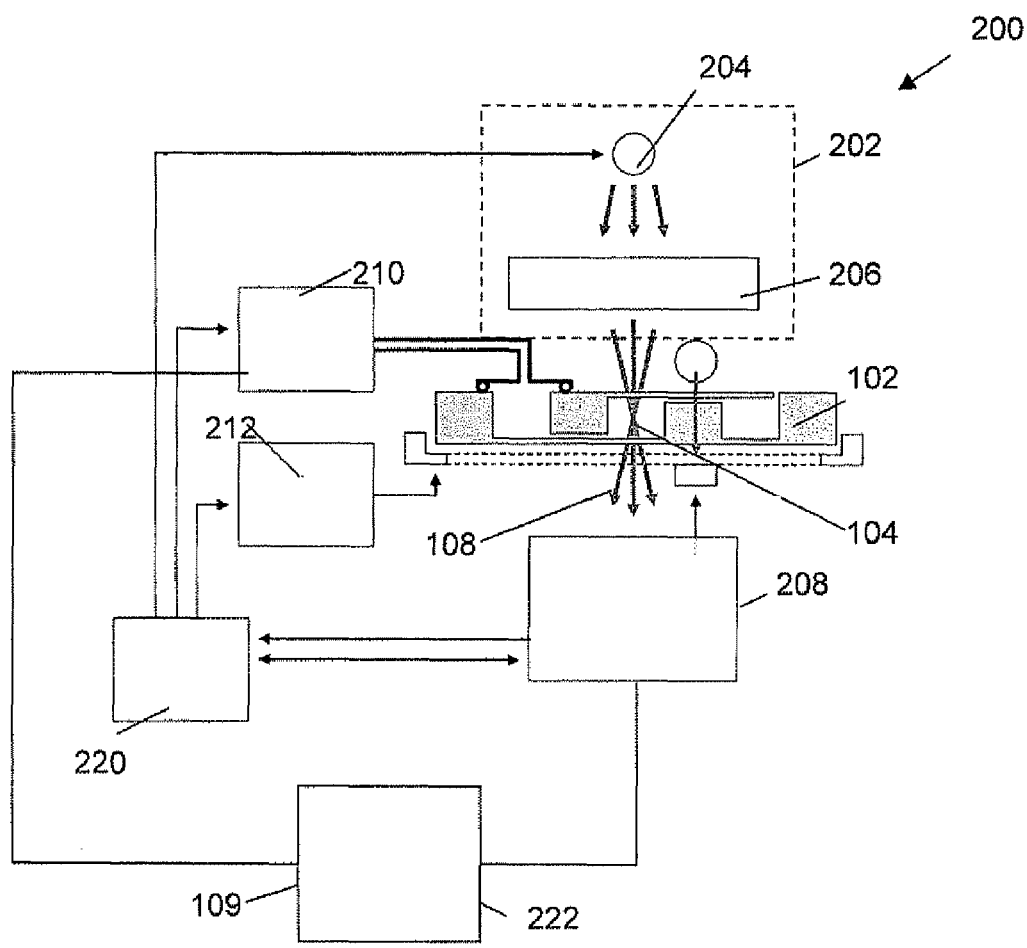
FIG. 7 shows a schematic overview of standard and optional components of an optical characterisation device according to a second aspect of the present invention.

In a second aspect, the present invention relates to an optical characterisation device for optically characterising a fluid. The optical characterisation device can comprise an illumination unit and a detection unit and is adapted for use with a device for assisting in optical characterisation and comprising a substrate and at least one measurement reservoir having a predetermined measurement reservoir shape to be filled. The optical characterisation device furthermore can comprise a fluid providing means for controlling the filling at least one measurement reservoir, whereby the detection unit is adapted for detecting optical detection signals from the sample fluid at a plurality of moments during the filling of the measurement reservoir. Such an optical characterisation device may be used in transmissive regime as well as in reflective regime. An exemplary optical characterisation device according to the second aspect of the present invention is shown in FIG. 7, showing standard and optional components of the optical characterisation device 200, which will be discussed in more detail below.

The optical characterisation device 200 can comprise an illumination unit 202. Such an illumination unit 202 may comprise an illumination source 204 and a beam forming system 206. The illumination source can be adapted for providing an illumination beam. The illumination beam may e.g. be a light beam. The illumination source 204 may be any suitable illumination source for providing the illumination beam, such as e.g. a laser or a plurality of lasers, a white light source, a filtered white light source, a LED or a number of LEDs, a xenon lamp, a pulsed xenon lamp, a deuterium lamp, etc. The illumination unit 202 may include one or a row of optical probing beams, or a 2D arrays optical probing illumination beams. The illumination beam may comprise any of or a plurality of suitable wavelengths for interacting and/or exciting the sample fluid. For spectroscopic measurements, for example, a range of wavelengths may be present in the illumination beam. The illumination beam may be imaged in the measurement reservoir 104 using a beam forming system 206, which may have a magnification M. The beam forming system comprises optical elements. It is beneficial to design the beam forming system and the read out unit so that a minimal beam diameter is obtained at the sample fluid containing structure with the largest throughput efficiency. The diameter of the spot in the measurement container is given by $d_{source}$. M and the numerical aperture of the spot in the measurement container is given by $NA_{source}/M$. At a distance L from the spot in the measurement container, the diameter for an empty measurement reservoir is given by $M*d_{source}+2*L*\tan(NA_{source}/M)$. It is to be noticed that in fluid the numerical aperture of the beam typically will be smaller, as can be derived from the formulae of Snellius. The distance L is given by half the measurement reservoir height. For small numerical apertures of the source $NA_{source}$, this diameter is given by $M*d_{source}+2*L*NA_{source}/M$. This diameter achieves a minimum for a magnification $M=\sqrt{(2*L*NA_{source}/d_{source})}$. The diameter of the minimal spot in the measurement container is $\sqrt{(2*L*NA_{source}*d_{source})}$, the NA of the spot in the measurement container is $\sqrt{(d_{source}*NA_{source}/(2*L))}$. The diameter of the spot at the top and bottom side of the container is $2*\sqrt{(2*L*NA_{source}*d_{source})}$, this is exact the double of the diameter at the spot, which is positioned at the container height.

The detection unit 208 may be adapted for detecting an optical detection signal from the sample fluid. The latter may be for example any of a transmitted illumination beam, a reflected illumination beam, a fluorescence signal in response to the illumination beam. The detection unit 208, also referred to as read-out unit, can be a spectrometer, allowing spectral measurements, or an intensity detector, allowing light intensity measurements and/or a detector allowing polarisation measurements. Such a spectrometer can comprise a light splitting means such as a prism or grating and at least one detector element for detecting different wavelengths of the incident illumination. An intensity detector may e.g. be a photo-detector, such as e.g. a photodiode or a pixelated detector. Optionally also optical filters may be provided in the illumination path. The detection unit 208 can be adapted for detecting optical detection signals from the sample fluid at a plurality of moments during the filling of the measurement reservoir 104. The detection unit 208 may include one or a row of optical detector elements, or a 2D arrays of optical detector elements.

The optical characterisation device 200 furthermore comprises a device 100 for assisting in optical characterisation of sample fluids. The latter may be a sample fluid containable device comprising a substrate 102 and at least one measurement reservoir 104 adapted to be filled and adapted to be illuminated by an illumination beam. The device 100 for assisting in optical characterisation of sample fluids may be a device 100 as described in the first aspect according to the present invention. Alternatively, the device 100 for assisting in optical characterisation of sample fluids may be a device wherein less requirements are provided for the measurement reservoir 104, e.g. with respect to the size or shape of the cross-sections in the direction perpendicular to the filling direction or with respect to the measurement reservoir properties. The device 100 for assisting in optical characterisation of sample fluids or a plurality thereof may be positioned on a moveable carrier that can be transparent or can comprise holes for optically accessing the measurement reservoirs 104. The diameter, e.g. average diameter, of the measurement reservoirs 104 may be chosen as function of the parameters of the light source (lamp, fibre, . . . ) and as function of the required height of the measurement reservoirs 104. The detection unit 208 also may be designed to match the characteristics of the beam in the measurement reservoir 104. A typical example of sizes use is given in table I. A smaller diameter may be achieved for monochromatic and coherent light.

TABLE I

| | |
|---|---|
| $d_{source}$ | 0.2 mm |
| $NA_{source}$ | 0.22 |
| L | 2 mm |
| $d_{spot}$ | 0.42 mm |
| $d_{measurement\ reservoir}$ | 0.84 mm |
| NA | 0.105 |

The fluid providing means 210 for controlling the filling of the at least one measurement reservoir may be adapted for controlling the filling of the measurement reservoir by controlling the pressure of the sample fluid into the measurement reservoir 104. It is beneficial to control the input pressure and thus indirectly the fluid providing rate, i.e. the input volumetric flow. In some example, the liquid sample is kept at a substantially constant height during an optical measurement, and speed up in between the optical measurements, i.e. controlling the filling to obtain stepwise filling. The fluid providing means 210 may be a pumping means. Also, a constant pressure may be provided, whereby optical measurements may be performed during the filling. The fluid providing means 210 may comprise a pump and valves structure for controlling the pressure on the sample inputted in the measurement reservoir 104. The fluid providing means 210 may be directly or indirectly connected to a device 100 for assisting in optical characterisation using a tubing e.g. using a flexible tubing. The fluid providing means 210 may e.g. be connected to a moveable part with the flexible tubing, whereby the device 100 for assisting in optical characterisation may be positioned on a moveable part having output holes matching the input reservoirs 110 of the device 100 for assisting in optical characterisation. A sealing may be provided for preventing leakage, e.g. air leakage, between the moveable part and the device 100 for assisting in optical characterisation. Alternatively, the fluid providing means 210 may be based on an input reservoir and fluid providing channels that are adapted in shape and/or position and/or properties such that fluid is provided by means of gravitation forces and/or hydrophilic or hydrophobic properties of the channels and reservoirs.

The optical characterisation device 200 may optionally also comprise a position controller 212 for controlling a position of the device 100 for assisting in optical characterisation or a carrier comprising one or more of such devices 100 for assisting in optical characterisation. The position controller 212 may be adapted for bringing these components to the desired position with respect to the illumination unit 202 and/or the detection unit 208. Alternatively or in combination thereto, the position controller 212 may allow to move the detection unit 208 and/or the illumination unit 202 with respect to the device 100 for assisting in optical characterisation.

Different components of the optical characterisation system may be part of a re-usable optical characterisation device or may be part of a disposable or fixed device 100 for assisting in optical characterisation.

The optical detection system furthermore optionally may comprise a feed-back system (not shown in FIG. 7) for correcting a lateral position of the sample or a focussing position, as will be described in more detail below.

The optical detection system 200 furthermore may comprise a controller 220 for synchronising the fluid providing means 210, the detection unit 208 and optionally also the illumination unit 202. The detection of the illumination beam or a luminescence response resulting there from can be performed during filling, thus requiring synchronisation. By performing the optical characterisation during the controlled filling and taking into account the predetermined measurement reservoir property information, optical characterisation of the sample may be performed, whereby quantitative results may be obtained as the amount of sample fluid with which the illumination beam may have interacted can be determined. The latter can be determined based on information about the optical path length of the illumination beam in the sample fluid.

The optical characterisation device 200 furthermore may comprise an evaluation means 222 for determining information of an optical path length of the illumination beam in the fluid from the detected optical detection signal thereby taking into account of the measurement reservoir properties, such as shape or wall properties. Such an evaluation unit 222 may comprise a processing means 109, such as e.g. a microprocessor, and/or a memory component for storing the obtained and/or processed evaluation information. Furthermore typical input/output means may be present. The evaluation unit 222 may be controlled using appropriate software or dedicated hardware processing means for executing the evaluation steps. The latter may comprise for example determining at least one variation in a rate of change of the optical detection signal as function of the filling. Preferably the variations in a rate of change of the optical detection signal as function of the filling may be discontinuities in a rate of change of the optical detection signal as function of the filling, e.g. the amount of sample fluid added to the measurement reservoir. The latter alternatively may comprise determining an optical path length based on a fixed predetermined flow for measurement reservoirs having a fixed cross-section, thus resulting in a fixed filling rate. The height of the liquid sample in the reservoir is then linear dependent on the pump rate. However, uncertainties on the diameter of the reservoir might result in an uncertainty on the height of the liquid sample in the reservoir, thus making this solution less preferable. The evaluation unit 222 may be adapted for performing derivation of a characteristic of a sample fluid as described in the method according to the third aspect of the present invention.

In a third aspect, the present invention relates to a method for optically characterising a sample fluid. The method for optically characterising a sample fluid is adapted for illuminating a measurement reservoir during filling with sample fluid, thus allowing optical characterisation for sample fluids having an analyte concentration in a wide range of concentrations. The method can comprise illuminating a measurement reservoir adapted to be filled with sample fluid and filling the measurement reservoir with sample fluid. The latter may be performed by applying pressure to an input reservoir, using pumps or in any other suitable way. Preferably filling is performed using an input channel at or near the bottom side of the measurement reservoir. The bottom side of the measurement reservoir is the side of the measurement reservoir to which the sample fluid typically is kept due to gravitational forces, when the device is positioned for being used.

The method furthermore comprises, during the illumination and the filling, detecting at a plurality of moments an optical detection signal from the sample fluid. At various moments during the filling there may be different fluid levels of the sample fluid in the measurement reservoir. Detecting an optical detection signal thereby may be for example a substantially continuous detection, detection at regular intervals or detection at predetermined moments in the filling process of the filling of the measurement reservoir. Detecting the optical detection signal may e.g. comprise an intensity and/or a spectral composition of illumination from the sample fluid. The illumination from the sample fluid thereby may be a modulated illumination beam as initially guided into the measurement reservoir, or it may be a luminescence response as response to the illumination beam initially guided into the measurement reservoir.

The method furthermore may comprise deriving a characteristic of the sample fluid based on the optical detection signals thereby taking into account a measurement reservoir property. The latter may be the measurement reservoir shape or the measurement reservoir wall properties. Deriving a characteristic of the sample fluid based on the optical detection signal may be performed based on predetermined algorithms, using neural networks or in any other suitable way. Deriving a characteristic of the sample fluid based on the optical detection signal may comprise deriving an illumination path length of an illumination beam in the sample fluid. The latter may be advantageous for determining concentrations of analytes.

An exemplary algorithm or part thereof that may be used in particular embodiments of the present invention may e.g. be evaluating the optical detection signal as function of the amount of sample fluid added to the measurement region, whereby changes in the behaviour of the optical detection signal as function of the amount of sample fluid may be detected. The optical detection signal behaviour as function of the filling will change at moments where the fluid level reaches e.g. a variation in cross-section, especially at a discontinuity in cross-section or e.g. a wall portion of the measurement reservoir having a different hydrophilic property. Consequently, the latter may provide information about the fluid level in the measurement reservoir and thus about the optical path length of the illumination beam in the sample fluid in the measurement reservoir. Such changes may be e.g. a variation in a rate of change of the optical detection signal as function of the filling, i.e. the amount of sample fluid added to the measurement region, or a variation in the variation of the rate of change of the optical detection signal. In other words, such changes may be a variation in first derivative or second derivative of the optical detection signal as function of the amount of sample fluid added to the measurement reservoir. Other measures also may be used. An alternative exemplary algorithm that may be used in embodiments wherein subsequently sub-reservoirs are filled comprises evaluating the optical detection signal as function of the number of sub-reservoirs that are filled, taking into account the typical illumination path length in each used sub-reservoir. The latter may e.g. be performed in embodiments wherein subsequently filling sub-reservoirs of the measurement reservoir is performed whereby the sub-reservoirs are positioned subsequently along an illumination path in the measurement reservoir and wherein detection of an optical detection signal from the sample is performed each time a sub-reservoir is filled. Alternative algorithms and measures also may be used.

Deriving a characteristic may comprise qualitatively and preferably also quantitatively determining analytes in the sample fluid. Identification of analytes may be performed. The presence or a concentration of predetermined analytes may be determined. The latter may e.g. be based on the transmission, reflection, absorption or fluorescence intensity and/or spectrum that occurs in the optical detection signal. Deriving a characteristic of the sample furthermore may be based on reference measurements, available from previous measurements, literature values or look up tables.

The method furthermore may comprise during said illuminating and filling, dissolving dissolvable material thus influencing the optical path length of the illumination beam in the fluid. The latter may be performed using microfluidic devices as described in the fourth embodiment of the first aspect.

The method may be performed in an automated or automatic way. It may be suitably performed using an optical characterisation device as described in the second aspect of the present invention, although the invention is not limited thereto.

Figure 8:
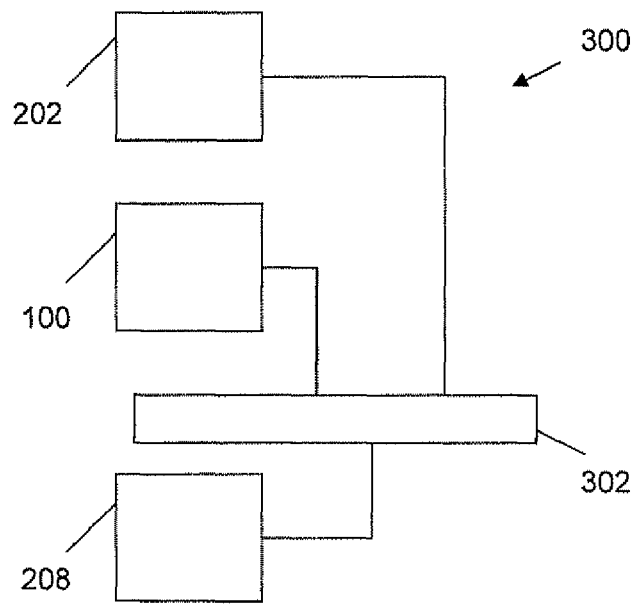
FIG. 8 shows a schematic overview of an optical characterisation device with optical control means according to a fourth aspect of the present invention.
Figure 9:
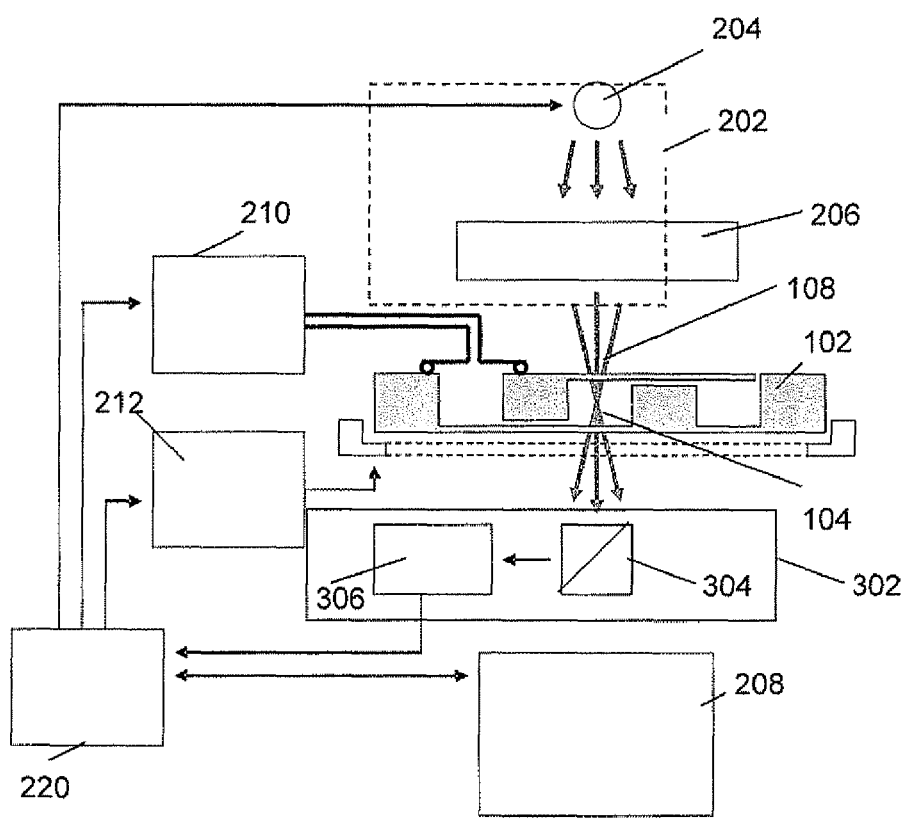
FIG. 9 and FIG. 10 show a schematic overview of an optical characterisation device with optical control means according to different embodiments according to the fourth aspect of the present invention.
Figure 10:
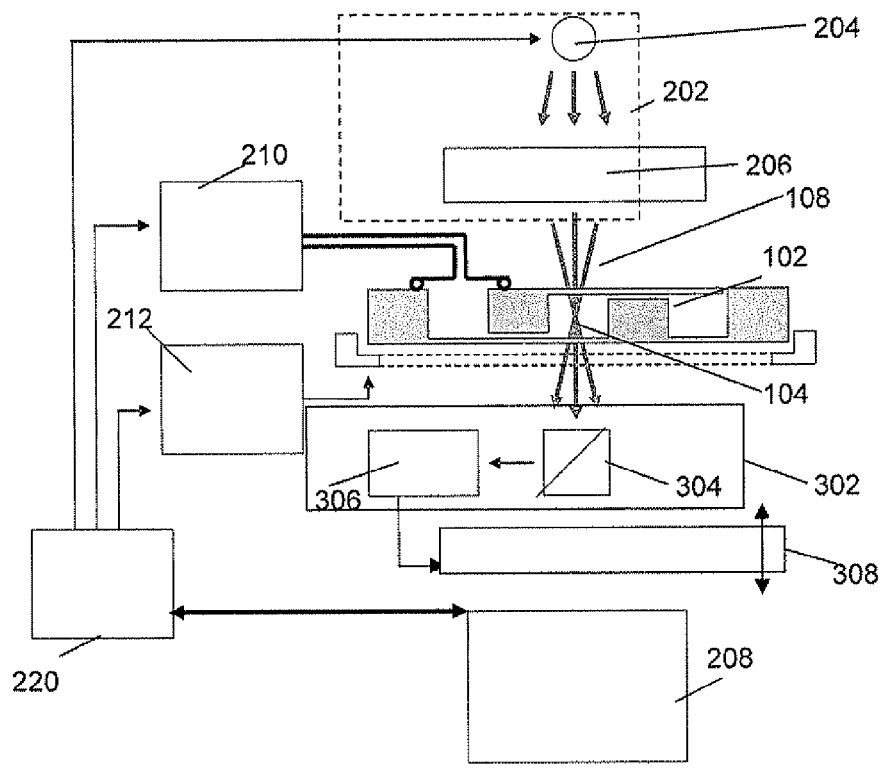

In a fourth aspect, the present invention relates to systems for optical characterisation of a sample and to corresponding methods for optically characterising a sample. The system comprises an illumination unit for illuminating a sample in a measurement reservoir, a detection unit for detecting an optical detection signal from the sample and an optical control system for monitoring illumination properties of the illumination of the sample in the measurement reservoir. Using the optical control system may allow to correct for optical misalignments or influences, e.g. introduced by the sample, an instability of the lamp or a drift of the different components with respect to each other. An overview of an optical characterisation device 300 according to the fourth aspect of the present invention is shown schematically in FIG. 8, indicating an illumination unit 202, a detection unit 208, a device 100 comprising a substrate with at least one measurement reservoir and an optical control system 302. Some exemplary embodiments are shown in FIG. 9 and FIG. 10. The illumination unit 202 and the detection unit 208 may be any suitable illumination unit 202 and detection unit 208. The illumination unit 202 may comprise an illumination source 204 suitable for optically characterising the sample, e.g. for transmission, absorption, reflection or fluorescence measurements. The illumination beam may comprise the same features and may have the same advantages as described for the illumination unit of the optical characterisation device of the second aspect of the present invention, although the invention is not limited thereto. The detection unit 208 may be adapted for detecting an optical detection signal from the sample fluid. The latter may be for example any of a transmitted illumination beam, a reflected illumination beam or a fluorescence signal in response to the illumination beam. The detection unit 208, also referred to as read-out unit, can be for example a spectrometer, allowing spectral measurements, or an intensity detector, allowing light intensity measurements. The detection unit 208 may be adapted for substantially continuously measuring, measuring during filling as described in the second aspect or merely measuring of a filled or partly filled measurement reservoir for optical characterisation of the sample. The detection unit 208 may have the same features and may have the same advantages as described for the detection unit of the optical characterisation device of the second aspect of the present invention, although the invention is not limited thereto.

The detection device 300 furthermore can comprise a substrate with a measurement reservoir for holding the sample. In other words, the detection device 300 can comprise a sample holder allowing the sample to be illuminated and an optical detection signal from the sample to be detected. The latter may be the modulated illumination beam or an optical detection signal as a response to the illumination beam. The measurement reservoir may be suitable for solid samples or fluid samples. It may be a standard measurement reservoir, or it may be adapted to provide information about the optical path length of an illumination beam in the sample, as described for the device according to the first aspect and/or the device according to the second aspect.

The detection device according to the present aspect comprises an optical control system 302 for monitoring illumination properties of the illumination of the sample in the measurement reservoir. The latter allows for detecting, correcting or optimising the illumination properties of the illumination of the sample in the measurement reservoir. These illumination properties may comprise a position and/or propagation direction of the beam after passing through the measurement reservoir, a focusing distance, a lateral alignment, etc. The monitoring illumination properties may be performed by detecting part of the optical detection signal. The latter may e.g. be obtained by splitting the optical detection signal after passing the measurement reservoir into an optical detection signal to be detected by the detection unit and an optical control signal to be detected by an additional detector 306 being part of the optical control system 302. Such splitting may e.g. be performed by a beam splitter 304. Alternatively or in addition thereto the splitting may also be performed by e.g. a rotating mirror or splitter, deflecting the optical detection signal at regular intervals to the additional detector 306 thus generating an optical control signal. The additional detector 306 may be any suitable detector for evaluating the optical detection signal beam properties. It may e.g. be a single element, a row detector or a 2 dimensional detector, adapted for providing information about the focus, the alignment in one direction or the alignment in two directions. The detector may be adapted for detecting a position or shape of an optical detection signal beam and the corresponding illumination beam. A 2-dimensional array detector may provide information about the degree and orientation of a misalignment of an illumination beam. Monitoring of illumination properties of the illumination may comprise comparing illumination properties of the illumination with a reference value, using a reference measurement, comparing with previously measured results, comparing with look up tables, etc. The obtained information may be used to do post-processing on the data from the detection unit, e.g. in order to correct errors in the measurement results. In other words, the obtained information may be used to perform software-based correction of the read-out signal. Such a software-based correction signal may be based on post-processing of obtained read-out signals or may be based on processing measurement signals differently taking into account the error, i.e. performing correction during processing. The present system and method may be used/performed in an automatic or automated way. Monitoring and/or post-processing may be performed using predetermined algorithms. Alternatively, the obtained information may be used for providing feed-back to the optical characterisation device, whereby particular components or the position thereof may be adapted. It thus may be or may be part of a feed-back system.

In one embodiment, compensation is performed for measurement errors caused by the misalignment between different components of the optical detection device 300, resulting in a misalignment between the probing beam and the detection unit 208, such as a partial overlap due to a lateral misalignment. It thus can be used to detect lateral misalignments, such as lateral beam misalignments, but for example also to detect oblique incidence of an illumination beam on a sensor surface or a shape of the meniscus of the fluid sample. A system for performing such correction is by way of illustration shown in FIG. 9

In another embodiment the optical control system for monitoring illumination properties of the illumination of the sample in the measurement reservoir may allow to adapt focussing of the illumination beam on the detection unit 208. Especially when a sample fluid is detected, the surface of the sample fluid may provide additional lensing effects on the optical detection signal beam, resulting in a defocus. The latter especially is the case if measurements are performed during the filling of the measurement reservoir, providing a shifting surface of the sample fluid and thus a shift in lensing effect during the measurement. The optical control system 302 may control a focussing system 308, comprising optical elements such as e.g. lenses or mirrors, for the optical detection signal on the detection unit 208 such that variations in the focussing position of the beam are corrected by controlling the focussing system thus at least partly refocusing the optical detection signal beam on the detection unit 208. Alternatively, the optical control system 302 may also control the vertical and horizontal position of the sample, the vertical and horizontal position of the illumination unit 202 and/or the vertical and horizontal position of the detection unit 208 for controlling the focusing in the optical characterisation system 300. In this way, compensation of the misalignments may be performed. The latter is illustrated in FIG. 10.

Other components may be present in the optical characterisation device 300 as described in the optical characterisation device according to the second aspect of the present invention; Such additional components may for example be a fluid providing means 210, a position controller 212, a synchronisation means 220, etc.

In a fifth aspect according to the present invention, a device for assisting in optical characterisation of a liquid sample is described. The device typically comprises a substrate with at least one measurement reservoir adapted to be filled with said liquid sample and at least one gas collecting cavity adapted to collect gas. The latter allows to reduce or remove from the optical beam probing area at least part of gas bubbles introduced in the liquid sample in the measurement reservoir during filling with liquid sample. In this way, it becomes possible to fill the measurement cavity entirely with liquid sample, without the inclusion of air bubbles in the beam probing area. Such a device thus typically may be a liquid containing structures for holding small liquid samples, wherein the liquid containing structure comprises a combination of channels and reservoirs. In embodiments according to the present invention, the reservoirs can be filled with the sample liquid substantially without or with a reduced inclusion of air or gas bubbles or foam in the optical path through the liquid sample. Embodiments according to the present aspect may be applied to any type of sealed microfluidics device in which a closed cavity having only a small input and output channel needs to be filled. The structure may allow for optical measurements through the fluid sample where the optical path length through the sample can be adjusted or varied, i.e. the amount of gas bubbles may be substantially reduced or gas bubbles may even be completely removed from the optical beam probing area in the liquid sample, even during filling of the measurement reservoir. The device for assisting in optical characterisation may comprise the same features, may have the same properties and may have the same advantages as the device described in the first aspect of the present invention. E.g. the device may consist of a specific arrangement of micro-fluidic channels and reservoirs. This may be realised by bonding two or more microstructures plates, where at least the part where the optical path passes is transparent. The micro-structured plates may be made of any suitable material such as for example polymer, metallic or glass material, etc. The structuring, i.e. making channels and reservoirs may be done via moulding, embossing, etching, ablation, milling or drilling. The surfaces of the channels and reservoirs may be treated such that they have a hydrophobic or hydrophilic behavior, different from the bare material properties. This can be for example achieved by chemical means or via O2 plasma exposure. The liquid containing structures may be arranged on carriers. The carriers may be a disposable or a re-useable object. It can be a stand-alone object or it can be integrated in a measurement instrument, i.e.

an optical characterisation device. In some embodiments there may be one device for assisting in optical characterisation per carrier, in other embodiments multiple devices for assisting in optical characterisation may be combined on a carrier, grouped in arrays. The reservoirs may be positioned such that their pitch may be compatible with SBS standards or not. In some applications, the shape of the measurement reservoir(s) may be optimised for overlap with the probing beam. This allows to minimise the required reservoir volume.

In some embodiments, the measurement reservoir may be designed so that a minimal volume is required to achieve maximal variation in optical path length through the liquid sample, allowing to maximise the measurement range for the concentration or fluorescence signal.

Figure 12A:
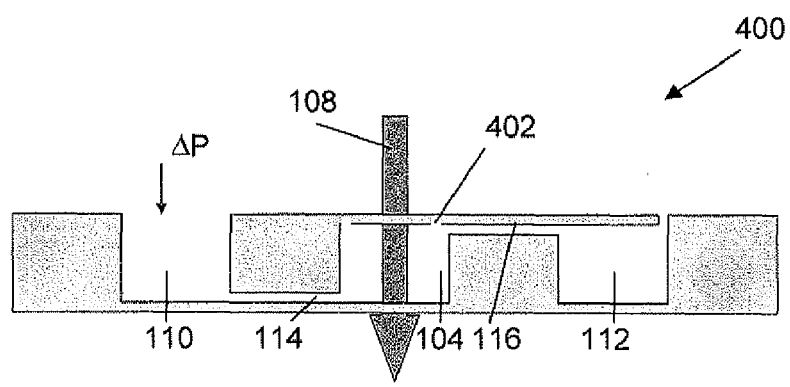
FIG. 12a to FIG. 13b show cross-sections of a device for assisting in optical characterisation according to an embodiment of the fifth aspect of the present invention.
Figure 12B:
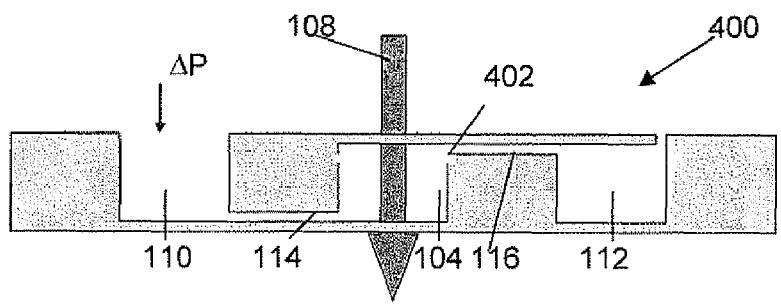

The shape of the measurement reservoir may be optimised for maximal lateral overlap with the probing beam, or for measurement where the droplet has a variable height. The measurement reservoir may be cylindrical. In some embodiments, as shown in FIG. 12a and FIG. 12b, the device for assisting in optical characterisation may comprise an input reservoir 110, an interconnect channel 114 connecting the input reservoir 110 with the measurement reservoir 104, the measurement reservoir 104, an interconnect channel 116 connecting the measurement reservoir 104 with the output reservoir 112, and the output reservoir 112. Furthermore the measurement reservoir 104 is in contact, e.g. direct contact with a gas collecting cavity 402. By way of example, the gas collecting cavity 402 can be on top of the measurement reservoir 104, as shown in FIG. 12a, or at a wall around the measurement reservoir 104, as shown in FIG. 12b. In certain embodiments, the input reservoir 110 and/or output reservoir 112 might not be required and the fluid injection may take place directly into the measurement reservoir. In other embodiments, one input reservoir 110 may be connected to a multitude of measurement reservoirs 104, or a multitude of input reservoirs is connected to one measurement reservoir 104. The output reservoir 112 may allow to recycle the liquid sample.

The diameter and height of the measurement reservoir 104 may be in the order of one millimeter. This allows to measure the characteristics of sample volumes of a few micro liter or smaller. The input reservoir 110 and the output reservoir 112 may be larger, allowing for easy injection of the liquid sample in the measurement reservoir 104 using standard equipment.

In some embodiments, the sample is deposited in the input reservoir, and a overpressure is applied to the input reservoir. The fluid sample is pumped to the waste reservoir, passing through the fluid measuring structure and allowing to measure the transmission through the fluid. In other embodiments, no external force is required to pump the liquid sample to the measurement reservoir. The flow is achieved by gravitation forces and/or hydrophilic/hydrophobic properties of the channels and reservoirs. The device furthermore may comprise an overpressure releasing means as described in more detail in the sixth aspect.

Figure 13A:
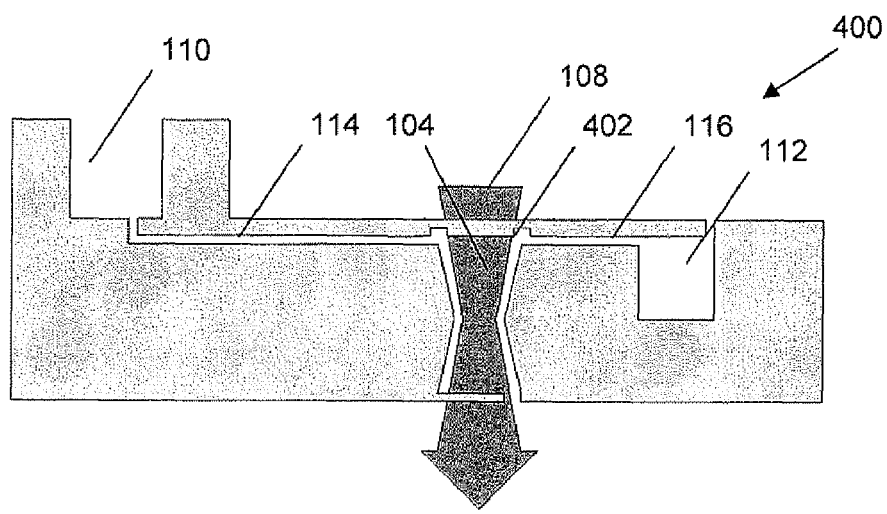
Figure 13B:
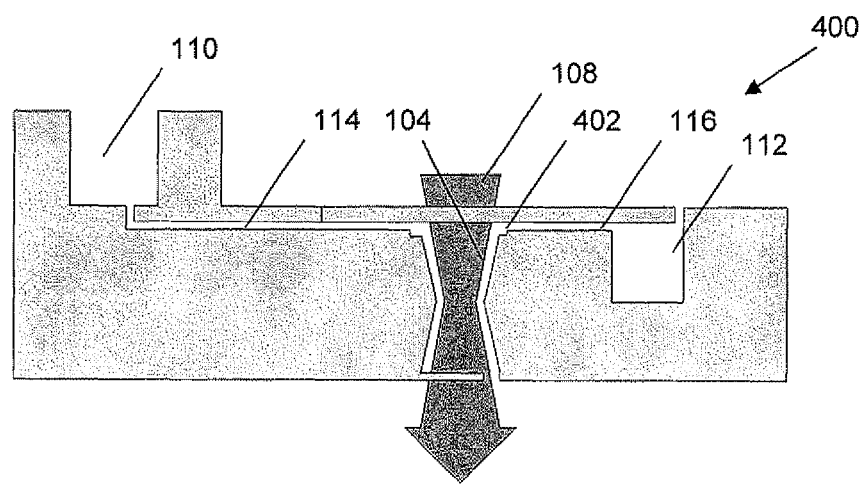

In a first particular example according to the fifth aspect, the invention relates to a device for assisting in optical characterisation as described above, whereby the gas collecting cavity is ring shaped. A ring-shaped cavity thereby may be such that a cavity surrounds a portion of substrate material, e.g. a central portion of substrate material. It may for example have a torus-shape, have a circular shape or a rectangular shape. A cross-section of an exemplary embodiment is shown in FIG. 13a and FIG. 13b. The device 400 comprises at least one measurement reservoir 104 with at least one gas collecting cavity 402 in the present example being one or more ring-shaped cavities. By way of example, the gas collecting cavity 402 can be on top of the measurement reservoir 104, as shown in FIG. 13a, or at a wall around the measurement reservoir 104, as shown in FIG. 13b. The latter allows the reservoir to be filled without or with a reduced risk on inclusion of gas bubbles, e.g. air bubbles, in the optical path through the reservoir. The gas collecting cavity or cavities 402 may be added at the top and/or bottom of the reservoir. During the filling, bubbles will be trapped in these gas collecting cavity 402, and the liquid fills the rest of the measurement reservoir 104. A gas collecting cavity 402 at the bottom of the measurement reservoir may be advantageous e.g. if the cavity is filled from the top. If the filling occurs fast, air or gas bubbles could be trapped below the fluid, having no way to escape except via such a gas collecting cavity 402 at the bottom.

It is an advantage of particular embodiments according to the present aspect that introduction of gas bubbles, e.g. air bubbles, in the sample fluid in a measurement reservoir can be reduced from being present in the optical beam probing area. It furthermore is an advantage of particular embodiments of the present aspect that filling of the measurement reservoir can be controlled taking into account a hydrophobic or hydrophilic nature of the reservoir. It is also an advantage of particular embodiments that the optical path length of an irradiation beam in the sample fluid in the measurement reservoir can be determined accurately. Furthermore, it is an advantage of particular embodiments of the present aspect that the filling of small reservoirs can be controlled. The filling may be controlled by the pressure and the fill time, in combination with features and properties of the measurement reservoir, input channel and overpressure release channel. Small changes in the pressure and/or fill time result in a partial filling of the reservoir, due to the small volume of the reservoirs compared to the pump rate.

In a sixth aspect according to the present invention, a device for assisting in optical characterisation of a liquid sample is described comprising at least one measurement reservoir adapted to be filled with liquid sample, an input channel in connection to the measurement reservoir for providing sample fluid to the measurement reservoir and an overpressure releasing means connected to the input channel. The overpressure releasing means typically allows to control the filling of the measurement reservoir, as it prevents air or gas being introduced in the measurement reservoir, after the input reservoir has been emptied, i.e. when no more sample liquid is present. The overpressure releasing means thus may be adapted to avoid air being driven into the measurement reservoir, after the input reservoir is emptied. The overpressure releasing means may be adapted such that sample liquid is rather driven to the measurement reservoir than through the overpressure releasing means, but that gasses escape more easily through the overpressure releasing means than through the measurement reservoir. The device furthermore may comprise the same features, the same properties and the same advantages as described in the first aspect or the fifth aspect of the present invention. The overpressure releasing means may be in direct contact with the input channel. It may be an overpressure releasing channel or overpressure releasing pipe. The overpressure releasing means also may be adapted to control the emptying of the measurement reservoir. The overpressure releasing means thus basically will serve as a valve when air comes in the input channel. The valve is closed as long as liquid passes, but opens when air passes and the liquid has fully filled the measurement reservoir. This is accomplished by the overpressure releasing means having a certain resistance for the fluid, which is larger than the measuring reservoir.

Figure 14A:
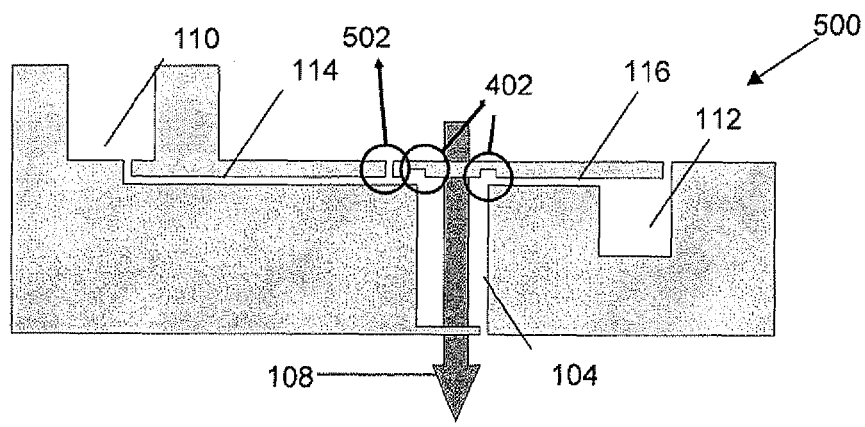
FIG. 14a and FIG. 14b show cross-sections of a device for assisting in optical characterisation according to an embodiment of the sixth aspect of the present invention.
Figure 14B:
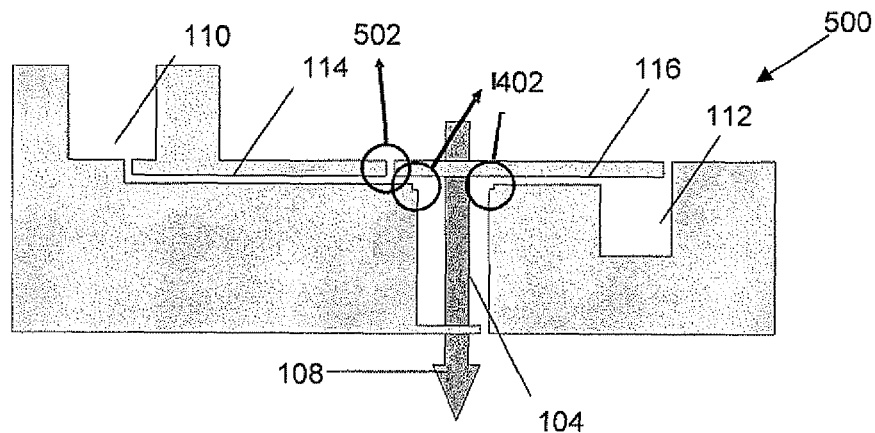

In one embodiment according to the sixth aspect, the present invention relates to a device as illustrated in more detail in FIG. 14a and FIG. 14b. In the exemplary device 500 shown, a measurement reservoir 104, an input channel 114 and an overpressure releasing means 502 can be seen. Furthermore, a gas collecting cavity 402 is shown in the device 500, although the device does not need to comprise such a gas collecting cavity 402. By way of example, the gas collecting cavity 402 can be on top of the measurement reservoir 104, as shown in FIG. 14a, or at a wall around the measurement reservoir 104, as shown in FIG. 14b. The overpressure releasing means 502 may induce a small hole in the input channel 114, allowing to stop the pumping once the fluid passed over that hole in the input channel and thus air is pumped through the input channel. In the exemplary embodiment shown in FIG. 14, liquid sample may be pumped in the input channel 114 towards the measurement reservoir 104 using a second predetermined pressure level, typically larger than the first predetermined pressure level. The diameter of the overpressure releasing means 502 is chosen that at this second predetermined pressure level, the flow resistance is too large for the sample fluid to flow through the overpressure releasing means as long as the measurement reservoir 104 is not filled. After the sample is pumped into the measurement reservoir 104, the overpressure is expanded through the small hole, and the sample remains in measurement reservoir without being pumped further towards an output reservoir. The length of the overpressure releasing means may be designed so that the flow resistance is sufficiently small to allow the latter. By applying a third, larger pressure at the input reservoir, the liquid sample can be pumped further towards the waste container.

Figure 15:
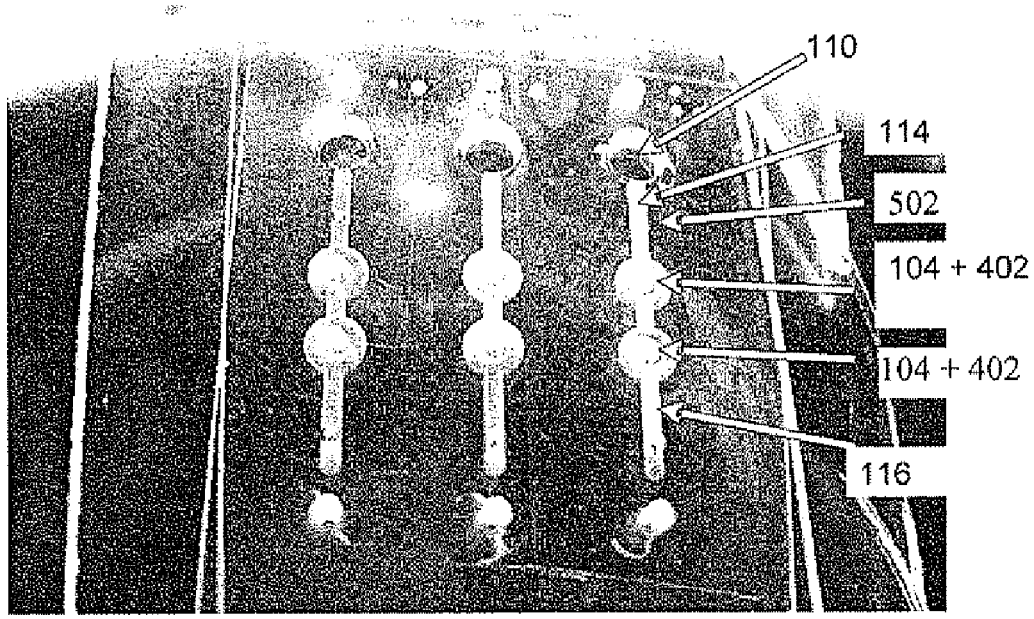
FIG. 15 shows a photographic image of a device for assisting in optical characterisation according to an embodiment of the fifth and sixth aspect of the present invention.

In another embodiment, the present invention relates to an optical device for assisting in optical characterisation of a liquid sample as described above, wherein the device for assisting in optical characterisation comprises both an overpressure releasing means and at least one gas collecting cavity 402. Typically, in devices according to such an embodiment, after the liquid filled the measurement reservoir 104, it is forced to move into the gas collecting cavity 402. Such a gas collecting cavity 402 typically may be connected via a channel to air, in order to allow collected gas to escape. If this channel has a higher resistance to fluid flow than the overpressure releasing means 502, it will be only filled with fluid extremely slow and the excess fluid will be directed rather to the overpressure releasing means 502. This is also the case for air that is blown into the input channel when the entire input reservoir is emptied. A photographic image of an exemplary device with two measurement reservoirs 104 in series comprising ring shaped gas collecting cavities 402 and an overpressure releasing means 502 is shown in FIG. 15.

In a seventh aspect, the present invention relates to a method and system for optically characterisation of a material. According to the present aspect, the method and system are adapted for illuminating the material with an illumination beam and obtaining at least two optical response signals from the material to be characterised, also referred to as at least two optical detection signals from the material to be characterised. One optical detection signal of the at least two optical detection signals thereby typically corresponds with a known illumination path length for the illumination beam in the material, the known illumination path length being substantially longer than an unknown illumination path length of a second optical detection signal of the at least two optical detection signals. The method and system according to the present aspect furthermore are adapted for deriving the unknown illumination path length based on the at least two optical detection signals and the known illumination path length. The optical characterisation system may be any optical characterisation system, such as a transmission, absorption, reflection or fluorescence characterisation system. By way of example, the method and system will be further described for a spectrometer system using transmission measurements, but it will be clear for the person skilled in the art that the features of such methods and systems can be mutatis mutandis applied to other types of optical characterisation systems.

The system may be adapted by a controller, controlling the detection unit for detecting at least two optical detection signals. Such a system thus may be similar to the system shown in FIG. 7 but comprising a controller for controlling the detection unit for detecting at least two optical detection signals.

The at least two optical detection signals may be obtained in measurements on different reservoir or may be obtained during filling. In a preferred embodiment, the at least two optical detection signals are obtained during the filling of a measurement reservoir, whereby typically the measurement at full measurement reservoir may be used as corresponding with a known illumination beam path length in the material to be characterised. When performing the methods of the present aspect during filling or using a system adapted for measuring at least two optical detection signals according to the present invention during filling, the cavity may be either adapted or not adapted for varying the rate of change of the illumination path length at different moments during the filling.

The methods and systems according to the present aspect may be performed with systems and methods as described in any of the previous aspects of the present invention or any of the embodiments thereof.

One way of using the optical detection signals, the invention not being limited thereto, is described below by way of illustration. If Fresnel reflection losses are neglected, the transmission T of an illumination beam typically is given by $$T = 10^{-\epsilon c L} \quad [1]$$

with $\epsilon$ the molar extinction coefficient, L the illumination beam path length in the material and c the molar concentration of the absorbing features in the material. The factor $\epsilon c L$ typically may be called the optical density (OD) of the sample material, e.g. sample fluid. From the above equation, the molar concentration of the absorbing features in the material can be expressed as $$c = \frac{-\log(T)}{\epsilon L} \quad [2]$$

and thus as $$\frac{dc}{c} = \frac{-dL}{L} \quad [3]$$

meaning the relative accuracy on the concentration depends linearly on the relative accuracy of the path length. The latter implies that the measurement concentration can be determined with a higher accuracy if the absorption length or illumination beam path length of interaction with the material is larger. The present invention uses this principles for more accurately determining also high concentrations of analytes by calibrating shorter illumination beam path lengths using the optical measurements. Measurements of shorter illumination beam path lengths typically may be performed to detect high concentrations, for a large L the transmitted light typically will reach the noise level. Thus there is a need for a small L that can be measured accurately.

For parts of the spectrum that are within measurable range for at least two optical detection signals corresponding to at least one known longer illumination beam path length $L_{known}$ and one unknown, or less accurate known, illumination beam path length $L_{unknown}$, it can be derived that $$OD_{L_{known}} = L_{known}/L_{unknown} \cdot OD_{L_{unknown}} \quad [4]$$

Figure 16A:
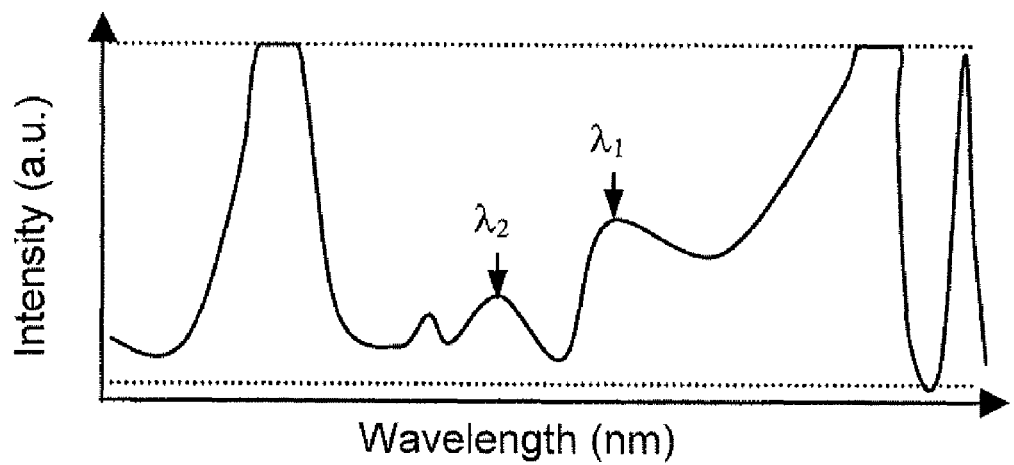
FIG. 16a and FIG. 16b illustrate different transmission spectra for illumination beams interacting over different path lengths with material, as used in methods and systems according to the seventh aspect of the present invention.
Figure 16B:
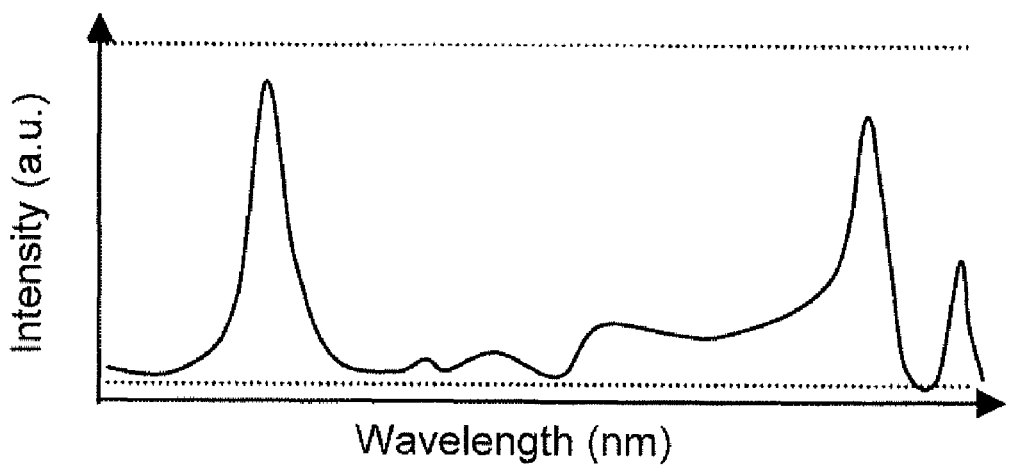

By way of illustration, an example is given wherein the transmission spectrum for a fluid could be used to determine an illumination beam path length more accurately. In the present example the known illumination beam path length is 1 mm, whereas the unknown illumination beam path length may be of the order of 0.1 mm. In the spectrum corresponding with the unknown illumination beam path length, shown in FIG. 16a, a few of the peaks are saturated due to the limited bandwidth of the detection unit, e.g. photodetector array, other parts of the spectrum are in the noise level, and the rest is within the measurable range for the spectrometer. In the spectrum corresponding with the known illumination beam path length, shown in FIG. 16b, the overall transmission is lower due to the increased length of the light path through the absorbing fluid. Again parts can be determined of the spectrum that are within the measurable range (sufficiently above noise level and not saturated) of the spectrometer. For these parts of the spectrum that are within measurable range for both path lengths, we can write:

$$OD_{L=1mm} = 10 \cdot OD_{L=0.1mm} \quad [5]$$

and thus $$OD_{L_{1mm}} = L_{1mm}/L_{0.1mm} \cdot OD_{L_{0.1mm}} \quad [6]$$

Assume that there is a 10 μm (guess) tolerance on the fluid height, which gives a relative error on the concentration of respectively 10% (L=0.1 mm) and 1% (L=1 mm). Using the optical measurements, e.g. of equation [6], a more accurate fluid height of the unknown illumination beam path length in the small column can be calculated as both OD-values can be measured. The tolerance on the height of the small column is then close to 1% rather then 10%.

The methods and systems according to the present aspect are especially suitable for correcting or taking into account tolerances present in an optical characterisation system, such as e.g. a tolerance on a cavity height in a molded part due to shrinkage, a tolerance due to a gap between mold inserts during injection and due to tolerances on the mold insert itself. Other tolerances on a finished part also include assembly tolerances as adhesive thickness etc. Some of these tolerances are absolute, meaning they do not depend on L itself. These tolerances influence the path length L of a beam that is transmitted through the cavity vertically. The impact of the tolerances becomes larger as the cavity height is reduced.

By way of illustration, a number of examples of use of such an optical characterization device will be provided, the present aspect not being limited thereto.

In a first example, the method and system according to the seventh aspect is applied to an optical characterisation device using a device 100 for assisting in optical characterisation as shown in FIG. 5c and discussed in the second embodiment of the first aspect of the present invention. Typically, in this example, the smallest reservoir height that is measured, is the input channel height. The largest sample fluid height that is measured is obtained when the entire serpentine is filled. Although typically there will be some additional assembly tolerances present influencing the accuracy of the largest sample fluid height, e.g. induced as several layers may be bonded with an adhesive having a thickness that can vary slightly, it is to be expected that the relative accuracy for the largest sample fluid height will be much higher than for the accuracy of the sample fluid height in the input channel. By deriving the smaller sample fluid heights from the combination of optical measurements and a value for the largest fluid height, a more accurate estimate of the sample fluid height in the input channel, or e.g. of the input channel height, can be made during the optical measurements, e.g. transmission measurements. The latter may e.g. be based on calculation using equation [4].

In a second example, the method and system according to the seventh aspect is applied to an optical characterisation device using a device 100 for assisting in optical characterisation as shown in FIG. 5a and discussed in the second embodiment of the first aspect of the present invention, whereby first a non-constant flow is assumed. The latter may be a known or induced variation of the flow rate or it may be a drift on the exact volumetric flow rate, although a constant volumetric flow rate was envisaged for filling the measurement reservoir. Assume a number of optical measurements are performed during the filling, whereby the last measurement is the one that measures the absorption of the fully filled cavity. The latter can be easily determined as additional flow of fluid does not change the transmission anymore. The last measurement result then corresponds with a fluid height equaling the full measurement reservoir depth. This value can be used in combination with results of the optical measurements to determine the intermediate optical path lengths by using equation. It thereby is preferred that information relating to the meniscus during filling is obtained and combined with the obtained results as typically at fully filled cavity, the fluid is in contact with the top wall of the cavity and there is no meniscus whereas during the intermediate measurements there is definitely a meniscus. Such meniscus information can e.g. be obtained using an optical control system, e.g. comprising a beam splitter and detector, as described in the fourth aspect of the present invention. The latter allows to correctly interpret the calculated optical depth of the fluid, using e.g. equation [4]. The present example is an illustration on how the method and system according to the present aspect can be advantageously used to compensate for variations in volumetric flow rate. It thus allows to calculate the intermediate fluid height whereby at least partial compensation is obtained for a non-constant volumetric flow.

A third example is similar to the second example, but wherein the volumetric flow rate is constant. For a constant flow the instant volume of the rising sample fluid can be derived from the time information, as illustrated by way of example in FIG. 5b. In this example, there is a fixed relationship between time and volume. The exact optical path length at every measurement can be determined from the combination of optical measurements and a value for the largest fluid height, which is available as soon as the entire reservoir has been filled. From the reservoir geometry and flow rate the exact sample fluid shape at times $t_i$, i.e. when the edges of the sample fluid hit the discontinuity in the reservoir, can be calculated and thus the influence of the meniscus can be calculated and determined, without the need for a 2D photodetector that tracks the beam before entering the spectrometer. All necessary parameters to interpret the calculated optical path length at the discontinuities are then available.

In a fourth example, the methods and systems according to the present aspect are applied to a simple reservoir with straight walls and with constant wall properties. During the filling measurements are done at several moments. The measured data at complete filling can then be used in combination with the obtained optical results for intermediate measurements, to calculate the exact optical path in the fluid at these intermediate measurements. The latter can e.g. be performed using equation [4]. In order to further improve accuracy, typically the illumination beam may be tracked in the measurement reservoir, using e.g. a method or system as described in the fourth aspect of the present invention. This information can allow estimation of the meniscus shape of the fluid and thus correction of the measurement data, thus incorporate the effects of presence of a curved fluid surface.

It is an advantage of methods and systems according to embodiments of the present aspect of the present invention that high accuracy can be obtained.

Figure 11:
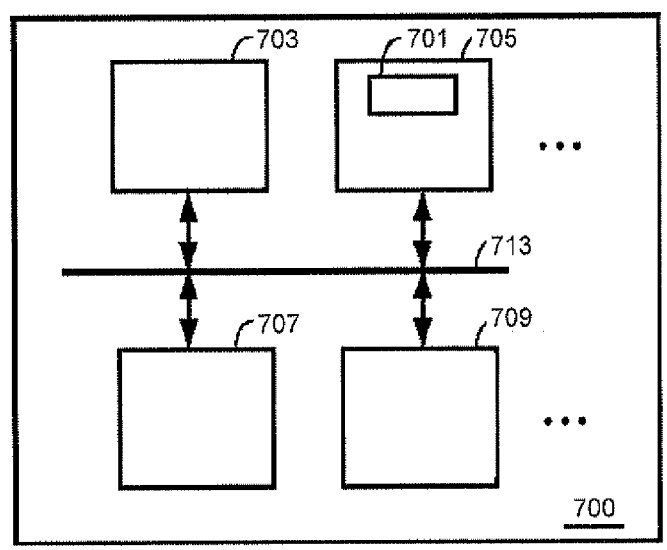
FIG. 11 shows a computing means for performing a method according to a third aspect of the present invention.

The above-described method embodiments of the present invention may be implemented in a processing system 700 such as shown in FIG. 11. FIG. 11 shows one configuration of processing system 700 that includes at least one programmable processor 703 coupled to a memory subsystem 705 that includes at least one form of memory, e.g., RAM, ROM, and so forth. It is to be noted that the processor 703 or processors may be a general purpose, or a special purpose processor, and may be for inclusion in a device, e.g., a chip that has other components that perform other functions. Thus, one or more aspects of the present invention can be implemented in digital electronic circuitry, or in computer hardware, firmware, software, or in combinations of them. The processing system may include a storage subsystem 707 that has at least one disk drive and/or CD-ROM drive and/or DVD drive. In some implementations, a display system, a keyboard, and a pointing device may be included as part of a user interface subsystem 709 to provide for a user to manually input information. Ports for inputting and outputting data also may be included. More elements such as network connections, interfaces to various devices, and so forth, may be included, but are not illustrated in FIG. 11. The various elements of the processing system 700 may be coupled in various ways, including via a bus subsystem 713 shown in FIG. 11 for simplicity as a single bus, but will be understood to those in the art to include a system of at least one bus. The memory of the memory subsystem 705 may at some time hold part or all (in either case shown as 711) of a set of instructions that when executed on the processing system 700 implement the steps of the method embodiments described herein. Thus, while a processing system 700 such as shown in FIG. 11 is prior art, a system that includes the instructions to implement aspects of the characterisation methods is not prior art, and therefore FIG. 11 is not labelled as prior art.

The present invention also includes a computer program product which provides the functionality of any of the methods according to the present invention when executed on a computing device. Such computer program product can be tangibly embodied in a carrier medium carrying machine-readable code for execution by a programmable processor. The present invention thus relates to a carrier medium carrying a computer program product that, when executed on computing means, provides instructions for executing any of the methods as described above. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

Figure 17A:
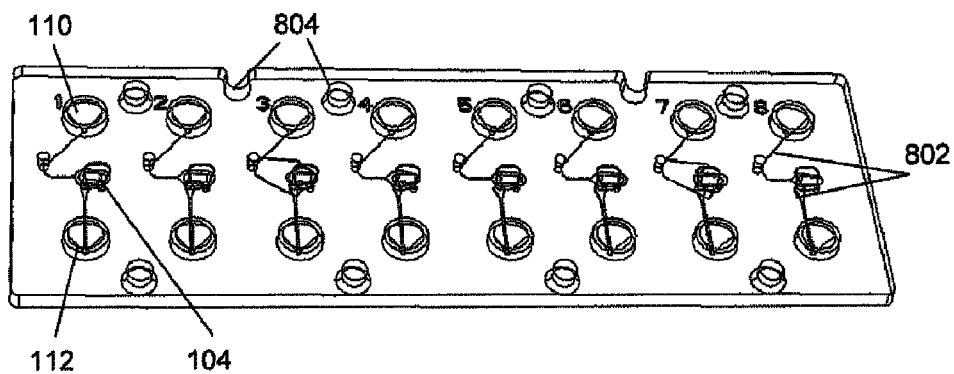
FIG. 17a to FIG. 17c illustrates a transparent top view, a top view and bottom view respectively of an exemplary microfluidic slide according to an embodiment of the present invention.
Figure 17B:
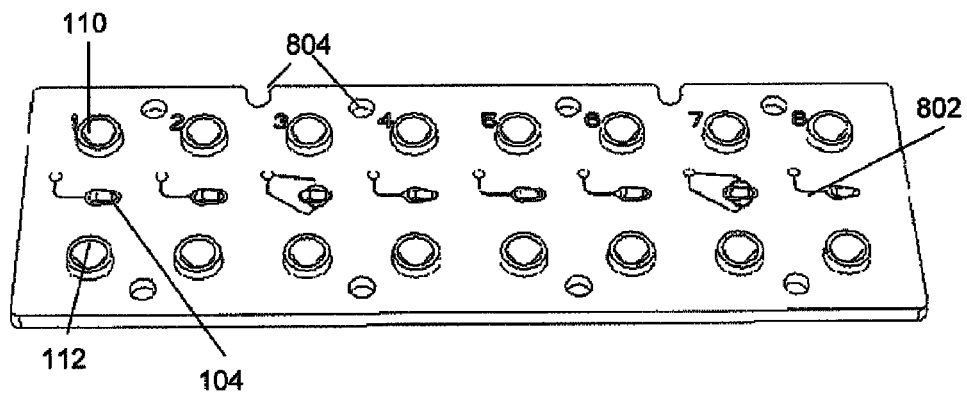
Figure 17C:
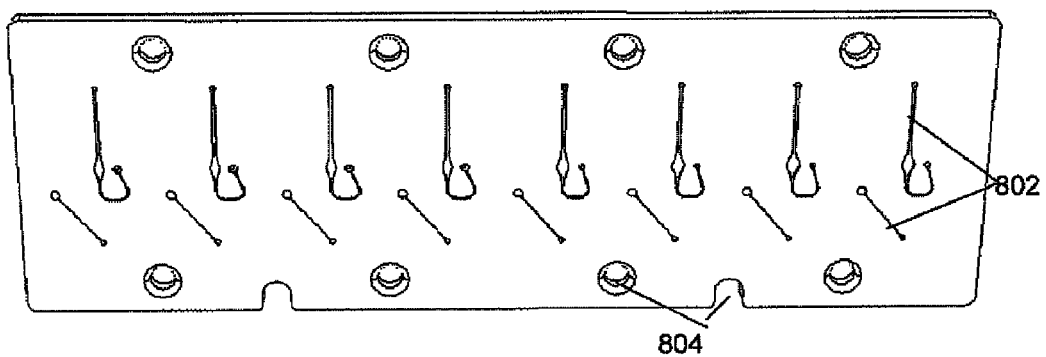

By way of further illustration, the present invention not being limited thereto, some particular examples of microfluidic devices are further discussed, as well as a number of manufacturing techniques that can be used for manufacturing the microfluidic devices according to embodiments of the present invention. FIG. 17a to FIG. 17c show a transparent top view, a top view and a bottom view respectively of an exemplary microfluidic device 800 for assisting in characterisation of a fluid. The exemplary microfluidic device 800 comprises a substrate 102 with a series of individual microfluidic detection structures, each comprising an input reservoir 110, a measurement reservoir 104 and an output reservoir 112. The system furthermore may comprise different interconnection channels 802 for connecting the different reservoirs. The microfluidic device 800 furthermore comprises alignment features 804 for aligning the substrate 102 with respect to the measurement system. Such alignment features 804 may occur at an edge of the device or be located on any other suitable location, such as e.g. in the plane of the device.

Figure 18A:
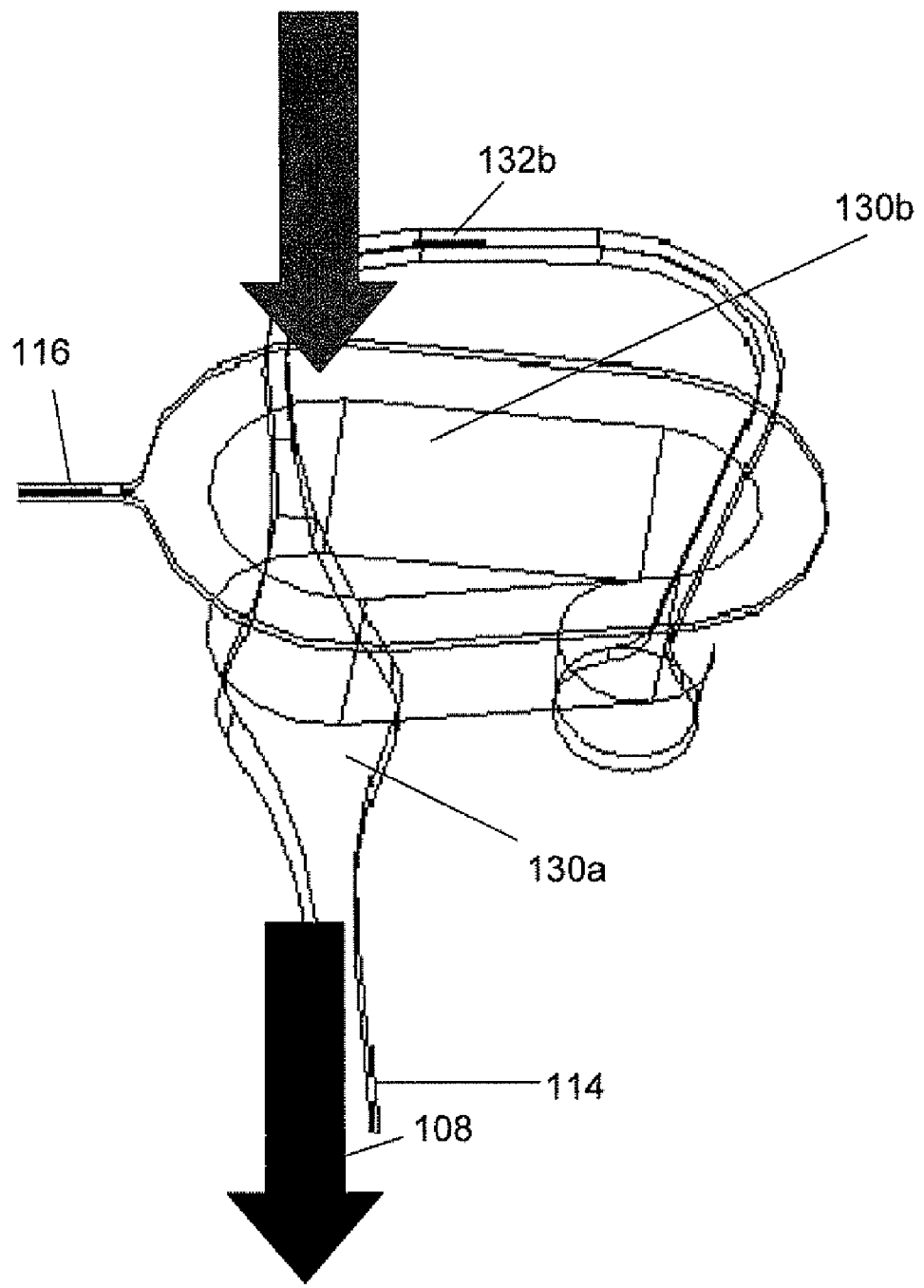
FIG. 18a to FIG. 18g shows (parts of) exemplary microfluidic structures according to embodiments of the present invention.
Figure 18B:
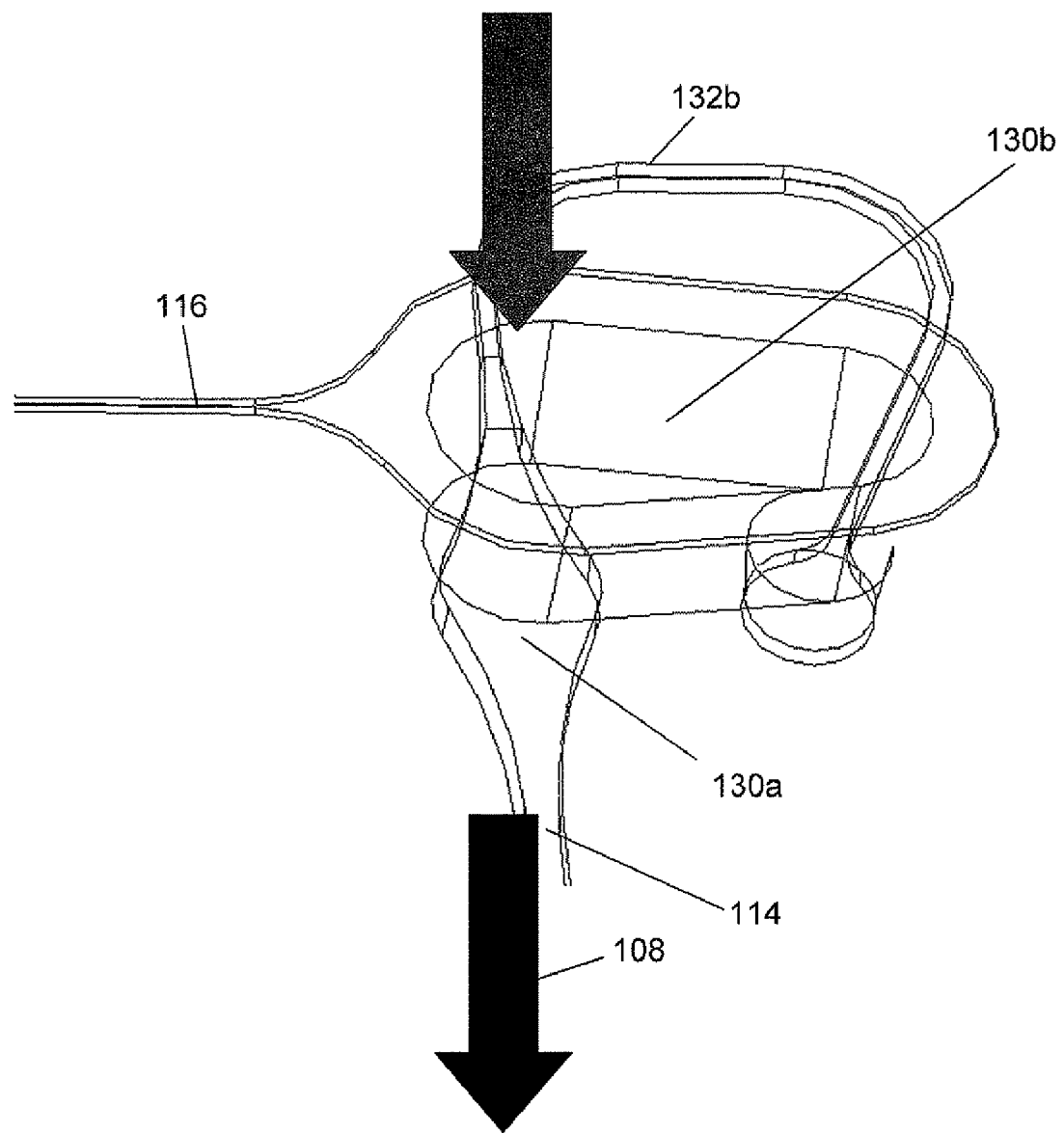
Figure 18C:
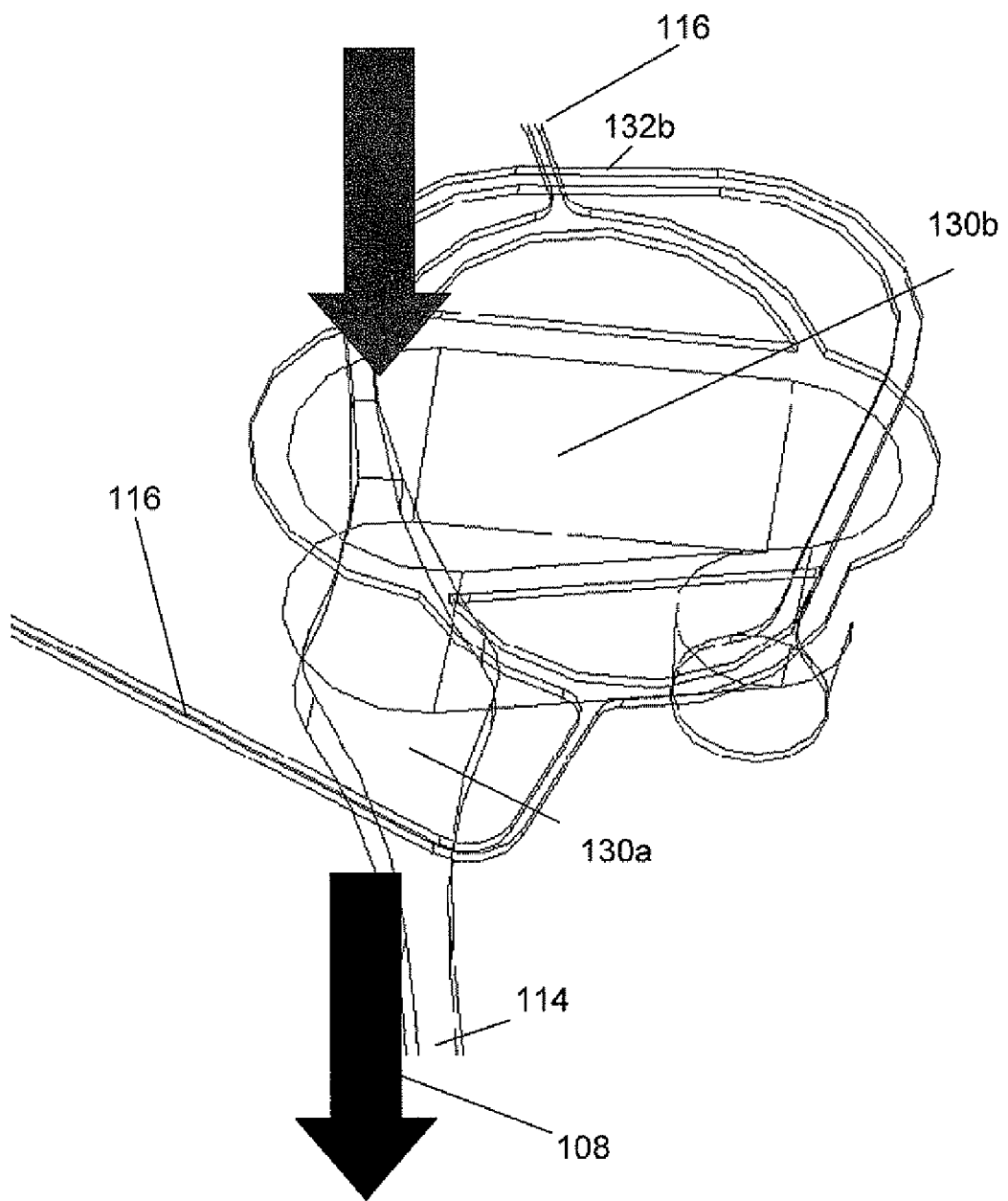
Figure 18D:
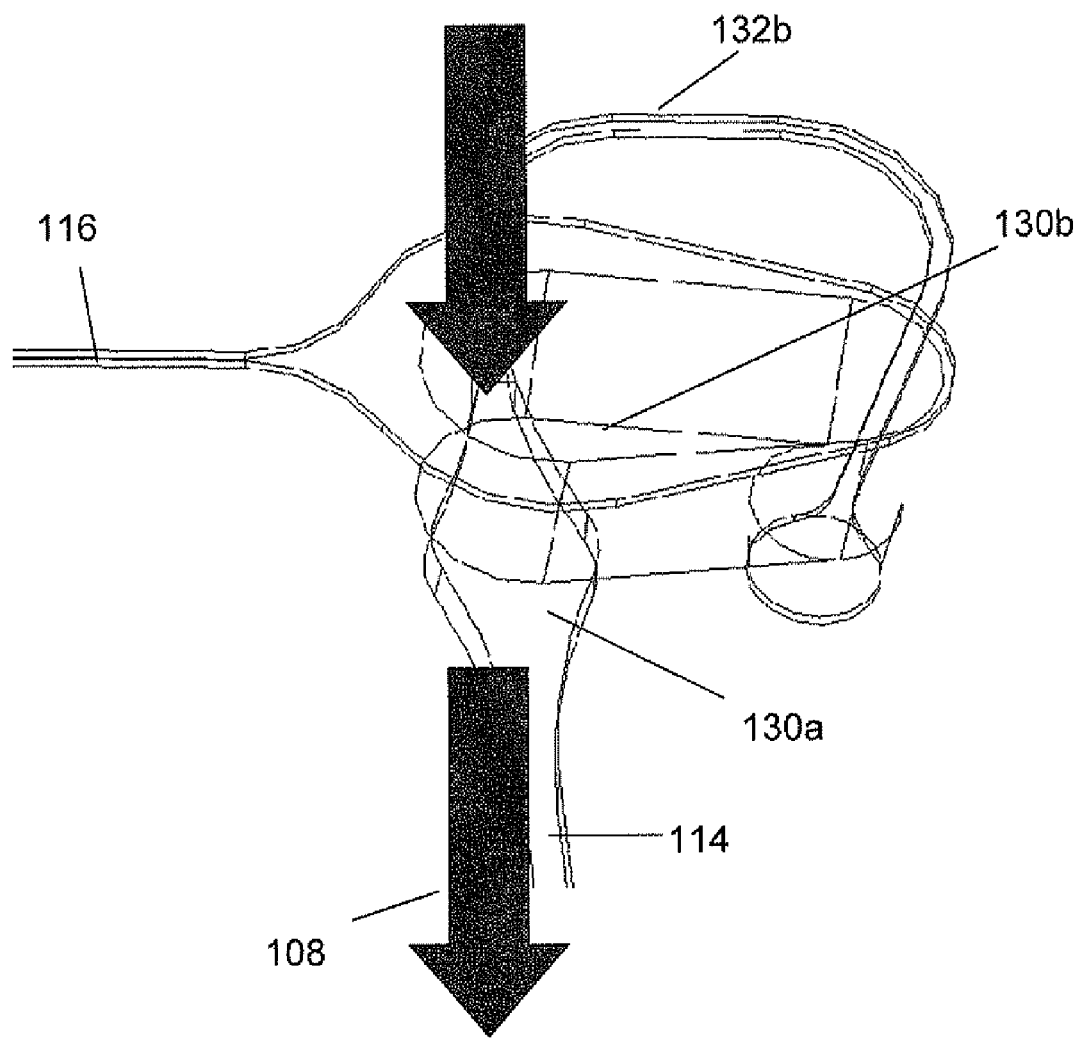
Figure 18E:
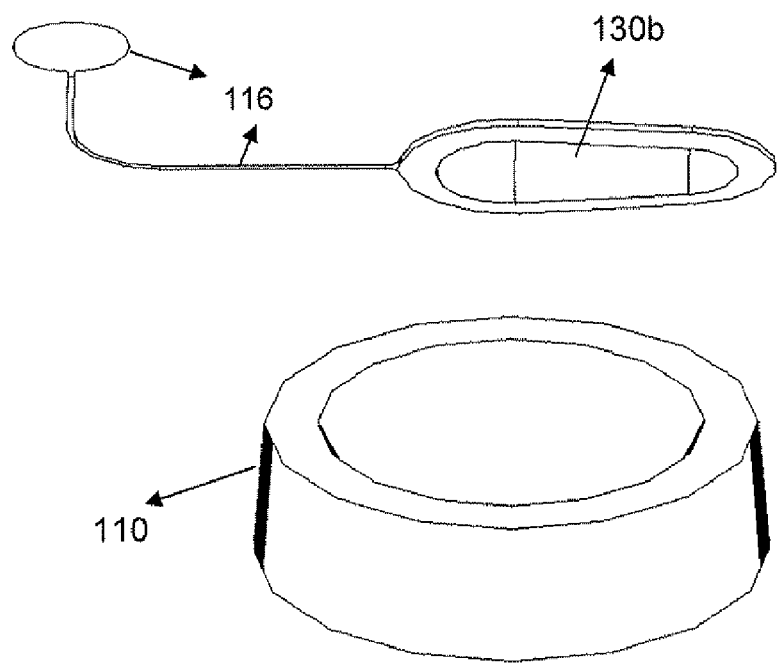
Figure 18F:
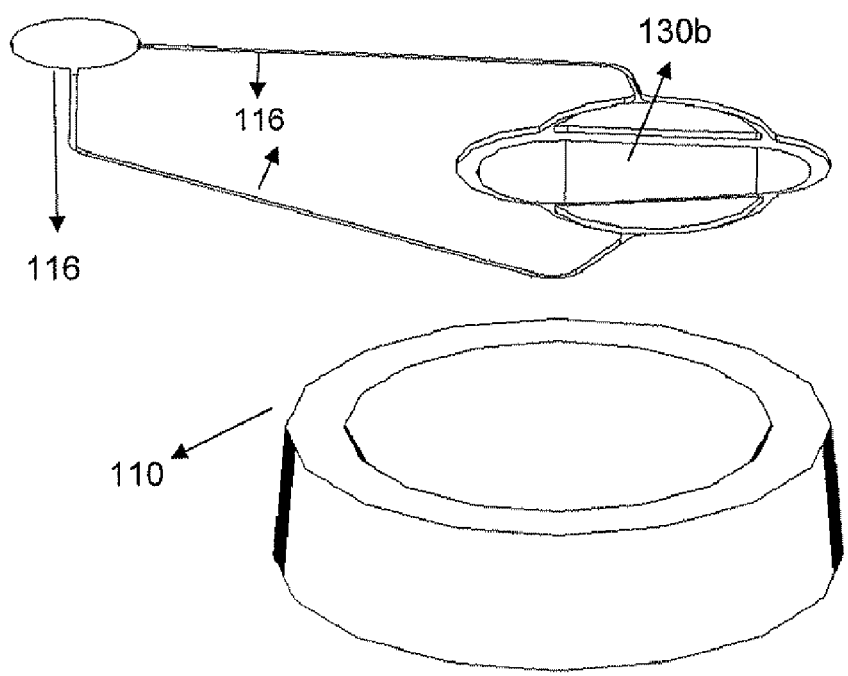
Figure 18G:
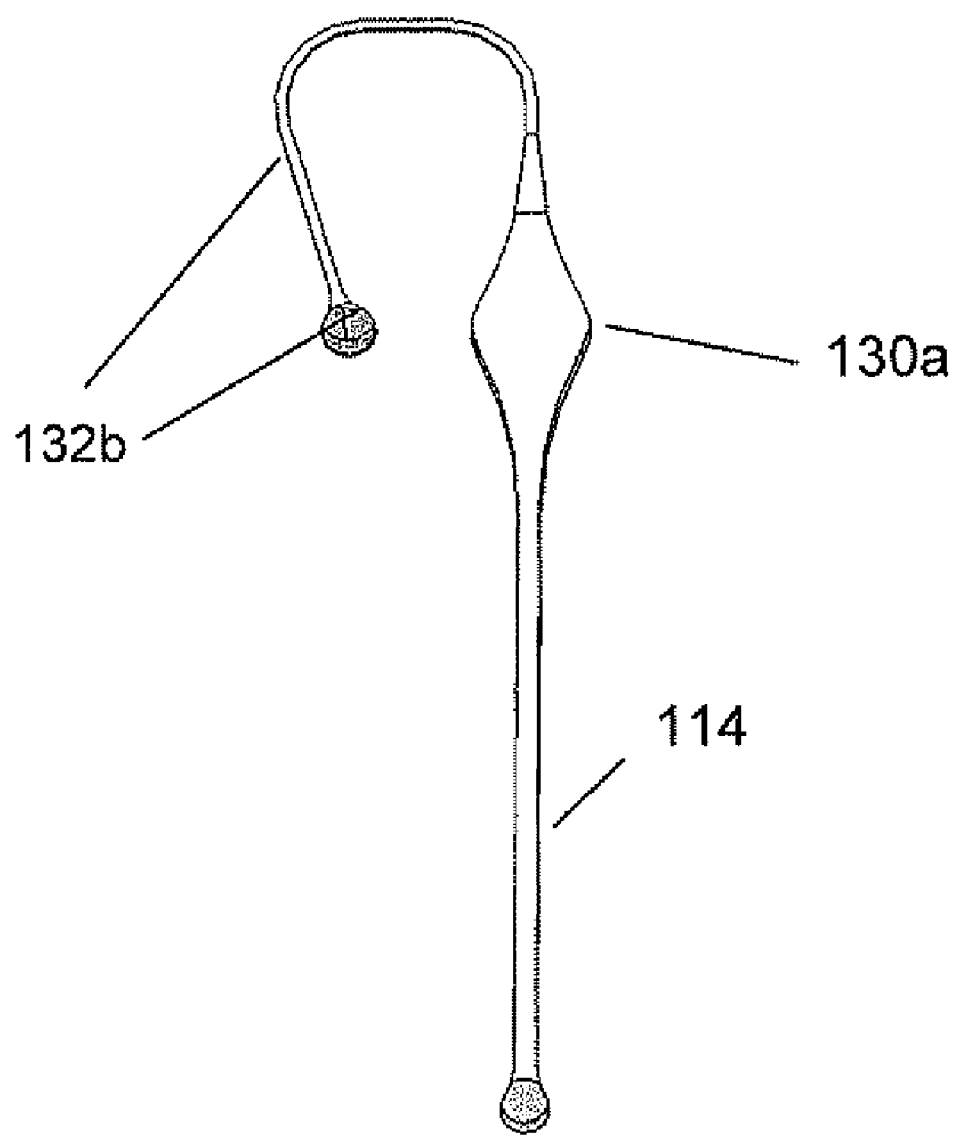
Figure 19A:
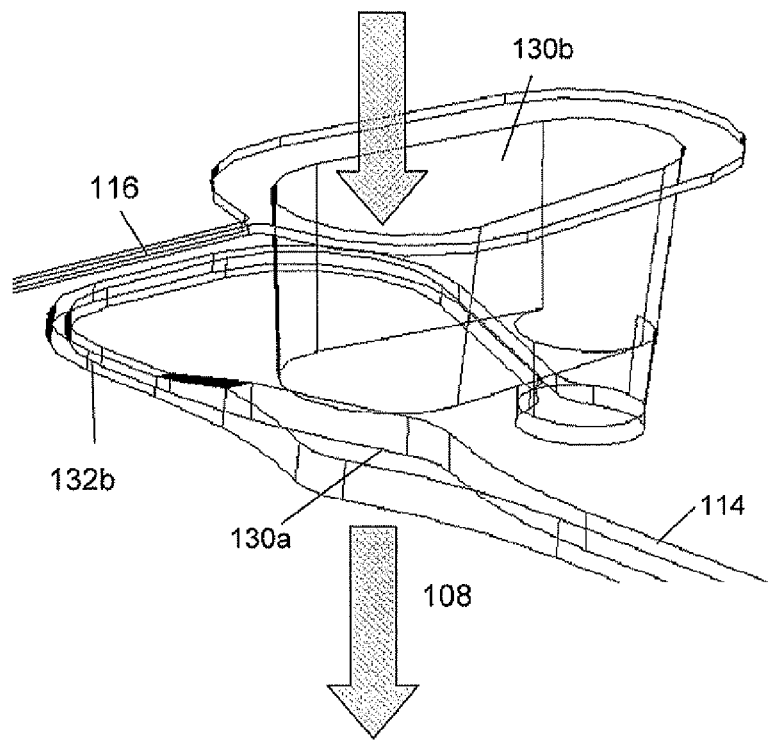
FIG. 19a to FIG. 19d illustrate cross-sections of different examples of (parts of) microfluidic structures according to embodiments of the present invention.
Figure 19B:
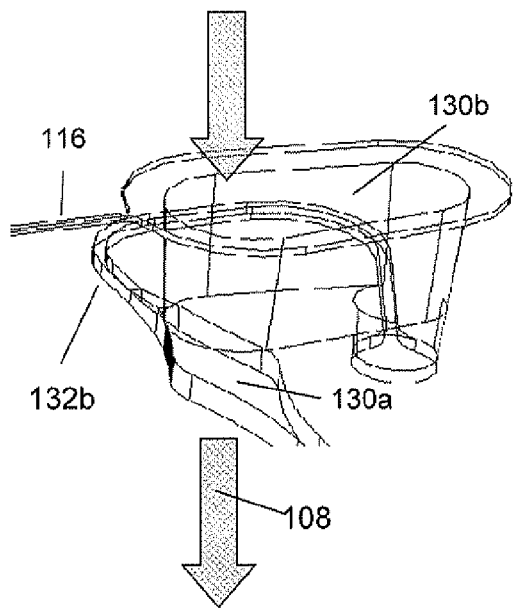
Figure 19C:
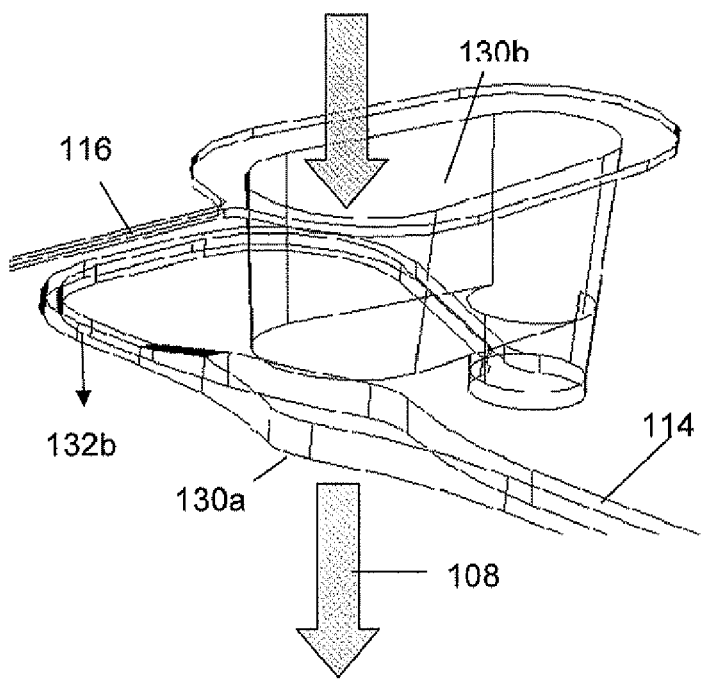
Figure 19D:
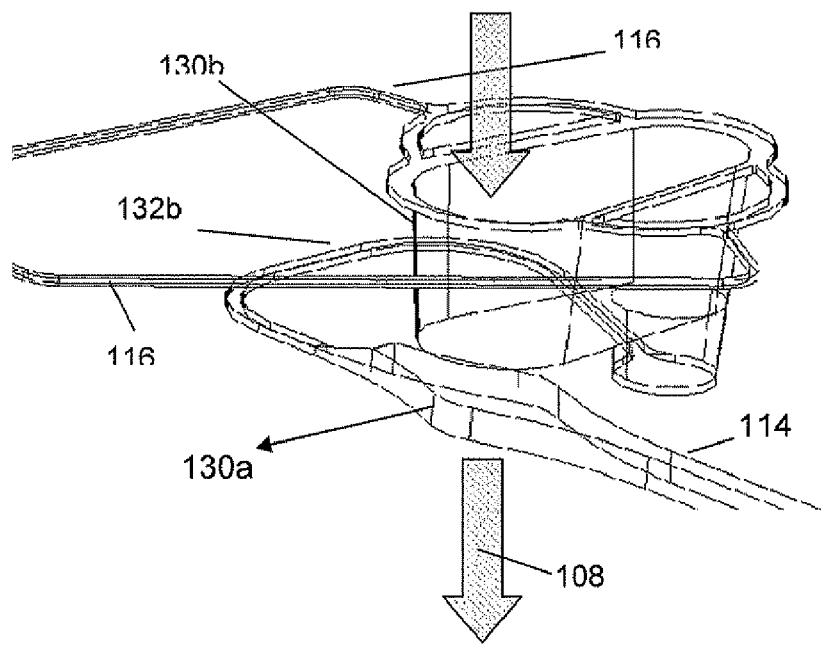

FIG. 18a to FIG. 18d show detailed drawings of an exemplary microfluidic structure that can be used in a microfluidic device 800 as described above. In the present examples, the microfluidic structures 900 are based on a measurement reservoir 104 comprising two sub-reservoirs 130a, 130b, e.g. as schematically shown in FIG. 5c or FIG. 5e. A first sub-reservoir 130a in the present example is the lower reservoir and a second sub-reservoir 130b in the present example is the upper reservoir. The direction of illumination with the illumination beam 108, when in use, also is indicated. The different microfluidic structures shown in FIG. 18a to FIG. 18d, differ in the shape and or position of the output channel 116, also referred to as waste channel. Furthermore, the input channel 114 also is indicated. An interconnection channel 132b connecting the different sub-reservoirs 130a, 130b also is indicated. FIG. 18e to FIG. 18g show further detailed views of the microfluidic structure. FIG. 18e and FIG. 18f show detailed top view of different variants of the microfluidic structure while FIG. 18g shows a detailed bottom view of a microfluidic structure. Different variants of the microfluidic structure are shown in cross-section in FIG. 19a to FIG. 19d, whereby variations are provided in the position and shape of e.g. the input channel 114, and/or interconnection channel 132b and/or output channel 116, also referred to as waste channel. Again a two-chamber measurement reservoir is provided with a first sub-reservoir 130a being the lower reservoir and a second sub-reservoir 130b being the upper reservoir. Furthermore, the optical beam 108, when the microfluidic device is being irradiated, is shown, as well as the interconnection channel 132b between first and second sub-reservoir.

In the above examples, the shape and position of different components such as the output channel 116 are varied. The selection may be adapted in order to obtain a more easy moulding of the components or to influence the flow of the fluid in the structure. In the present examples, embodiments of the invention not being limited thereto, the sizes of the different components may be selected as follows. The cross-sectional size of the output channel in the present examples may e.g. vary between 30 µm×50 µm and 50 µm×50 µm. The cross-sectional size of the input channel in the present examples may be of the order of 200 µm by 200 µm. The cross section of the interconnecting channel may be of the order of 100 µm by 100 µm or 100 µm by 50 µm. The cross-section of the first sub-reservoir may be of the order of 200 µm by 1 mm and the cross-section of the second sub-reservoir may be substantially larger, e.g. 1 mm by 1 mm. The radius of curvature at the side of the second sub-reservoir where the radiation crosses may be 0.5 mm. It is to be considered that non of the above cited distances are limiting for any of the above described embodiments. Sizes and shapes may be selected in view of the moulding process to be performed as well as in view of appropriateness for the test for which the invention will be used.

Figure 20A:
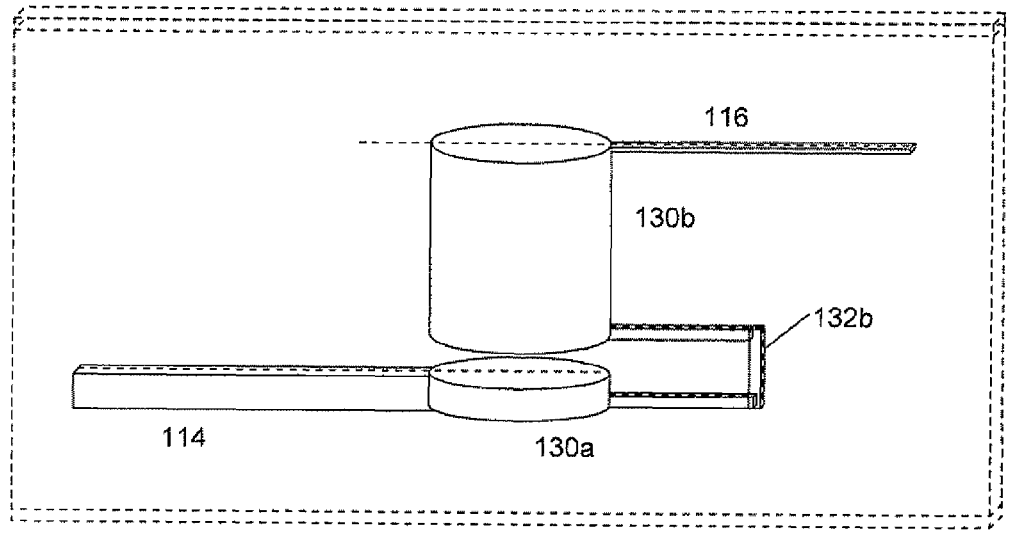
FIG. 20a to FIG. 22c shows moulds as usable for manufacturing moulded microfluidic structures and resulting moulded microfluidic structures according to embodiments of the present invention.
Figure 20B:
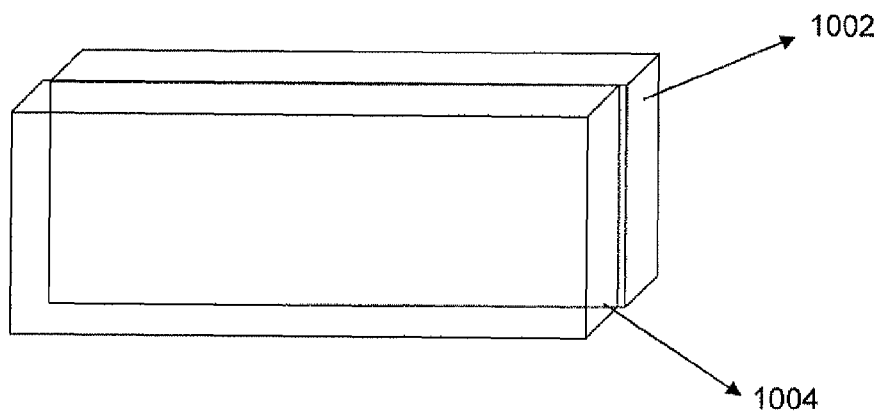
Figure 21A:
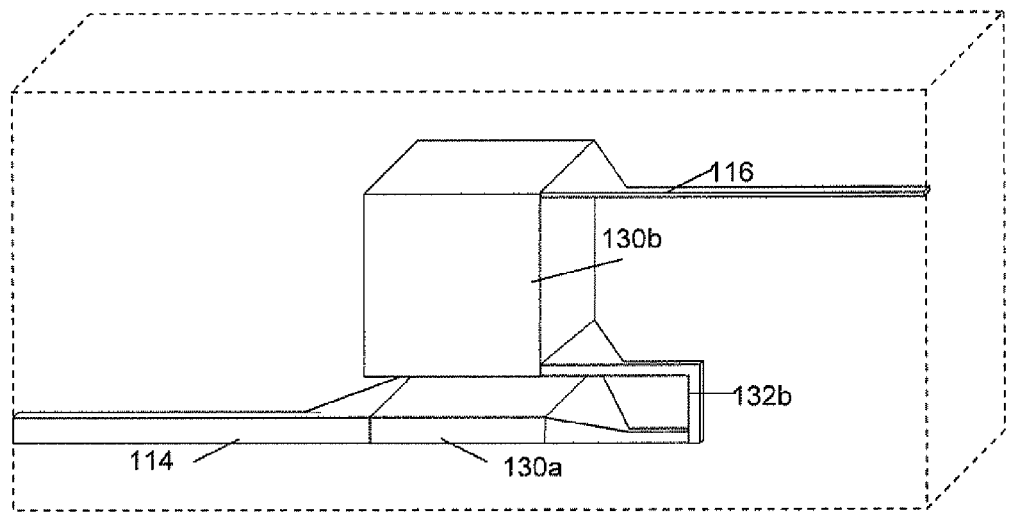
Figure 21B:
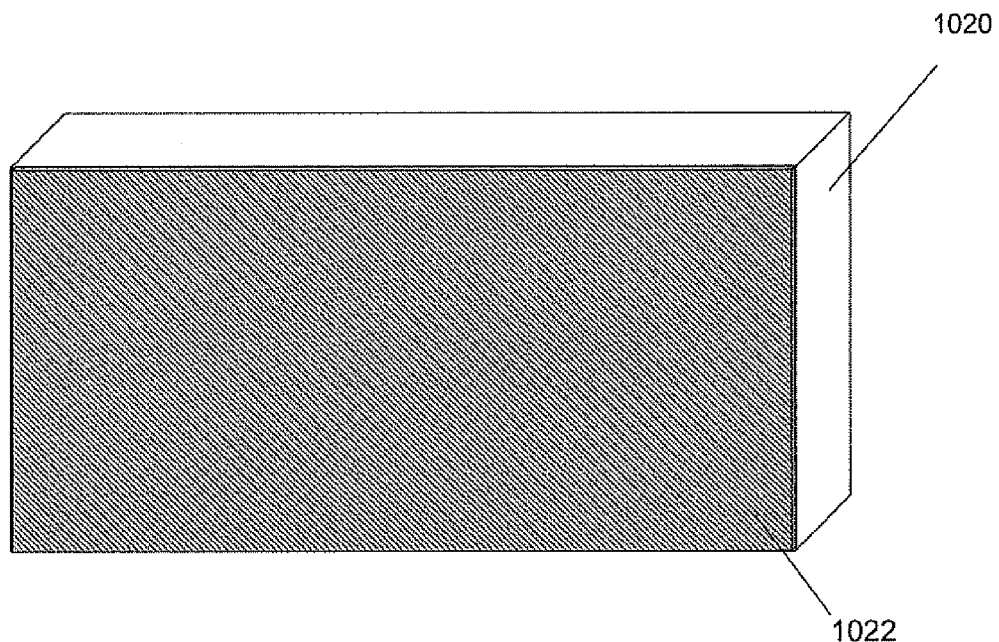

In FIG. 20a to FIG. 22c a plurality of microfluidic structure moulds and moulded microfluidic structures are shown by way of example. These illustrate different possibilities for manufacturing of the microfluidic devices, the invention not being limited thereto. In FIG. 20a and FIG. 20b an example of a transparent view of a mould and a top view of the moulded device comprising two parts 1002, 1004 for a microfluidic device are shown, each of the two moulded parts 1002, 1004 comprising structural features at one side. For these moulds, features are introduced in each of two moulds. The features for the microfluidic device illustrated comprise an input channel 114, two measurement sub-reservoirs 130a, 130b interconnected with a interconnection channel 132b, and an output channel 116. Such a technique can for example be used for moulding microfluidic devices comprising cylindrical or cylindrical reservoirs. Bonding of the two microfluidic parts can be done by thermal bonding e.g. diffusion bonding, using glue or adhesives, using ultrasonic bonding, using chemical bonding, etc. In FIG. 21a and FIG. 21b an alternative example for obtaining a moulded microfluidic device is shown, whereby the features of the microfluidic device are formed in a single mould. The features then preferably show slanted surfaces in order to be able to easily remove the mould after finishing of the moulding. Such technique again can e.g. be used for prismatic chambers. By way of example, in FIG. 21a, a mould with features for a microfluidic comprising an input channel 114, two measurement sub-reservoirs 130a, 130b interconnected with a interconnection channel 132b, and an output channel 116 are illustrated. The moulded part 1020 can be closed by means of a sealing foil 1022 as illustrated in FIG. 21b or using another molded part or a more rigid sheet. Bonding between the moulded part 1020 and the sealing part 1022 again can be done by thermal bonding e.g. diffusion bonding, using glue or adhesives, using ultrasonic bonding, using chemical bonding, etc.

Figure 22A:
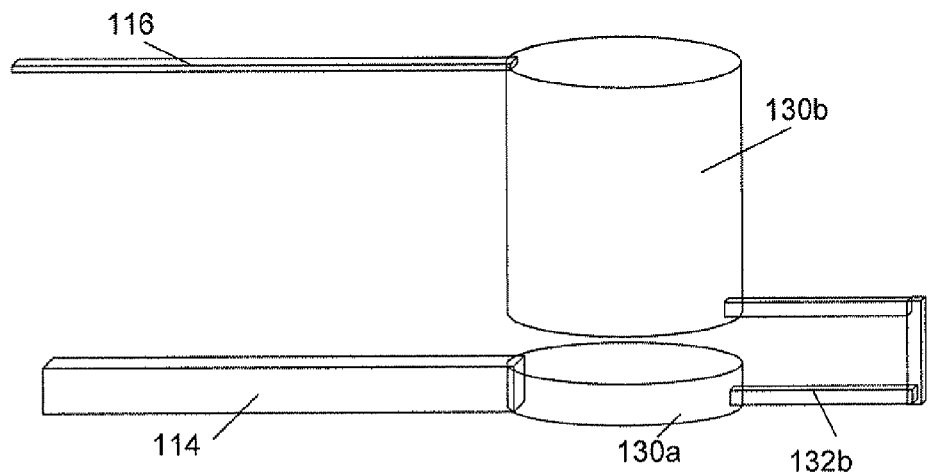
Figure 22B:
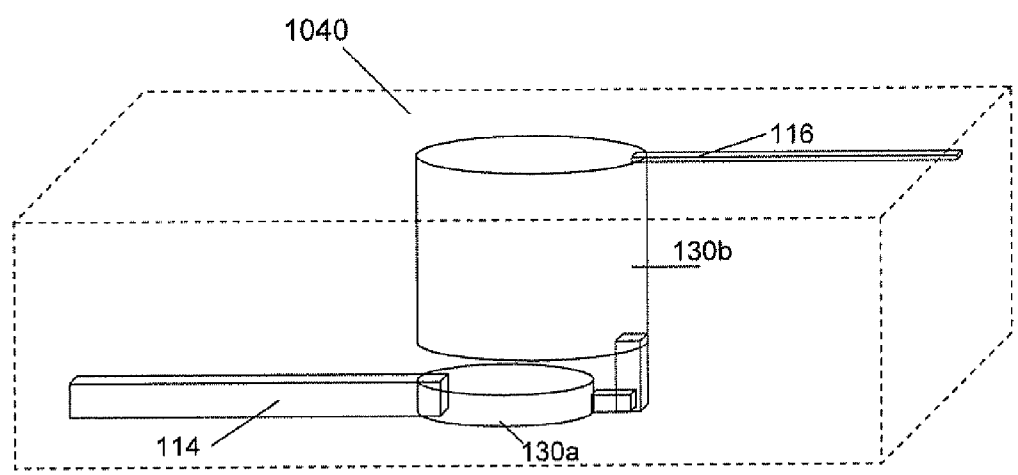
Figure 22C:
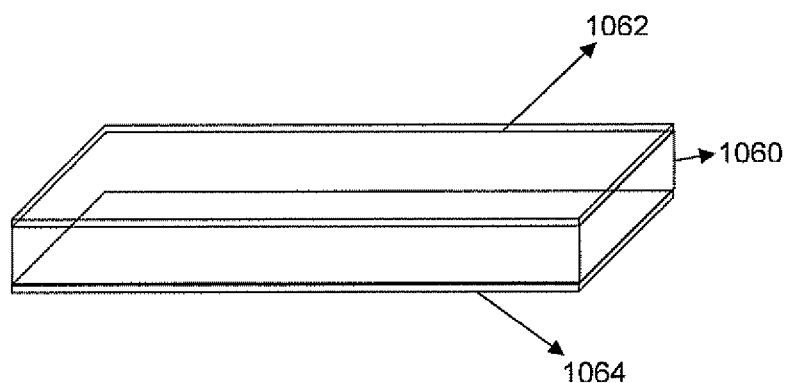

In FIG. 22a to FIG. 22c respectively a microfluidic device structure (or part thereof), a mould with features for generating a microfluidic device structure similar to that shown in FIG. 22a and a top view of a final structure are shown. Again a microfluidic device with a two-chambered microfluidic device is shown, comprising an input channel 114, two measurement sub-reservoirs 130a, 130b interconnected with a interconnection channel 132b, and an output channel 116 are illustrated. Such a device can be moulded using a mould whereby the features of the microfluidic device are introduced in a mould element 1040 at both sides. The mould element 1040 needs to be closed by further providing e.g. a seal element 1062, such as e seal tape, a further moulded part or a more rigid sheet. In the present example, the other side of the moulded part may also be sealed using a seal element 1062. If features of the microfluidic device extend to the edge surface of the moulded part, these thus may be sealed using a sealing foil, another moulded part or a rigid sheet. Bonding between the sealing foil or rigid sheet and the moulded part or between two moulded parts can again be performed using thermal bonding such as e.g. diffusion bonding, using glue or an adhesive sheet, using ultrasonic bonding or using chemical bonding.

In one aspect, the present invention also relates to a device for assisting in optical characterisation of a fluid wherein a dissolvable material is used for providing information regarding the filling of the measurement reservoir. The device comprises a substrate with at least one measurement reservoir adapted for being filled with the fluid. The device comprises at least one dissolvable material that is adapted, e.g. due to its position in the device, for providing information regarding the filling of the measurement reservoir. The at least one dissolvable material may be provided in the measurement reservoir and provide information regarding the start of the filling of the measurement reservoir, the completeness of the filling of the measurement reservoir or the optical path length of the illumination beam in the fluid. The at least one dissolvable material therefor may be positioned at any suitable position in the device, such as e.g. in the input channel or at the bottom of the measurement reservoir with respect to the filling direction, in the output channel or at the top of the measurement reservoir with respect to the filling direction, or at a side wall or in an intermediate channel between sub-reservoirs of the measurement reservoir. The information of the filling may be obtained when the dissolvable material is contacted with the fluid. Depending on the position of the dissolvable material and the information to be obtained about the filling, the information may be obtained using the illumination beam and detector used for characterising the fluid and/or a separate optical detection system, e.g. provided in the output channel of the device. The device may thus provide information on whether the sample has been contacted with reagents, whether the complete measurement reservoir was filled, whether a washing step is done, whether a measurement reservoir has already been used, etc. The dissolvable material also may provide information regarding the optical path length of the illumination beam in the sample fluid, as described with respect to the above aspects. The measurement reservoir therefore may comprise measurement reservoir side walls, and the measurement reservoir may comprise at least one dissolvable material positioned on a measurement reservoir side wall between a top and bottom of the measurement reservoir with respect to the filling direction. Examples thereof are shown in FIG. 23a and FIG. 23d.

The at least one dissolvable material may be adapted for varying the rate of change of an optical path length of the illumination beam in the fluid as function of the filling rate. The optical path length of the illumination beam in the fluid thereby may be defined as the product of the geometric distance and the refractive index, or in a medium of varying refractive index, the integral of the local refractive index along the optical path, represented by $$\int_{opticalpath} n \, ds$$

with ds an element of length along the path.

The dissolvable material may provide a reaction with the sample that is measurable optically. The dissolvable material may for example be adapted for, when being dissolved by contacting with the fluid, changing the absorption coefficient of the fluid. The dissolvable material may comprise a colorant. The dissolvable material may be the reagents, whereby interaction between the sample fluid and the reagents provides an optical influence of the optical path length indicative of the filling of the measurement reservoir. The optical influence of the optical path length may be distinct from the optical influence indicative of the assay reaction for characterising the fluid optically. In other words, the optical influence of the optical path length providing information regarding the filling preferably occurs optically distinct from the optical influence indicative of the occurring assay reaction for biochemically or biotechnically characterising the sample fluid, e.g. in a different wavelength region. If the reagents provides both these optical effects, the reagents may be used as dissolvable material. The dissolvable material may be provided as a dissolvable coating.

By way of illustration, a number of examples are discussed. In one example, a dissolvable material may be provided in the device with a reagent material, e.g. reagent layer on top. An adjustment of the optical path length of the illumination beam due to the dissolvable material then is indicative of the fluid having being contacted with the reagent material. In another example, a dissolvable material may be provided at the input channel or the bottom of the measurement reservoir. An adjustment of the optical path length of the illumination beam due to the dissolvable material then is indicative of the fluid being present in the measurement reservoir. In still another example, the absence of an adjustment of the optical path length of the illumination beam due to dissolvable material may be indicative of the measurement reservoir already being used.

The present invention also relates to a corresponding method for optical characterising a sample fluid, the method comprising illuminating a measurement reservoir adapted to be filled with sample fluid and filling said measurement reservoir with sample fluid, and dissolving, in the device, dissolvable material for providing information regarding the filling of the measurement reservoir. The dissolving may be performed during filling of the measurement reservoir. Dissolving dissolvable material may be for influencing the optical path length of the illumination beam in the fluid or as indicator for indicating that the conditions for performing the assay are fulfilled, e.g. indicative of the filling of the measurement reservoir, indicative of an interaction with the reagents, indicative of the measurement reservoir already being used, indicative of the degree of filling of the measurement reservoir, e.g. indicative of the optical path length of the illumination beam in the fluid during filling, as described in more detail above, etc.

It is an advantage of particular embodiments according to the present invention that the measurement reservoirs used can be made small, such that the amount of sample fluid required for optical characterisation may be small.

It is an advantage of particular embodiments according to the present invention that optical characterisation can be performed with a good accuracy.

It is to be understood that although preferred embodiments, specific constructions and configurations, as well as materials, have been discussed herein for devices according to the present invention, various changes or modifications in form and detail may be made. For example, whereas in the present invention for example an optical characterisation device is described, the present invention also relates to a controller adapted for controlling optical characterisation in such an optical characterisation device. Such a controller can be adapted for synchronising a filling of the least one measurement reservoir 104 and a detecting by the detection unit 208.

The invention claimed is:

1. A device for assisting an optical characterization device in optical characterization of a fluid, the optical characterization device comprising an illumination unit and a detection unit,
the device for assisting comprising a substrate with at least one measurement reservoir adapted for filling with the fluid in a filling direction with a filling rate,
the device for assisting being adapted for receiving an illumination beam from the illumination unit for illuminating the fluid in the at least one measurement reservoir along an optical axis substantially oriented along said filling direction,
the detection unit of the optical characterization device being adapted for detecting an optical detection signal generated by interaction between the illumination beam and the fluid over an optical path length of the illumination beam in the fluid in the at least one measurement reservoir, the at least one measurement reservoir being adapted for varying the rate of change of the optical detection signal in the fluid as a function of the filling rate, wherein
the at least one measurement reservoir is adapted so as to induce a variation in a second derivative of the optical detection signal as a function of the amount of fluid added to the measurement reservoir such that the at least one measurement reservoir is adapted for providing information of the optical path length of the illumination beam in the fluid at a plurality of moments in time during the filling with the fluid.

2. The device according to claim 1, wherein the at least one measurement reservoir is constructed of material having hydrophilic/hydrophobic material properties and/or a shape that, when interacting with the fluid, causes or induces a variation in the second derivative of the optical detection signal.

3. The device according to claim 2, wherein the at least one measurement reservoir comprises sub-reservoirs, said measurement reservoir being adapted for being illuminated along an illumination path, wherein the sub-reservoirs are positioned subsequently along said illumination path in said at least one measurement reservoir.

4. The device according to claim 2, wherein the at least one measurement reservoir shape comprises at least one discontinuous variation in cross-section perpendicular to the filling direction.

5. The device according to claim 4, wherein the at least one measurement reservoir comprises a number of cross-sections perpendicular to the filling direction crossing the optical path length of the illumination beam through said at least one measurement reservoir and at least one intermediate cross-section perpendicular to the filling direction not crossing the optical path length of the illumination beam.

6. The device according to claim 2, wherein the at least one measurement reservoir comprises measurement reservoir walls, the measurement reservoir walls having different hydrophilic properties in different parts of the measurement reservoir.

7. The device according to claim 1, wherein the at least one measurement reservoir comprises at least one dissolvable material adapted for, when being dissolved by contacting with the fluid, providing information of the optical path length of the illumination beam in the fluid.

8. The device according to claim 7, wherein the dissolvable material is adapted for, when being dissolved by contacting with the fluid, changing the absorption coefficient of the fluid.

9. An optical characterization device for characterizing a fluid, the optical characterization device comprising an illumination unit, a detection unit, a device for assisting in optical characterization of a fluid and a fluid providing arrangement adapted to fill an at least one measurement reservoir with the fluid in a filling direction and an evaluation device arranged to determine information regarding an optical path length of an illumination beam in the fluid from optical detection signals taking into account properties of the measurement reservoir, the device for assisting in optical characterization of a fluid comprising a substrate comprising the at least one measurement reservoir adapted for filling with the fluid in a filling direction with a filling rate and the device being adapted for receiving an illumination beam from the illumination unit for illuminating the fluid in the at least one measurement reservoir along an optical axis substantially oriented along said filling direction, the detection unit of the optical characterization device adapted for detecting an optical detection signal generated by interaction between the illumination beam and the fluid over an optical path length of the illumination beam in the fluid in the at least one measurement reservoir, the at least one measurement reservoir being adapted for varying the rate of change of an optical detection signal in the fluid as function of the filling rate, wherein the at least one measurement reservoir is adapted so as to induce a variation in a second derivative of the optical detection signal as a function of the amount of fluid added to the measurement reservoir such that the at least one measurement reservoir is adapted for providing information of the optical path length of the illumination beam in the fluid at a plurality of moments in time during the filling with the fluid.

10. The optical characterisation device according to claim 9, wherein the detection unit is controllable by a controller for detecting at least two optical detection signals, a first optical detection signal corresponding with a known illumination beam path length in the fluid to be characterised and a second optical detection signal corresponding with an unknown illumination beam path length in the fluid to be characterised, the known illumination beam path length being substantially larger than the unknown illumination beam path length, the optical characterisation device furthermore comprising a processing device arranged to derive the unknown illumination beam path length based on said at least two optical detection signals and said known illumination beam path length.

11. A method for optical characterizing a fluid using an optical characterization device, the method comprising:
illuminating a measurement reservoir of said optical characterization device adapted to be filled with fluid and filling said measurement reservoir with fluid in a filling direction, and
during said illuminating and filling, detecting at a plurality of moments in time an optical detection signal using a detector of said optical characterization device from said fluid generated by illuminating the fluid in the at least one measurement reservoir along an optical axis substantially oriented along said filling direction,
deriving a characteristic of the fluid taking into account a shape of the measurement reservoir, and
characterizing based thereon specific analytes present in the fluid,
wherein the deriving takes into account a variation of the rate of change of an optical detection signal in the fluid as a function of the filling rate, the variation being induced by the at least one measurement reservoir of said optical characterization device adapted for inducing a variation in a second derivative of the optical detection signal as a function of the amount of sample fluid added to the measurement reservoir.

12. The method according to claim 11, the method comprising subsequently filling sub-reservoirs of said at least one measurement reservoir positioned subsequently along an illumination path in said at least one measurement reservoir.

13. A non-transitory computer readable medium adapted for, when executed on a computing device, performing a method for optically characterizing a fluid, the computer program product being adapted for
controlling illumination of a measurement reservoir adapted to be filled with fluid and filling of said measurement reservoir with fluid in a filling direction, and
during said illuminating and filling, controlling detection at a plurality of moments in time an optical detection signal from said fluid generated by illuminating the fluid in the at least one measurement reservoir along an optical axis substantially oriented along said filling direction, and
deriving a characteristic of the fluid taking into account a shape of the measurement reservoir, wherein
the deriving takes into account a variation of the rate of change of an optical detection signal in the fluid as a function of the filling rate, the variation being induced by the measurement reservoir adapted for inducing a variation in a second derivative of the optical detection signal as a function of the amount of fluid added to the measurement reservoir.

* * * * *